(12) United States Patent
Dubrow et al.

(10) Patent No.: US 7,972,616 B2
(45) Date of Patent: *Jul. 5, 2011

(54) MEDICAL DEVICE APPLICATIONS OF NANOSTRUCTURED SURFACES

(75) Inventors: Robert S. Dubrow, San Carlos, CA (US); Lawrence A. Bock, Encinitas, CA (US); R. Hugh Daniels, Mountain View, CA (US); Veeral D. Hardev, Redwood City, CA (US); Chunming Niu, Palo Alto, CA (US); Vijendra Sahi, Menlo Park, CA (US)

(73) Assignee: Nanosys, Inc., Palo Alto, CA (US)

( * ) Notice: Subject to any disclaimer, the term of this patent is extended or adjusted under 35 U.S.C. 154(b) by 439 days.

This patent is subject to a terminal disclaimer.

(21) Appl. No.: 11/330,722

(22) Filed: Jan. 12, 2006

(65) Prior Publication Data
US 2006/0204738 A1 Sep. 14, 2006

Related U.S. Application Data

(63) Continuation-in-part of application No. 11/090,895, filed on Mar. 24, 2005, now abandoned, which is a continuation-in-part of application No. 10/902,700, filed on Jul. 29, 2004, application No. 11/330,722, which is a continuation-in-part of application No. 10/828,100, filed on Apr. 19, 2004, now Pat. No. 7,074,294, which is a continuation-in-part of application No. 10/825,861, filed on Apr. 16, 2004, now abandoned, which is a continuation-in-part of application No. 10/661,381, filed on Sep. 12, 2003, now Pat. No. 7,056,409, application No. 11/330,722, which is a continuation-in-part of application No. 10/833,944, filed on Apr. 27, 2004, application No. 11/330,722, which is a continuation-in-part of application No. 10/840,794, filed on May 5, 2004, now Pat. No. 7,579,077, which is a continuation-in-part of application No. 10/792,402, filed on Mar. 2, 2004, now abandoned.

(60) Provisional application No. 60/549,711, filed on Mar. 2, 2004, provisional application No. 60/463,766, filed on Apr. 17, 2003, provisional application No. 60/466,229, filed on Apr. 28, 2003, provisional application No. 60/468,390, filed on May 6, 2003, provisional application No. 60/468,606, filed on May 5, 2003.

(51) Int. Cl.
*A61K 33/38* (2006.01)
*A61K 9/70* (2006.01)
*B32B 5/16* (2006.01)
*B32B 37/00* (2006.01)
*B22F 7/04* (2006.01)

(52) U.S. Cl. ........ 424/423; 424/443; 424/618; 428/560; 604/19; 977/811; 977/900; 977/906

(58) Field of Classification Search .................. None
See application file for complete search history.

(56) References Cited

U.S. PATENT DOCUMENTS

| | | |
|---|---|---|
| 4,475,972 A | 10/1984 | Wong |
| 4,911,781 A | 3/1990 | Fox et al. |
| 5,116,360 A | 5/1992 | Pinchuk et al. |
| 5,196,396 A | 3/1993 | Lieber |
| 5,252,835 A | 10/1993 | Lieber et al. |
| 5,332,910 A | 7/1994 | Haraguchi et al. |
| 5,505,928 A | 4/1996 | Alivisatos et al. |
| 5,634,946 A | 6/1997 | Slepian |
| 5,690,807 A | 11/1997 | Clark, Jr. et al. |
| 5,751,018 A | 5/1998 | Alivisatos et al. |
| 5,840,435 A | 11/1998 | Lieber et al. |
| 5,897,945 A | 4/1999 | Lieber et al. |
| 5,976,826 A | 11/1999 | Singhvi et al. |
| 5,976,957 A | 11/1999 | Westwater et al. |
| 5,985,112 A * | 11/1999 | Fischer .......... 204/283 |
| 5,985,328 A | 11/1999 | Chu et al. |
| 5,990,479 A | 11/1999 | Wess et al. |
| 5,997,832 A | 12/1999 | Lieber et al. |
| 6,036,774 A | 3/2000 | Lieber et al. |
| 6,048,616 A | 4/2000 | Gallagher et al. |
| 6,099,960 A | 8/2000 | Tennent et al. |
| 6,099,965 A | 8/2000 | Tennet et al. |
| 6,106,913 A | 8/2000 | Scardino et al. |

(Continued)

FOREIGN PATENT DOCUMENTS
DE 19713214 A1 12/1998
(Continued)

OTHER PUBLICATIONS

Soppimath et al., Journal of Controlled Release, 2001, vol. 70, p. 1-20.*

(Continued)

*Primary Examiner* — Jon P Weber
*Assistant Examiner* — Kailash Srivastava
(74) *Attorney, Agent, or Firm* — Donna M. Fabian; Andrew L. Filler

(57) ABSTRACT

This invention provides novel nanofiber enhanced surface area substrates and structures comprising such substrates for use in various medical devices, as well as methods and uses for such substrates and medical devices. In one particular embodiment, methods for enhancing cellular functions on a surface of a medical device implant are disclosed which generally comprise providing a medical device implant comprising a plurality of nanofibers (e.g., nanowires) thereon and exposing the medical device implant to cells such as osteoblasts.

62 Claims, 19 Drawing Sheets

U.S. PATENT DOCUMENTS

| | | | |
|---|---|---|---|
| 6,130,143 A | 10/2000 | Westwater et al. | |
| 6,136,156 A | 10/2000 | El-Shall et al. | |
| 6,159,742 A | 12/2000 | Lieber et al. | |
| 6,190,634 B1 | 2/2001 | Lieber et al. | |
| 6,207,229 B1 | 3/2001 | Bawendi et al. | |
| 6,225,198 B1 | 5/2001 | Alivisatos et al. | |
| 6,265,333 B1 | 7/2001 | Dzenis et al. | |
| 6,268,041 B1 | 7/2001 | Goldstein | |
| 6,270,347 B1 | 8/2001 | Webster et al. | |
| 6,286,226 B1 | 9/2001 | Jin | |
| 6,288,390 B1 | 9/2001 | Siuzdak et al. | |
| 6,306,736 B1 | 10/2001 | Alivisatos et al. | |
| 6,313,015 B1 | 11/2001 | Lee et al. | |
| 6,319,321 B1* | 11/2001 | Hiraga et al. | 118/666 |
| 6,322,895 B1 | 11/2001 | Canham | |
| 6,359,288 B1 | 3/2002 | Ying et al. | |
| 6,361,861 B2 | 3/2002 | Gao et al. | |
| 6,362,011 B1 | 3/2002 | Massey et al. | |
| 6,383,923 B1 | 5/2002 | Brown et al. | |
| 6,399,177 B1 | 6/2002 | Fonash et al. | |
| 6,413,489 B1 | 7/2002 | Ying et al. | |
| 6,515,009 B1 | 2/2003 | Kunz et al. | |
| 6,656,966 B2 | 12/2003 | Garvey et al. | |
| 6,666,214 B2 | 12/2003 | Canham | |
| 6,667,099 B1 | 12/2003 | Greiner et al. | |
| 6,669,256 B2 | 12/2003 | Nakayama et al. | |
| 6,670,179 B1 | 12/2003 | Mattson et al. | |
| 6,689,166 B2 | 2/2004 | Laurencin et al. | |
| 6,709,622 B2 | 3/2004 | Billiet et al. | |
| 6,713,519 B2 | 3/2004 | Wang et al. | |
| 6,720,240 B2 | 4/2004 | Gole et al. | |
| 6,737,160 B1 | 5/2004 | Full et al. | |
| 6,737,447 B1 | 5/2004 | Smith et al. | |
| 6,743,408 B2 | 6/2004 | Lieber et al. | |
| 6,766,817 B2 | 7/2004 | Da Silva | |
| 6,794,196 B2 | 9/2004 | Fonash et al. | |
| 6,808,535 B1 | 10/2004 | Jordan | |
| 6,811,957 B1 | 11/2004 | Mau et al. | |
| 6,831,017 B1 | 12/2004 | Li et al. | |
| 6,872,439 B2 | 3/2005 | Fearing et al. | |
| 6,882,051 B2 | 4/2005 | Majumdar et al. | |
| 6,896,864 B2 | 5/2005 | Clarke | |
| 6,958,216 B2 | 10/2005 | Kelley et al. | |
| 6,969,690 B2 | 11/2005 | Zhou et al. | |
| 7,011,723 B2 | 3/2006 | Full et al. | |
| 7,037,332 B2 | 5/2006 | Kutryk et al. | |
| 7,056,409 B2* | 6/2006 | Dubrow | 156/276 |
| 7,057,881 B2 | 6/2006 | Chow et al. | |
| 7,064,372 B2 | 6/2006 | Duan et al. | |
| 7,067,328 B2 | 6/2006 | Dubrow et al. | |
| 7,070,810 B2 | 7/2006 | Hirsch et al. | |
| 7,074,294 B2* | 7/2006 | Dubrow | 156/276 |
| 7,129,554 B2 | 10/2006 | Lieber et al. | |
| 7,132,161 B2 | 11/2006 | Knowles et al. | |
| 7,135,728 B2 | 11/2006 | Duan et al. | |
| 7,147,894 B2 | 12/2006 | Zhou et al. | |
| 7,163,659 B2 | 1/2007 | Stasiak et al. | |
| 7,181,811 B1 | 2/2007 | Tomanek et al. | |
| 7,195,780 B2 | 3/2007 | Dennis et al. | |
| 7,229,685 B2 | 6/2007 | Full et al. | |
| 7,232,460 B2 | 6/2007 | Erlach et al. | |
| 2001/0051766 A1 | 12/2001 | Gazdzinski | |
| 2002/0001977 A1* | 1/2002 | Gole et al. | 438/800 |
| 2002/0037383 A1 | 3/2002 | Spillman et al. | |
| 2002/0049495 A1 | 4/2002 | Kutryk et al. | |
| 2002/0061662 A1 | 5/2002 | Boggild | |
| 2002/0090725 A1 | 7/2002 | Simpson et al. | |
| 2002/0092423 A1 | 7/2002 | Gillingham et al. | |
| 2002/0130311 A1 | 9/2002 | Lieber et al. | |
| 2002/0167118 A1 | 11/2002 | Billiet et al. | |
| 2002/0172963 A1 | 11/2002 | Kelley et al. | |
| 2003/0012723 A1 | 1/2003 | Clarke | |
| 2003/0032892 A1 | 2/2003 | Erlach et al. | |
| 2003/0059742 A1 | 3/2003 | Webster et al. | |
| 2003/0065355 A1 | 4/2003 | Weber | |
| 2003/0089899 A1 | 5/2003 | Lieber et al. | |
| 2003/0093107 A1 | 5/2003 | Parsonage et al. | |
| 2003/0119920 A1 | 6/2003 | Wang et al. | |
| 2003/0124312 A1 | 7/2003 | Autumn | |
| 2003/0146529 A1 | 8/2003 | Chen et al. | |
| 2003/0189202 A1 | 10/2003 | Li et al. | |
| 2003/0195611 A1 | 10/2003 | Greenhalgh et al. | |
| 2003/0208888 A1 | 11/2003 | Fearing et al. | |
| 2003/0211129 A1 | 11/2003 | Spillman et al. | |
| 2003/0229393 A1 | 12/2003 | Kutryk et al. | |
| 2004/0005454 A1 | 1/2004 | Full et al. | |
| 2004/0009598 A1 | 1/2004 | Hench et al. | |
| 2004/0018371 A1 | 1/2004 | Mao | |
| 2004/0023317 A1 | 2/2004 | Motamedi et al. | |
| 2004/0026684 A1 | 2/2004 | Empedocles | |
| 2004/0052867 A1 | 3/2004 | Canham | |
| 2004/0071870 A1 | 4/2004 | Knowles et al. | |
| 2004/0076681 A1 | 4/2004 | Dennis et al. | |
| 2004/0076822 A1 | 4/2004 | Jagota et al. | |
| 2004/0079278 A1 | 4/2004 | Kamins | |
| 2004/0098023 A1 | 5/2004 | Lee et al. | |
| 2004/0106203 A1 | 6/2004 | Stasiak et al. | |
| 2004/0115239 A1 | 6/2004 | Shastri et al. | |
| 2004/0244677 A1 | 12/2004 | Takami | |
| 2004/0250950 A1 | 12/2004 | Dubrow et al. | |
| 2004/0258726 A1 | 12/2004 | Stupp et al. | |
| 2005/0011431 A1 | 1/2005 | Samuelson et al. | |
| 2005/0017171 A1 | 1/2005 | Samuelson et al. | |
| 2005/0038498 A1 | 2/2005 | Dubrow et al. | |
| 2005/0048127 A1 | 3/2005 | Brown et al. | |
| 2005/0048859 A1 | 3/2005 | Canham et al. | |
| 2005/0055078 A1 | 3/2005 | Campbell | |
| 2005/0072509 A1 | 4/2005 | Full et al. | |
| 2005/0096509 A1 | 5/2005 | Olson | |
| 2005/0118494 A1 | 6/2005 | Choi | |
| 2005/0148984 A1 | 7/2005 | Lindsay et al. | |
| 2005/0156504 A1 | 7/2005 | Takai et al. | |
| 2005/0181195 A1 | 8/2005 | Dubrow | |
| 2005/0187605 A1 | 8/2005 | Greenhalgh et al. | |
| 2005/0219788 A1 | 10/2005 | Chow et al. | |
| 2005/0221072 A1 | 10/2005 | Dubrow et al. | |
| 2005/0245637 A1 | 11/2005 | Hossainy et al. | |
| 2005/0260355 A1 | 11/2005 | Weber et al. | |
| 2006/0005362 A1 | 1/2006 | Arzt et al. | |
| 2006/0054936 A1 | 3/2006 | Lieber et al. | |
| 2006/0159916 A1 | 7/2006 | Dubrow et al. | |
| 2006/0204738 A1 | 9/2006 | Dubrow et al. | |

FOREIGN PATENT DOCUMENTS

| | | |
|---|---|---|
| EP | 923912 A2 | 6/1999 |
| EP | 1191121 A1 | 3/2002 |
| WO | WO-9629629 | 9/1996 |
| WO | WO-9918893 | 4/1999 |
| WO | WO-9940812 | 8/1999 |
| WO | WO-0044357 | 8/2000 |
| WO | WO-0126702 | 4/2001 |
| WO | WO-0149776 | 7/2001 |
| WO | 0187193 A1 | 11/2001 |
| WO | WO-0217362 | 2/2002 |
| WO | WO-02080280 | 10/2002 |
| WO | 02087648 | 11/2002 |
| WO | WO-03095190 | 11/2003 |
| WO | WO-03097702 | 11/2003 |
| WO | WO-03099951 | 12/2003 |
| WO | WO-03102099 | 12/2003 |
| WO | 2004096085 A2 | 11/2004 |
| WO | WO-2004094303 | 11/2004 |
| WO | WO-2004099068 | 11/2004 |
| WO | WO-2005005679 | 1/2005 |

OTHER PUBLICATIONS

Turner et al., J. Vac. Sci. Technol. B, 1997, vol. 6, p. 2848-2854.*
Puleo & Nanci, Biomaterials, 1999, vol. 20, p. 2311-2321.*
Murayama et al., Stroke 2002, vol. 33, p. 1120-1128.*
Westwater et al., J. Vac. Sci Technol. B 2997, vol. 15, No. 3, p. 554-557.*
Flahaut et al., Acta mater., 2000, vol. 48, p. 3803-3812.*
Kay et al., Tissue Engineering, Oct. 2002, vol. 8, No. 5, p. 753-761.*
Olson et al., Eur J Surg, 2000, vol. 166, p. 486-489.*
Online Medical Dictionary, Nov. 1997.*
Uzan et al., Neurosurg. Rev. 1996, vol. 19, p. 89-91.*

Abiraman et al., Biomaterials, 2002, vol. 23, p. 3023-3031.*
Autumn et al., PNAS, 2002, vol. 99, No. 19, p. 12252-12256.*
Autumn, K. et al., "Adhesive force of a single gecko foot-hair" Nature (2000) 405:681-685.
Bjork, M.T. et al., "One-dimensional steeplechase for electrons realized" Nano Letters (2002) 2:86-89.
Cao, Y.W. et al., "Growth and properties of semiconductor core/shell nanocrystals witn InAs cores" J. Am. Chem. Soc. (2000) 122:9692-9702.
Chen, I.W. et al., "Sintering dense nanocrystalline ceramics without final-stage grain growth" Nature (2000) 404(6774):168-171.
Choi, H. et al., "Surface-modified silica colloid for diagnostic imaging" J. Colloid Interface Sci (2003) 258(2):435-437.
Cui, Y. et al. "Doping and electrical transport in silicon nanowires" J. Phys. Chem. B (2000) 104(22):5213-5216.
Cui et al., "Functional nanoscale electronic devices assembled using silicon nanowire building blocks" Science (2001) 291:851-853.
Cui et al., "Nanowire nanosensors for highly sensitive and selective detection of biological and chemical species" Science (2001) 293:1289-1292.
Cui, Y. et al. "Diameter-controlled synthesis of single-crystal silicon nanowires" (2001) Appl. Phys. Letts. 78(15):2214-2216.
Dabbousi, B.O. et al., "(cdSe)ZnS core-shell quantum dots: Synthesis and characterization of a sizze series of highly luminescent nanocrystallites" J. Phys. Chem. B (1997) 101(46):9463-9475.
Davis, D.H. et al., "Immobilization of RGD to <111> silicon surfaces for enhanced cell adhesion and proliferation" Biomaterials (2002) 23:4019-4027.
Duan, X. et al., "General synthesis of compound semiconductor nanowires" Adv. Mater. (2000) 12(4):298-302.
Duan, X. et al., "Single-nanowire electrically driven lasers" Nature (2003) 421:241-245.
Geim, A.K. et al., "Microfabricated adhesive mimicking gecko foot-hair" Nature Materials (2003) 2:461-463.
Greene, L.E. et al., "Low-Temperature Wafer-Scale Production of ZnO Nanowire Arrays" Angew. Chem. Int. Ed. (2003) 42:3031-3034.
Gudiksen, M.S. et al., "Diameter-selective synthesis of semiconductor nanowires" J. Am. Chem. Soc. (2000) 122:8801-8802.
Gudiksen, M.S. et al., "Synthetic control of the diameter and length of single crystal semiconductor nanowires" J. Phys. Chem. (2001) 105(19):4062-4064.
Gudiksen, M.S. et al., "Growth of nanowire superlattice structures for nanoscale photonics and electronics" Nature (2002) 415:617-620.
Hanekamp C. et al., "Randomized comparison of balloon angioplasty versus silicon carbon-coated stent implantation for de novo lesions in small coronary arteries" Am. J. Cardiol. (2004) 93(10):1233-1237.
Haraguchi, K. et al., "Polarization dependence of light emitted from GaAs p-n junctions in quantum wire crystals" J. Appl. Phys. (1994) 75(8):4220-4225.
Haraguchi, K. et al., "Self organized fabrication of planar GaAs nanowhisker arrays" Appl. Phys. Lett (1996) 69(3):386-387.
Hiruma, K. et al., "GaAs free-standing auntum-sized wires" J. Appl. Phys. (1993) 74(5):3162-3171.
Huang, Y. et al., "Integrated optoelectronics assembed from semiconductor nanowires" Abstracts of Papers of the ACS (2002) 224:U308.
Jun, Y-W. et al., "Controlled synthesis of multi-armed CdS nanorod architectures using monosurfactant system" J. Am. Chem. Soc. (2001) 123(21):5150-5151.
Kong, J. et al., "Chemical vapor deposition of methane for single-walled carbon nanotubes," Chem. Phys. Lett (1998) 292:567-574.
Kong, J. et al., "Synthesis of individual single-walled carbon nanotubes on patterned silicon wafers" Nature (1998) 395:878-881.
Liu, C. et al., "Sol-Gel synthesis of free-standing ferroelectric lead zirconate titanate nanoparticles" J. Am. Chem. Soc. (2001) 123(18):4344-4345.
Manna, L. et al., "Synthesis of soluble and processable rod-, arrow-, teardrop-, and tetrapod-shaped CdSe nanocrystals" J. Am. Chem. Soc. (2000) 122:12700-12706.
Manna, L. et al., "Epitaxial growth and photochemical annealing of graded CdS/ZnS shells on colloidal CdSe nanorods" J. Am. Chem. Soc. (2002) 124:7136-7145.
Morales, A.M. et al., "A laser ablation method for the synthesis of crystalline semiconductor nanowires" Science (1998) 279(9):208-211.
Peng, X. et al., "Epitaxial growth of highly luminescent CsDe/CdS core/shell nanocrystals with photostability and electronic accessibility" J. Am. Chem. Soc. (1997) 119(30):7019-7029.
Peng, X. et al., "Shape control of CdSe nanocrystals" Nature (2000) 404:59-61.
Price, R.L. et al., "Nanometer surface roughness increases select osteoblast adhesion on carbon nanofiber compacts" J. Biomed. Mat. Res. (2004) 70A(1):129-138.
Puntes, V.F. et al., "Colloidal nanocrystal shape and size control: The case of cobalt" Science (2001) 291:2115-2117.
Schon, J.H. et al., "Self-assembled monolayer organic field effect transistors" Nature (2001) 413:713-716.
Shastri, V.P., "Non-degradable biocompatible polymers in medicine: past, present and future" Curr Pharm. Biotechnol. (2003) 4(5):331-337.
Silva, G.A. et al., "Selective differentiation of neural progenitor cells by high-epitope density nanfibers" Science (2004) 303:1352-1355.
Thess, A. et al., "Crystalline ropes of metallic carbon nanotubes" Science (1996) 273:483-487.
Urban, J.J. et al., "Synthesis of single-crystalline perovskite nanorods composed of varium titanate and strontium titanate" J. Am. Chem. Soc. (2002) 124(7):1186-1187.
Webster, T.J. et al., "Nano-biotechnology: carbon nanofibres as improved neural and orthopaedic implants" Nanotechnology (2004) 15:48-54.
Webster, T.J. et al., "Increased osteoblast adhesion on nanophase metals: Ti, Ti6A14V, and CoCrMo" Biomaterials (2004) 25:4731-4739.
Wu, Y. et al., "Block-by-block growth of single-crystalline Si/SiGe superlattice nanowires" Nano Letters (2002) 2(2):83-86.
Xu, H. et al., "Room-temperature preparation and characterization of poly(ethylene glycol)-coated silica nanoparticles for biomedical applications" J. Biomed. Mat. Res. (2003) 66A(4):870-879.
Xu, H. et al., "Strong and bioactive composites containing nano-silica-fused whiskers for bone repair" Biomaterials (2004) 25:4615-4626.
Yang, P. et al., "Inorganic semiconductor nanowires" Nanoscience (2002) 1(1):1-39.
Yazawa, M. et al., "Semiconductor nanowhiskers" Adv. Mater. (1993) 5(7/8):577-580.
Yun, W.S. et al., "Ferroelectric properties of individual barium titanate nanowires investigated by scanned probe microscopy" Nano Letters (2002) 2(2):447-450.
Zhou, C. et al., "Nanoscale metal/self-assumbed monolayer/metal heterostructures" Appl. Phys. Lett (1997) 71(5):611-613.
Zhou, X.T. et al., "Silicon nanowires as chemical sensors" Chem. Phys. Lett. (2003) 369:220-224.
Elias, K.L. et al., "Enhanced functions of osteoblasts on nanometer diameter carbon fibers" Biomaterials (2002) 23:3279-3287.
Ritala, M. et al. "Atomic layer epitaxy—a valuable tool for nanotechnology" Nanotech (1999) 10:19-24.
Suzuki, R. et al. "Inhibition of inflammatory species by titanium surfaces" Clin Orthopaed (2000) 372:280-289.
Magdassi et al. "Patterning of Organic Nanoparticles by Ink-Jet Printing of Microemulsions" Langmuir (2003) 19:939-942.

* cited by examiner

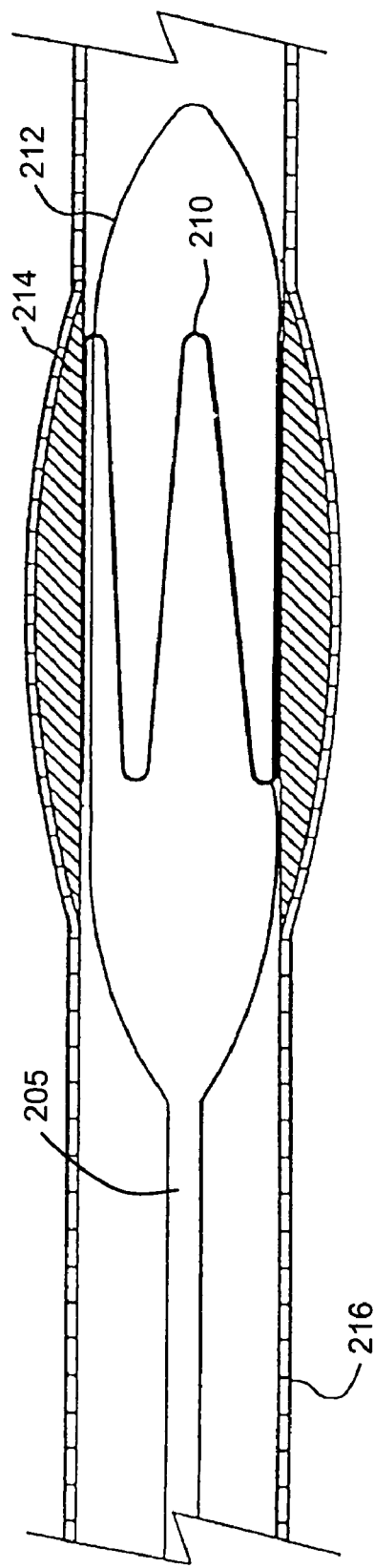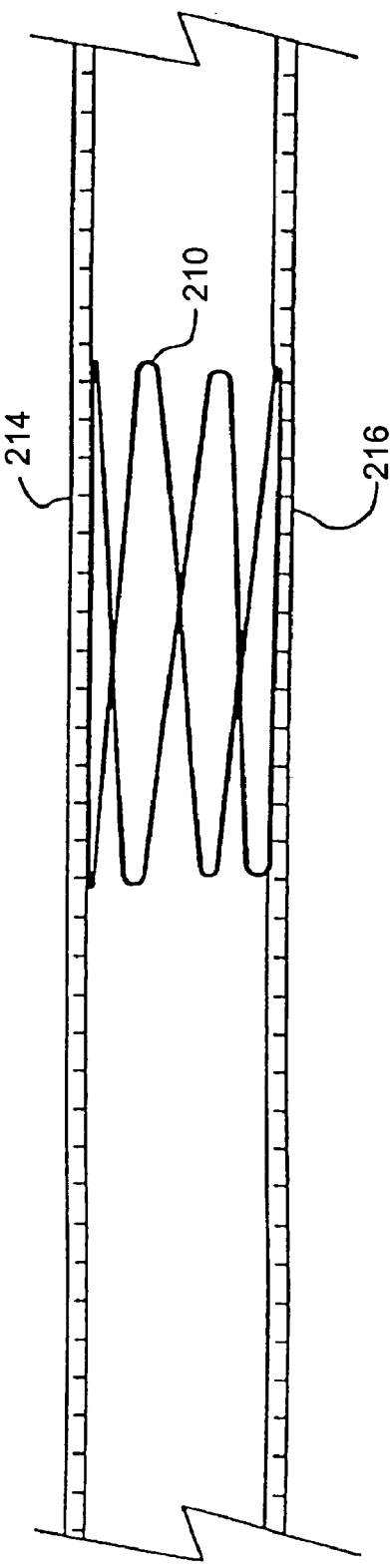
(PRIOR ART) FIG. 2A
(PRIOR ART) FIG. 2B

Quartz    Nanowire

Day 1

Day 4

Week 1

Week 2

Week 3

Week 4

Week 1
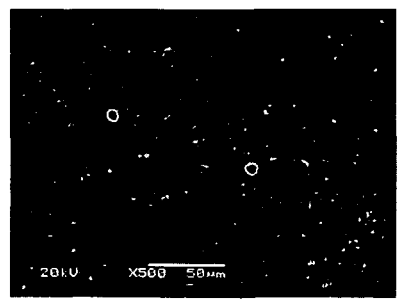 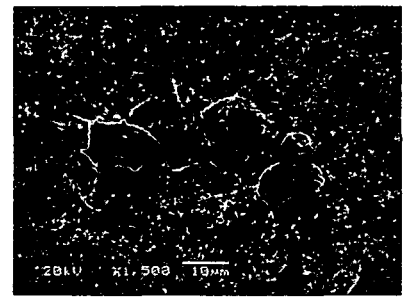
Fig. 12I  Fig. 12J
Week 2
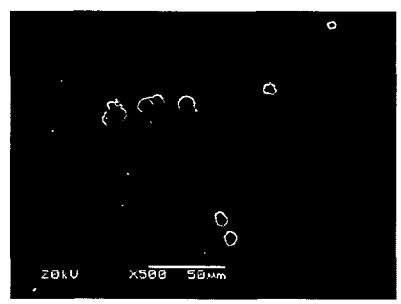 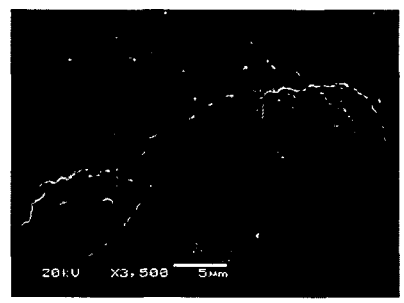
Fig. 12K  Fig. 12L
Week 3
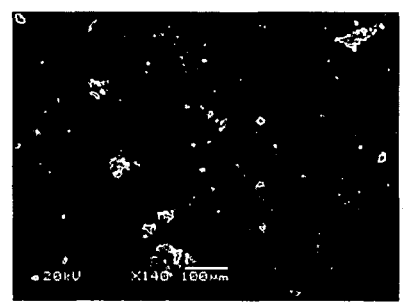 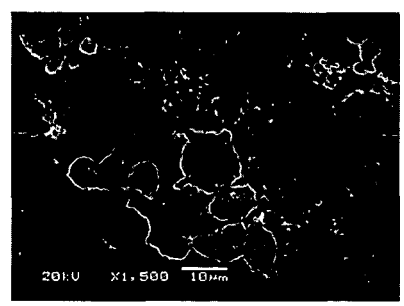
Fig. 12M  Fig. 12N
Week 4
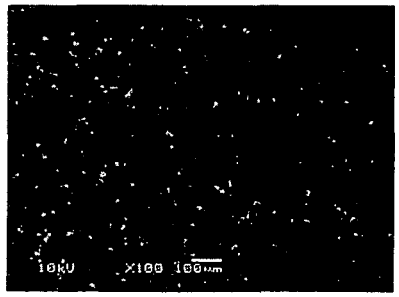 
Fig. 12O  Fig. 12P

MEDICAL DEVICE APPLICATIONS OF NANOSTRUCTURED SURFACES

CROSS-REFERENCE TO RELATED APPLICATIONS

This application is a continuation-in-part application of U.S. patent application Ser. No. 11/090,895 filed Mar. 24, 2005, now abandoned, which claims priority as a continuation-in-part of U.S. patent application Ser. No. 10/902,700 filed Jul. 29, 2004, which claims priority to U.S. Provisional Patent Application Ser. No. 60/549,711, filed Mar. 2, 2004. This application also claims priority as a continuation-in-part application of U.S. patent application Ser. No. 10/828,100, filed Apr. 19, 2004, now U.S. Pat. No. 7,074,294, which is a continuation-in-part of U.S. patent application Ser. No. 10/825,861, filed Apr. 16, 2004, now abandoned, which is a continuation-in-part of U.S. patent application Ser. No. 10/661,381, filed Sep. 12, 2003, now U.S. Pat. No. 7,056,409, which claims priority to U.S. Provisional Patent Application No. 60/463,766, filed Apr. 17, 2003; and as a continuation-in-part of U.S. patent application Ser. No. 10/833,944, filed Apr. 27, 2004, which claims priority to U.S. Provisional Application Ser. No. 60/466,229, filed Apr. 28, 2003; and as a continuation-in-part application of U.S. patent application Ser. No. 10/840,794 filed May 5, 2004, now U.S. Pat. No. 7,579,077, which is a continuation-in-part of U.S. patent application Ser. No. 10/792,402, filed Mar. 2, 2004, now abandoned, which claims priority to U.S. Provisional Patent Application Ser. Nos. 60/468,390, filed May 6, 2003 and 60/468,606 filed May 5, 2003; all of the above patents and applications are hereby incorporated herein by reference in their entirety.

FIELD OF THE INVENTION

The invention relates primarily to the field of nanotechnology. More specifically, the invention pertains to medical devices containing nanostructures, composite materials containing nanostructures, methods of making medical devices containing nanostructures and methods of using medical devices containing nanostructures.

BACKGROUND OF THE INVENTION

Medical devices including, for example, intracorporeal or extracorporeal devices (e.g., catheters), temporary or permanent implants, stents, vascular grafts, anastomotic devices, aneurysm repair devices, embolic devices, and implantable devices (e.g., orthopedic or dental implants) are commonly infected with opportunistic bacteria and other infectious micro-organisms, in some cases necessitating the removal of implantable devices. Such infections can also result in illness, long hospital stays, or even death. The prevention of biofilm formation and infection on indwelling catheters, orthopedic implants, pacemakers, contact lenses, stents, vascular grafts, embolic devices, aneurysm repair devices and other medical devices is therefore highly desirous.

Enhancement of resistance of biomaterials to bacterial growth and promotion of rapid tissue integration and grafting of biomaterial surfaces are both areas of research. However, despite advances in sterilization and aseptic procedures as well as advances in biomaterials, bacterial and other microbial infection remains a serious issue in the use of medical implants. For example, greater than half of all nosocomial infections are caused by implanted medical devices. These infections are often the result of biofilms forming at the insertion site of the medical implant. Unfortunately, such infections are often resistant to innate immune system responses as well as to conventional antibiotic treatments. It will be appreciated that such infections are problematic not just in treatment of humans, but also in treatment of a number of other organisms as well.

A welcome addition to the art would be medical devices having enhanced surface areas and structures/devices comprising such, as well as methods of using enhanced area surfaces in medical devices. The current invention provides these and other benefits which will be apparent upon examination of the following.

SUMMARY OF THE INVENTION

The embodiments of the current invention comprise various medical devices, such as clamps, valves, intracorporeal or extracorporeal devices (e.g., catheters), temporary or permanent implants, stents, vascular grafts, anastomotic devices, aneurysm repair devices, embolic devices, and implantable devices (e.g., orthopedic and dental implants) and the like which comprise nanostructure enhanced surfaces. The nanostructures may comprise nanofibers (including nanowires), nanotubes or nanoparticles and/or combinations thereof, and including woven and nonwoven fibrous mats comprising nanofibers and nanotubes. The nanostructures may be coated or uncoated, or have multiple coatings thereon. The specific coatings are described herein and vary depending on the desired purpose of the device or method. Such enhanced surfaces provide many enhanced attributes to the medical devices in, on, or within which they are used including, e.g., to prevent/reduce bio-fouling, increase fluid flow due to hydrophobicity, increase adhesion, biointegration, etc.

In one aspect of the invention, a medical device is disclosed comprising a body structure having one or more surfaces having a plurality of nanostructured components associated therewith. The medical device may comprise an intracorporeal or extracorporeal device, a temporary or permanent implant, a stent, a vascular graft, an anastomotic device, an aneurysm repair device, an embolic device, an implantable device, a catheter, valve or other device which would benefit from a nanostructured surface according to the teachings of the present invention. The nanostructures may comprise nanofibers, nanotubes or nanoparticles and/or combinations thereof, and including woven and nonwoven fibrous mats comprising nanostructures. The nanostructures may be coated or uncoated, or have multiple coatings thereon. The specific coatings are described herein and vary depending on the desired purpose of the device or method.

The plurality of nanostructured components enhance one or more of adhesion, non-adhesion, friction, patency or biointegration of the device with one or more tissue surfaces of a body of a patient depending on the particular application of the device. The nanofibers (or other nanostructured components) on the surfaces of the medical device can optionally be wholly or partially coated with any number of materials including biocompatible polymers, which may be flowable (e.g., for injecting into the body). The polymer can protect the wires during insertion into the body of a patient, and then, in certain embodiments, can be soluble to expose the nanowires in situ for their intended application (e.g., adhesion, cellular integration, and the like). In one embodiment, the nanowires can be embedded (e.g., potted) in a plastic or polymer matrix material such as PTFE, and then the material can be partially etched or otherwise partially removed (either in situ or ex situ) such that the plastic or polymer matrix can protect most of the length of each nanofiber, leaving only portions of the nanowires such as their ends exposed for their desired intended application (e.g., adhesion, cellular integration, anti-bifouling etc.). Thus, for example, nanostructures such as nanotubes and nanowires can be easily applied to low melting temperature plastics and polymers for various medical device applications as described more fully herein. Polymer chains can be formed in situ in a dilute aqueous solution primarily consisting of a monomer and an oxidizing agent. In one embodiment the polymer is created in the solution and subsequently spontaneously adsorbed onto the nanofiber surfaces as a uniform, ultra-thin film of between approximately 10 to greater than 250 angstroms in thickness. UV initiated polymerization can also be used to perform polymerization or any other suitable method can be used as would be known in the art. In one preferred embodiment of the present invention nanofibers are coated with fibrinogen and/or fibrin, and there is a second coating comprising a biocompatible polymer thereon, e.g. for wound dressings.

The plurality of nanofibers or nanowires may comprise an average length, for example, of from about 1 micron to at least about 500 microns, from about 5 microns to at least about 150 microns, from about 10 microns to at least about 125 microns, or from about 50 microns to at least about 100 microns. The plurality of nanofibers or nanowires may comprise an average diameter, for example, of from about 5 nm to at least about 1 micron, from about 5 nm to at least about 500 nm, from about 20 nm to at least about 250 nm, from about 20 nm to at least about 200 nm, from about 40 nm to at least about 200 nm, from about 50 nm to at least about 150 nm, or from about 75 nm to at least about 100 nm. The plurality of nanofibers or nanowires may comprise an average density on the one or more surfaces of the medical device, for example, of from about 0.11 nanofibers per square micron to at least about 1000 nanofibers per square micron, from about 1 nanofiber per square micron to at least about 500 nanofibers per square micron, from about 10 nanofibers per square micron to at least about 250 nanofibers per square micron, or from about 50 nanofibers per square micron to at least about 100 nanofibers. per square micron. The plurality of nanofibers or nanowires may comprise a material independently selected from the group consisting of silicon, glass, quartz, metal and metal alloys, inorganic polymers including thermoplastics including but not limited to polyacrylonitriles(PAN), polyetherketones, polyimides, polyamides, thermoset plastics and organic polymers including proteins, TiO, ZnO, ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, PbS, PbSe, PbTe, AlS, AlP, AlSb, Ge, SiGe, SiO, $SiO_2$, silicon carbide, silicon nitride, or combinations thereof.

The nanofibers or nanowires may be attached to the one or more surfaces of the body structure of the medical device by growing the nanofibers or nanowires directly on the one or more surfaces, or the nanofibers or wires may be attached to the one or more surfaces of the body structure by attaching (e.g., via a covalent linkage) the nanofibers or nanowires to the one or more surfaces using one or more functional moieties. The body structure of the medical device may comprise a variety of materials, and the plurality of nanostructured components may optionally be incorporated into the material(s) of the body structure. The nanofibers (or other nanostructure) may be stiffened by sintering the fibers together. Additionally the nanostructures may be coated with a monomer that is subsequently polymerized (either in situ or ex situ) resulting in a structure having various porosities depending on the polymerization process. Additionaly the monomers/ and or polymers may be crosslinked The step of adding or coating the nanostructure with biocompatible polymers may be done prior to incorporating the nanofibers into the material of the body structure to provide enhanced rigidity and strength.

The medical device may further comprise one or more biologically compatible or bioactive coatings applied to the one or more nanostructured surfaces, and/or the nanofibers or nanowires may be incorporated into a matrix material (e.g., a polymer material) to provide greater durability for the fibers or wires.

In one embodiment of the invention there is contemplated coated nanostructures and composite coatings containing nanostructures therein. The composite coatings may be deposited on or formed on substrates including medical devices. In one embodiment the composite coatings comprise a matrix material and at least one nanostructure. A plurality of nanostructures, either the same or different, are preferred. Preferably the nanostructures comprise a material or have a material coated thereon or associated therewith having a biological function such as a nanoparticle comprising silver (Ag) or zinc (Zn) which possesses antibacterial properties. For example, the nanostructure may comprise Ag, or have Ag nanoparticles deposited (or coated or associated therewith) on a nanostructure. Preferably the matrix material comprises a biodegradable material such as $SiO_2$. The nanoparticles may be coated with multiple coatings if desired. The different layered coatings may serve different functions. As non-limiting examples, growh factors or peptides (for example BMP, VEGF, IKVAV) may be attached to nanowires. Bone morphogenic protenin may be added for bone integration. Vascular endothelial growth factor (VEGF) may be added for endothelialization. Peptide sequences such as IKVAV may be added to attach nerves and have those nerves express neuritis.

In one embodiment the nanowires comprise a silicon oxide and/or silicon dioxide shell. It is contemplated that the coating could comprise fired $CaCO_3$ or calcium polyphosphate with known bone integration properties.

In another aspect of the invention, a vascular stent is disclosed which comprises a plurality of nanostructured components associated with one or more surfaces of the stent. In another embodiment the stent has a nanostructure composite coating and/or nanostructured surface associated therewith. The nanostructures may comprise nanofibers, nanotubes or nanoparticles and/or combinations thereof, and including woven and nonwoven fibrous mats or mesh comprising nanostructures. The nanostructures associated therewith, including the fibrous mats may be coated or uncoated, or have multiple coatings thereon. The specific coatings are described herein and vary depending on the desired purpose of the device or method.

The plurality of nanofibers or nanowires may comprise a material independently selected from the group consisting of silicon, glass, quartz, metal and metal alloys, inorganic polymers and copolymers including thermoplastics including but not limited to polyacrylonitriles(PAN), polyetherketones, polyimides and polyamides, thermoset plastics and organic polymers including proteins, TiO, ZnO, ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, PbS, PbSe, PbTe, AlS, AlP, AlSb, Ge, SiGe, SiO, $SiO_2$, silicon carbide, silicon nitride. The nanofibers or nanowires and/or composite materials (including nanostructured surface) may be attached to the one or more surfaces of the stent by growing the nanofibers directly on the one or more surfaces, or, for example, by separately covalently attaching the nanofibers or nanowires to the one or more surfaces by using, e.g., one or more functional moieties or linkage chemistries. The stent may comprise a variety of materials selected from Nitinol, nickel alloy, tin alloy, stainless steel, cobalt, chromium, gold, polymers and/or copolymers or ceramics. The stent may comprise a drug compound that is directly adsorbed to the nanostructured surface or otherwise associated with the nanostructured surface (e.g., via covalent, ionic, van der Waals etc. attachment) via the use of one or more silane groups or other linkage chemistries. Addtionally, in one embodiment the nanostructure may comprise a nanotube having a composition such as a drug inside and/or outside the nanotube.

In another embodiment of the invention, an aneurysm repair device is disclosed which comprises a graft member (e.g., such as a patch or coil) which is configured to be positioned within a patient's body in a region of an aneurysm, the graft member comprising a plurality of nanostructured components associated with one or more surfaces of the graft member. The plurality of nanostructured components may comprise, for example, a plurality of nanofibers or nanowires. The plurality of nanofibers or nanowires may comprise a material independently selected from the group consisting of silicon, glass, quartz, metal and metal alloys, inorganic polymers and copolymers including thermoplastics including but not limited to polyacrylonitriles(PAN), polyetherketones, polyimides and polyamides, thermoset plastics and organic polymers including proteins, TiO, ZnO, ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, PbS, PbSe, PbTe, AlS, AlP, AlSb, Ge, SiGe, SiO, $SiO_2$, silicon carbide, silicon nitride. The nanofibers or nanowires may be attached to the one or more surfaces of the graft member by growing the nanofibers directly on the one or more surfaces, or the nanofibers or nanowires may be attached to the one or more surfaces of the graft member by attaching the nanofibers or nanowires to the one or more surfaces, e.g., via covalent, ionic, or other attachment mechanism. The graft member may comprise one or more of treated natural tissue, laboratory-engineered tissue, and synthetic polymer fabrics including without limitation a synthetic polymer selected from Dacron, Teflon, metal or alloy mesh, ceramic or glass fabrics. The graft member may comprise one or more biocompatible coatings applied to the one or more nanostructured surfaces of the graft member. In one embodiment, the graft member is configured to be positioned within an aorta of the patient in a region of an aneurysm.

The graft member may be configured to be positioned proximate to a side wall of a vessel that supplies blood to or from the brain in a region of an aneurysm.

In another embodiment the aneurysm repair device has a nanostructure composite coating and/or nanostructured surface associated therewith. The nanostructures may comprise nanofibers, nanotubes or nanoparticles and/or combinations thereof, and including woven and nonwoven fibrous mats or mesh made of nanofibers and nanotubes and/or having nanostructures thereon. The nanostructures associated therewith, including the fibrous mats may be coated or uncoated, or have multiple coatings thereon. The specific coatings are described herein and vary depending on the desired purpose of the device or method. In one particular embodiment, an aneurysm coil is disclosed having nanostructures associated therewith which is designed to be placed at the site of an aneurysm (e.g., in the brain) with the goal of inducing thrombogenesis. The resulting clot formed by the presence of the coil in the vessel would plug the vessel, eliminating the possibility that it could rupture. In contact with blood, the nanostructures (e.g., nanowires grown on the surface of the coil) would aid in clot formation by helping to induce a thrombogenic response in the vessel. Fibrin could also be coupled to the surface of the nanostructures to aid in clot formation. To overcome any potential physical or mechanical damage to the wires during insertion of the coil into the vessel at the site of the aneurysm, the nanosturctures can be encapsulated (potted) in a biodegradable polymer such as polylactic acid or polyglycolic acid or a mixture thereof. This would allow, for example, the nanostructures, grown on the coil, to be placed in the body without any appreciable damage.

In another embodiment of the invention, a medical device is disclosed for creating an anastamosis in a patient coupling a first vessel to a second vessel in an end-to-end or end-to-side anastomosis, the device comprising a tubular member comprising a plurality of nanostructured components associated with one or more surfaces of the tubular member. The plurality of nanostructured components may comprise, for example, a plurality of nanofibers or nanowires. The plurality of nanofibers or nanowires may comprise a material independently selected from the group consisting of silicon, glass, quartz, metal and metal alloys, inorganic polymers and copolymers including thermoplastics including but not limited to polyacrylonitriles(PAN), polyetherketones, polyimides and polyamides, thermoset plastics and organic polymers including proteins, TiO, ZnO, ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, PbS, PbSe, PbTe, AlS, AlP, AlSb, Ge, SiGe, SiO, $SiO_2$, silicon carbide, silicon nitride. The nanofibers or nanowires may be attached to the one or more surfaces of the tubular member by growing the nanofibers directly on the one or more surfaces or by attaching the nanofibers to the one or more surfaces, e.g., using covalent, ionic or other attachment means. The tubular member may comprise one or more of treated natural tissue, laboratory-engineered tissue, de-natured animal tissue, stainless steel, metal, alloys, ceramic or glass fabrics, polymers, plastic, silicone, and synthetic polymer fabrics. In one embodiment, the tubular member may comprise a T-tube for performing an end-to-side anastomosis or a straight tube for performing an end-to-end anastomosis. The tubular member may comprise one or more biocompatible or bioactive coatings applied to the one or more nanostructured surfaces of the tubular member. The tubular member can have a cross-sectional shape selected from circular, semi-circular, elliptical, and polygonal, for example.

In another embodiment the medical device has a nanostructure composite coating and/or nanostructured surface associated therewith. The nanostructures may comprise nanofibers, nanotubes or nanoparticles and/or combinations thereof, and including woven and nonwoven fibrous mats or mesh made of nanofibers and nanotubes and/or having nanostructures thereon. The nanostructures associated therewith, including the non-woven mesh and/or fibrous mats may be coated or uncoated, or have multiple coatings thereon. The specific coatings are described herein and vary depending on the desired purpose of the device or method.

In another embodiment of the invention, an implantable orthopedic device is disclosed which comprises a body structure comprising a plurality of nanostructured components associated with one or more surfaces of the body structure. The implantable orthopedic device may be selected from at least one of the following: total knee joints, total hip joints, ankle, elbow, wrist, and shoulder implants including those replacing or augmenting cartilage, long bone implants such as for fracture repair and external fixation of tibia, fibula, femur, radius, and ulna, spinal implants including fixation and fusion devices, maxillofacial implants including cranial bone fixation devices, artificial bone replacements, dental implants, orthopedic cements and glues comprised of polymers, resins, metals, alloys, plastics and combinations thereof, nails, screws, plates, fixator devices, wires and pins. The plurality of nanostructured components may comprise a plurality of nanofibers or nanowires, for example. The plurality of nanofibers or nanowires may comprise a material independently selected from the group consisting of silicon, glass, quartz, metal and metal alloys, inorganic polymers and copolymers including thermoplastics including but not limited to polyacrylonitriles(PAN), polyetherketones, polyimides and polyamides, thermoset plastics and organic polymers including proteins, TiO, ZnO, ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, PbS, PbSe, PbTe, AlS, AlP, AlSb, Ge, SiGe, SiO, $SiO_2$, silicon carbide, silicon nitride. The nanofibers or nanowires may be attached to the one or more surfaces of the body structure by growing the nanofibers directly on the one or more surfaces or by separately attaching (e.g., covalently, ionic ally, etc.) the nanofibers to the one or more surfaces. The body structure of the device may comprise one or more of treated natural tissue, laboratory-engineered tissue, de-natured animal tissue, stainless steel, metal, alloys, ceramic or glass fabrics, polymers, plastic, silicone, and synthetic polymer fabrics. The body structure may comprise one or more biocompatible or bioactive coatings applied to the one or more nanostructured surfaces of the body structure.

In another embodiment the orthopedic device has a nanostructure composite coating and/or nanostructured surface associated therewith. The nanostructures may comprise nanofibers, nanotubes or nanoparticles and/or combinations thereof, and including woven and nonwoven fibrous mats or mesh made of nanofibers and nanotubes and/or having nanostructures thereon. The nanostructures associated therewith, including the fibrous mats may be coated or uncoated, or have multiple coatings thereon. The specific coatings are described herein and vary depending on the desired purpose of the device or method.

In another embodiment of the invention, a bioengineered scaffold device for providing a scaffold for nerve regeneration is disclosed which comprises a base membrane or matrix having a plurality of nanostructured components associated therewith. The membrane or matrix may comprise one or more of the following materials: natural or synthetic polymers, electrically conducting polymers, conjugated polymers capable of electron transfer, electroluminescent polymersmetals, metal alloys, ceramics, glass or silicone. The plurality of nanostructured components may comprise nanowires, nanofibers, nanotubes and nanoparticles. The nanostructured surface of the membrane or matrix may be impregnated or bound with one or more drugs, cells, fibroblasts, nerve growth factors (NGF), cell seeding compounds, neurotrophic growth factors or genetically engineered cells producing such factors, VEGF, laminin or other drugs or substances to encourage axonal elongation and functional nerve performance.

In another aspect of the invention, a medical device for implantation in the uterus or fallopian tubes is disclosed which comprises a surface and a plurality of nanofibers or nanowires or mixtures thereof associated with the surface.

In another aspect of the invention, a medical device in which one or more surfaces are adapted to resist crystallization of body fluids is disclosed which comprises a surface and a plurality of nanofibers or nanowires associated with the surface.

In another embodiment of the invention, a medical device is disclosed in which one or more surfaces of the device are adapted to resist formation of thrombus and which comprises a surface and a plurality of nanofibers or nanowires.

In another embodiment of the invention, a medical device in which one or more surfaces are adapted to resist tissue in-growth is disclosed which comprises a surface and a plurality of nanofibers or nanowires associated with the surface wherein said nanofibers or nanowires are adapted to be hydrophobic.

Methods of use are also disclosed for treating patients with any one or more of the medical devices disclosed herein, which include, for example, a method of therapeutically treating a patient comprising contacting the patient with a medical device comprising a surface and plurality of nanofibers associated with the surface. Methods are disclosed for administering a drug compound to a body of a patient which comprises, for example, providing a drug-eluting device comprising at least one surface, a plurality of nanofibers and/or nanotubes associated with the surface, and a drug compound associated with the plurality of nanofibers and/or nanotubes; introducing the drug-eluting device into a body of a patient; and delivering the drug compound into the body of the patient. The drug-eluting device in one embodiment comprises a coronary stent, although any device which would benefit from local drug delivery at the site of disease (e.g., lesion) could be used in the methods of the invention. Where a coronary stent is used as the drug-eluting device, the drug compound may comprise paclitaxel or sirolimus, for example, or a variety of other medications including without limitation one or more of the following: anti-inflammatory immunomodulators such as Dexamethasone, M-prednisolone, Interferon, Leflunomide, Tacrolimus, Mizoribine, statins, Cyclosporine, Tranilast, and Biorest; antiproliferative compounds such as Taxol, Methotrexate, Actinomycin, Angiopeptin, Vincristine, Mitomycin, RestenASE, and PCNA ribozyme; migration inhibitors such as Batimastat, Prolyl hydroxylase inhibitors, Halofuginone, C-proteinase inhibitors, and Probucol; and compounds which promote healing and re-endothelialization such as VEGF, Estradiols, antibodies, NO donors, and BCP671. The drug compound may be adsorbed directly to the nanofiber and/or nanotubes surface, or the drug may be disposed inside the nanotube of the drug-eluting device or otherwise associated with it via the use of one or more silane groups, linker molecules or other covalent, ionic, van der Waals etc. attachment means. The nanofiber and/or surface may be configured such that the drug compound elutes slowly over time. This may be accomplished using time released coatings, for example. The plurality of nanofibers optionally are embedded in a biocompatible, non-thrombogenic polymer coating to provide enhanced durability to the nanofibers.

In other embodiments of the present invention, methods for enhancing osteoblast (or other cellular) functions on a surface of a medical device implant are disclosed which generally comprise providing a medical device implant comprising a plurality of nanowires thereon and exposing the medical device implant to osteoblast (or other cell type) cells. In one exemplary embodiment for increased cellular integration and adhesion, the nanowires may have an average length of from about 25 microns to at least about 100 microns and an average density on the nanostructured surface of from about 20 nanowires per square micron to at least about 100 nanowires per square micron. The plurality of nanowires may comprise a material independently selected from the group consisting of: silicon, glass, quartz, plastic, metal and metal alloys, polymers, TiO, ZnO, ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, PbS, PbSe, PbTe, AlS, AlP, AlSb, Ge, SiGe, SiO, $SiO_2$, silicon carbide, silicon nitride, polyacrylonitrile (PAN), polyetherketone, polyimide, an aromatic polymer, and an aliphatic polymer. The nanowires may be attached to the surface of the medical device implant by growing the nanowires directly on the surface, or by covalently or otherwise attaching the nanowires to the surface. The medical device implant may be selected from at least one of the following: total knee joints, total hip joints, ankle, elbow, wrist, and shoulder implants including those replacing or augmenting cartilage, long bone implants such as for fracture repair and external fixation of tibia, fibula, femur, radius, and ulna, spinal implants including fixation and fusion devices, maxillofacial implants including cranial bone fixation devices, artificial bone replacements, dental implants, orthopedic cements and glues comprised of polymers, resins, metals, alloys, plastics and combinations thereof, nails, screws, plates, fixator devices, wires, pins, and the like. The medical device implant may also contain one or more agent selected from the group consisting of anti-infective, hormones, analgesics, anti-inflammatory agents, growth factors, chemotherapeutic agents, anti-rejection agents, prostaglandins, RDG peptides, medicated coatings, drug-eluting coatings, drugs or other compounds, hydrophilic coatings, smoothing coatings, collagen coatings, and human cell seeding coatings.

These and other objects and features of the invention will become more fully apparent when the following detailed description is read in conjunction with the accompanying claims.

BRIEF DESCRIPTION OF THE DRAWINGS

FIG. 2A is an illustration of a Prior Art stent and stent delivery catheter.

FIG. 2B shows placement of the stent of FIG. 2A at the site of a lesion in a vessel of a patient such as a coronary artery.

FIGS. 12I-P show SEM images of osteoblasts adhered on nanowire surfaces after 1 week (FIGS. 12I-J), 2 weeks (FIGS. 12K-L), 3 weeks (FIGS. 12M-N) and 4 weeks (FIGS. 12O-P);

DETAILED DESCRIPTION

Figure 1:
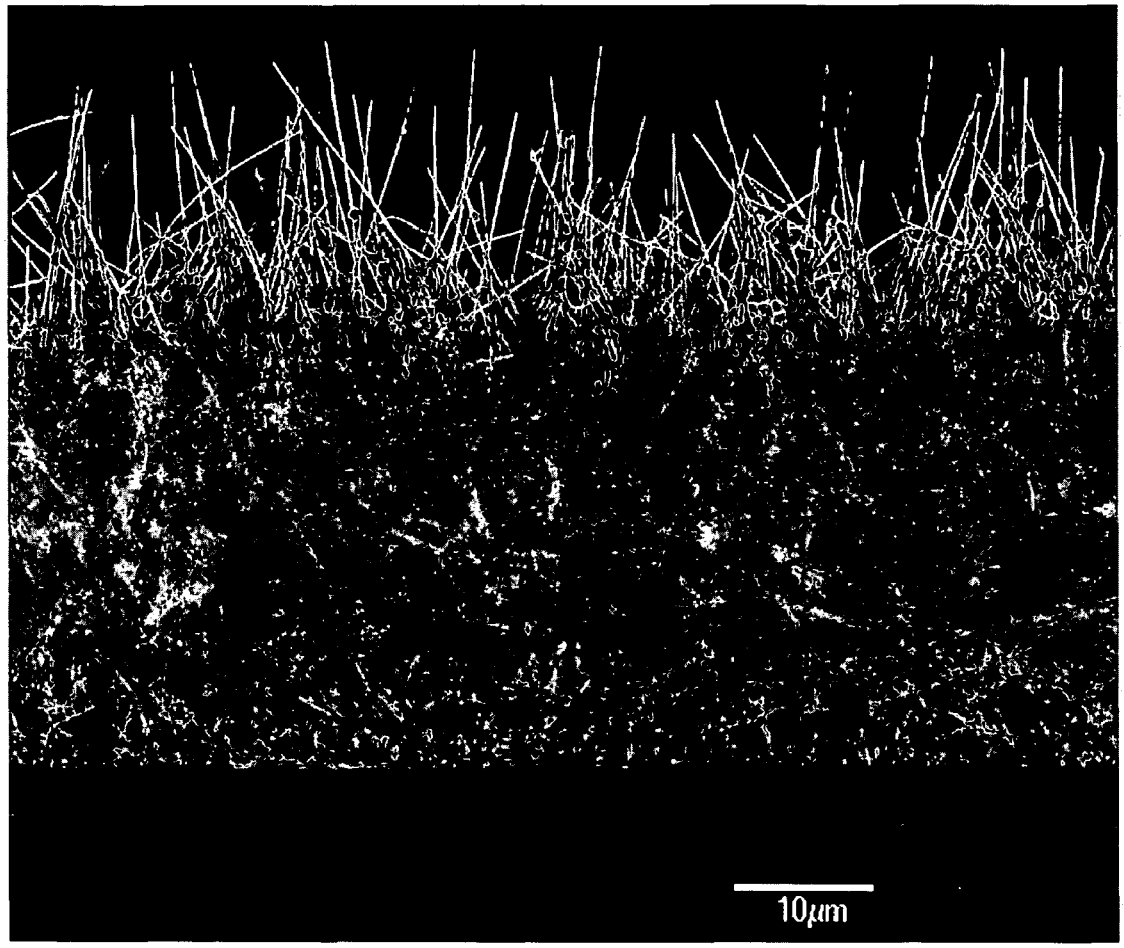
FIG. 1 displays a photomicrograph of an exemplary adherent nanofiber structure of the invention.

It should be appreciated that specific embodiments and illustrations herein of uses or devices, etc., which comprise nanofiber enhanced surface areas should not be construed as limiting. In other words, the current invention is illustrated by the descriptions herein, but is not constrained by individual specifics of the descriptions unless specifically stated. The embodiments are illustrative of various uses/applications of the enhanced surface area nanofiber surfaces and constructs thereof. Again, the enumeration of specific embodiments herein is not to be taken as limiting on other uses/applications which comprise the enhanced surface area nanofiber structures of the current invention. fibronectin, collagen, RGD containing peptides and other cell binding motifs As seen in FIG. 1, the nanofibers optionally form a complex three-dimensional structure on the medical device surfaces to which they are applied. Again, it will be appreciated that in other embodiments of the invention, the nanofibers are more uniform in height, conformation, etc. The degree of such complexity depends in part upon, e.g., the length of the nanofibers, the diameter of the nanofibers, the length:diameter aspect ratio of the nanofibers, moieties (if any) attached to the nanofibers, and the growth conditions of the nanofibers, etc. The bending, interlacing, etc. of nanofibers, Which help affect the degree of intimate contact with a secondary surface, are optionally manipulated through, e.g., control of the number of nanofibers per unit area as well as through the diameter of the nanofibers, the length and the composition of the nanofibers, etc. Thus, it will be appreciated that the bio-utility of the nanofiber substrates herein is optionally controlled through manipulation of these and other parameters. The nanofibers (or other nanomaterial) may be stiffened by sintering the fibers together (or otherwise cross-linking the fibers, e.g., by chemical means) prior to or after incorporating the nanofibers into or onto the material of the body structure to provide enhanced rigidity and strength.

It also will be appreciated that nanofibers can, in optional embodiments, curve or curl, etc., thus, presenting increased surface area for contact between the nanofibers and the substrate surfaces involved. The increased intimate contact, due to multiple touchings of a nanofiber with a second surface, increases the van der Waals attractions, friction forces, or other similar forces of adhesion/interaction between the nanofiber and the second substrate. For example, a single curling nanofiber can optionally make intimate contact with a second substrate a number of times. Of course, in some optional embodiments, a nanofiber can even retouch the first surface if it curls/curves from the second surface back to the first surface. Due to possible multiple contact points (or even larger contact points, e.g., when a curved nanofiber presents a larger intimate contact area than just its tip diameter, e.g., if a side length of a nanofiber touches a substrate surface) between a single nanofiber and a second substrate/surface, the intimate contact area from curled/curved nanofibers can be greater in some instances than when the nanofibers tend not to curl or curve (i.e., and therefore typically present a "straight" aspect to the second surface). Therefore, in some, but not all, embodiments herein, the nanofibers of the invention comprise bent, curved, or even curled forms. As can be appreciated, if a single nanofiber snakes or coils over a surface (but is still just a single fiber per unit area bound to a first surface), the fiber can still provide multiple, intimate contact points, each optionally with a relatively high contact area, with a secondary surface.

I) Nanofiber Surfaces as Bacteriostatic, Hydrophobic & Antithrombotic Catheter Lumens Catheters are widely used in medical applications, e.g., for intravenous, arterial, peritoneal, pleural, intrathecal, subdural, urological, synovial, gynecological, percutaneous, gastrointestinal, abscess drains, and subcutaneous applications. Intravenous infusions are used for introducing fluids, nutrition, blood or its products, and medications to patients. These catheters are placed for short-term, intermediate, and long-term usage. Types of catheters include standard IV, peripherally inserted central catheters (PICC)/midline, central venous catheters (CVC), angiographic catheters, guide catheters, feeding tubes, endoscopy catheters, Foley catheters, drainage catheters, and needles. Catheter complications include phlebitis, localized infection and thrombosis.

Intravenous therapy is a critical element in the treatment of patients. One out of eight persons will undergo intravenous therapy of some form annually in the United States. Today, infusion therapy is almost routine. In hospitals, 90 percent of surgical patients and a third of non-surgical inpatients receive some form of intravenous therapy. American medical device manufacturers dominate the catheter industry, producing 70 to 80 percent of the catheters used around the world. In 1997, worldwide sales of catheter products totaled approximately $7.3 billion, and is growing at a healthy pace of 10.4% annually. The largest segment, however, is the renal market, which is comprised primarily of urinary catheters and dialysis catheters. It is currently a $4 billion segment, and is expected to reach $7.1 billion soon.

The best-known urology catheters are Foley catheters, which have been commercially available since the 1930s. These catheters and others, both internal and external condom-type catheters, are used for incontinence, for dying patients, and often for bladder drainage following surgery or an incapacitating injury or illness. These relatively easy-to-use catheters are used throughout the world in hospitals, nursing homes, and home-care settings. There are two types of dialysis catheters: hemodialysis and peritoneal. End users for this catheter segment are vascular surgeons and interventional radiologists, although once long-term catheter ports are in place, nephrologists monitor access sites and catheter-based dialysis treatments.

Therefore, in various embodiments herein, nanofiber enhanced surfaces are used in, on or within material surfaces to construct catheters and related medical devices. The bacteriostatic characteristics of the nanofiber surface catheters herein can optionally decrease infection, while the hydrophobic characteristics can optionally increase fluid flow properties. The anti-thrombotic characteristics of such devices can optionally decrease thrombosis which leads to catheter plugging and emboli. Catheter manufacturers desire improvement of catheter materials and catheter design to make them more biocompatible, and to offer better infection control. However, in spite of progress, infection at present has remained a major problem. Use of nanofiber enhanced surfaces in construction of catheters, however, can optionally aid with such concerns.

The performance advantage of catheter lumens with decreased infection, increased flow and decreased clot formation arising from use of nanofiber enhanced surfaces are features of the invention. Such features can optionally lead to reduction in catheter complications and an increase in the amount of time a catheter could remain in place before having to be replaced (as a result of using the nanofiber coated catheter lumens).

Catheters are optionally placed anywhere in the body (i.e., the class of catheters comprises more than just IVs) and are typically plastic, which is strong enough to place in, e.g., a vein, but flexible enough to bend within the patient's body. It is typically desired to reduce catheter care (e.g., replacement time) and to decrease catheter contamination, e.g., from skin "crawling down," biofouling, etc. It is also desirable to avoid phlebosis or any problem disturbing flow which can arise through use of a "flush" to blow clots, etc. downstream. The current embodiments avoid such because they are inherently antibacterial, hydrophobic and antithrombogenic.

The antifouling aspects of the current invention are also optionally useful in catheters used for wound drainage. Such catheters typically present problems with bacterial contamination, etc. Use of the embodiments of the invention can, thus, reduce drug use (e.g., antibiotics), reduce pain, reduce need for further operations, and reduce infection rates. As explained herein the catheters of the invention are also optionally coated with compounds, e.g., silver compounds, titanium oxides, antibiotics, etc. which can further help in reducing infection, and that may help in the formation of antibodies, etc.

II) Nanofiber Enhanced Surfaces in Disposable Surgical Retractors Dental Retractors and Placement Devices.

Retractors and forceps are commonly used in surgery to position or move (e.g., manipulate) organs and tissues for better visualization, surgical approach, and placement of implants. Dentistry commonly uses forceps to position small tooth restorations (e.g., crowns, inlays, on lays, veneers, implants/implant abutments, etc.) and position gingival tissues in a variety of periodontal, oral surgical and endodontic procedures. The current existing dental device in this market sector is a sticky ended probe (Grabits™) that is disliked by dentists as it is non-sterile, cannot adhere to living tissue and is difficult to release from the implant it is adhered to.

The high traction forces generated at minimal pressures by nanofiber enhanced surfaces can optionally create minimal tissue damage in surgical organ movement and retraction. The high traction forces generated at small point loads can optionally allow for increased dental surgical control and placement of dental restorations. The advantage of a sterilizable probe that attaches to living tissue as well as inert implants is thought to provide significant advantage over existing technology.

The performance a dvantage, increased surgical speed and decreased tissue damage over toothed and crushing (serrated) forceps emphasizes the benefits of the current invention. Reduction in post surgery tissue trauma and consequent inflammation accompanied by an increase in healing rate are expected to arise as a result of using the nanofiber coated retractors herein, thus allowing for ease of use, increased speed of dental surgery, and security of handling implants.

Some embodiments of the invention comprise disposable retractors having nanofiber enhanced surfaces. Additionally, other embodiments involve, e.g., upside down pyramid shapes (e.g., 1 cm in height). The points of such pyramids can be used to touch nerves, etc. Also, the flat sizes can be used for larger objects, while the edges can be used for still other differently sized objects. Retractors of the invention can optionally come in a variety of sizes and shapes depending upon the specific intended use. Again, for example, in dentistry a retractor of the invention can be used for handling and placement of crowns, etc.

III) Enhanced Traction in Laparoscopy Clips Arising Through Use of Nanofiber Enhanced Surfaces.

Termination clips are applied laparoscopically during gallbladder surgery. About 10 clips come integrated in a $60.00 disposable cartridge. Five or six clips are typically used to seal off arteries and veins during gallbladder surgery. The small U shaped clips, about the size of a staple, are made of titanium and are crimped in place. They do not have a tractive surface and rely on the crimping force to stay in place. Trauma caused by the clip can cause the growth of adhesions or a cut in the vessel.

The high traction forces generated at minimal pressures by the nanofiber surfaces of the invention would make such clips ideal for laparoscopic surgery, as well as for other surgeries.

The performance advantage of a significantly higher traction surface (~2x) from the nanofiber enhanced devices herein would be highly desirable. This is true especially because there are about 600,000 gallbladder removals a year in the United States alone. If other laparoscopic surgeries such as appendix removals were added in this number would grow to more then 1,000,000. If one $60 cartridge is used per surgery the market is at least $60,000,00.

Other applications of such clips or clamps can be to, e.g., clip or clamp the aorta, use as atraumatic clamps, etc. Such clamps are also expected to be useful in beating heart surgery to help stabilize heart motion. Such products optionally comprise arms with pads (with nanofibers, etc.). Eye and/or eyelid surgery also desires such clamps to stabilize the eye. Yet other common surgical uses include, e.g., retracting dura for opening scalp, holding pericardium in heart surgery, holding skin grafts in place, holding organs/tissues in place, etc. Yet other embodiments comprise wherein the substrate is dissolvable, e.g., liver sock, etc.

Surgeries often deal with organs, etc. that are slimy, slippery, delicate, etc. Also, while anatomical elements that are tubular or sheet-like can be grasped with suturers, etc., more irregularly shaped organs (e.g., liver, heart, etc.) are more problematic. Thus, retractors, disposable sleeves, and universal contact surfaces for myriad clamp types which comprise nanofiber surfaces are all desired. They can help eliminate constant repositioning of medical devices (e.g., point retractors can touch a tissue and hold it until release is needed). The devices of the invention also can find placement in laparoscopic devices and stabilization pads.

IV) External Fixator Implant Bacteriostatic Surfacing

External fixators are pins and wires inserted through the skin into bone for the purpose of healing bone fractures. These pins and wires are then connected externally with rods and clamps in order to provide rigidity and stability so the fractured bone can heal. The advantage of these devices over internally placed plates, screws, pins and cerclage wires is in the decreased amount of tissue and vascular disruption caused when compared to surgical placement of internal implants. This lesser surgical invasion allows the fracture to heal much faster and with lesser muscle and subcutaneous scarring, implant-related osteosarcomas, osteoarthritic changes, or painful cold-sensation complications and obviates the need of surgical implant removal at a later date. There has been a move over the past ten years towards this "biologic" orthopedic method of healing over internal implants. Minimization of tissue damage reduces healing time which is paramount in bone healing. Complications arising from the use of external fixators are bacterial infection from the skin, and excessive movement of the pins if the connecting apparatus is insufficiently stable. The use of the nanofiber bacteriostatic surfacing is expected to decrease or eliminate what is perceived as the major of these two problems.

The nanofiber coated bacteriostatic stainless surface of external fixators would decrease the degree of skin surface bacterial communication and subsequent contamination of the threaded pin insertion, bone interface which causes pin loosening and fracture healing failure. The performance advantage of a bacteriostatic, externally placed bone pin would undoubtedly be desired especially to reduce post surgery infection and pin loosening complications. In various embodiments, all of the implanted material is coated with nanofibers. In other embodiments, screw threads, pins, and/or bonds are nanofiber coated. Other embodiments comprise nanofiber coating of the bottom of a plate and the top of a screw head, flexible wires (e.g., k-wires, k-pins, etc.), straight pins, etc. It will be appreciated that such external fixators of the invention are also optionally used in limb-lengthening procedures.

V) Butterfly Skin Bandage/Patch

Many skin lacerations are clean wounds in need of simple surface closure if suturing is unavailable or unnecessary. Currently available butterfly skin bandages function well, but fail rapidly as adhesion decreases with movement of skin and hydration at the bandage site. A hydrophobic adhesive butterfly bandage comprising nanofiber surfaces would be an elegant solution to this need.

Corneal abrasions are a common ophthalmic injury causing blepharospasm, ciliary spasm and pain. The majority of these lesions take 24-72 hours to heal. Corneal ulcers take 3-5 days to heal. Treatment with mydriatics which block ciliary spasm, reduce pain in the ciliary body but increase photophobia. The patients are hence more comfortable in dark environments. The use of a dermal adhesive, hydrophobic butterfly patch comprising nanofiber surfaces to close the eyelids would solve the photophobia problem and increase the rate of corneal healing due to increased bathing of the cornea with lachrymal secretions under a closed palpebrum.

The high traction forces generated at minimal pressures, and hydrophobic characteristics would make nanofiber coated flexible butterfly skin patches ideal for closing skin wounds and eyelids. In some embodiments, the adhesive device is flesh colored, or allows patients to bathe without the device loosening. Such devices help patients avoid surgery and avoid "puckers" at end of sutures (especially important for plastic surgery). Other advantages of such devices include, e.g., no curing of the adhesion needed, a good splinting material, not plaster that would need to be wet, etc., the device can be "breathable" when, e.g., the nanofibers are on a mesh material, etc. Such devices can also optionally comprise drugs or the like to be released transdermally (either continuous, concomitant with a rise in temperature, etc.). Such devices are also optionally used with decabitous ulcers, in venostatis situations (in diabetic patients, pressure on the skin and bone causes erosion and ulcer). In addition, such a wound dressing device can be coupled with a moiety, such that the moiety can enhance wound healing (e.g., cell growth). Nanofiber dimensions on the bandage can be designed to capture cells.

VI) Enhanced Traction Clamping Devices for Cardiac Surgery

Clamps are used extensively in cardiac surgery to temporarily stop blood flow. There has been a move over the past ten years towards disposable rubber atraumatic clamp inserts that reduce arterial damage compared to traditional steel jawed clamps. Mininimization of damage reduces recovery time and complications due to scarring. Rubber inserts have made inroads into the market but their limited traction still requires clamping forces high enough to damage many arteries. The high traction forces generated at minimal pressures by the devices herein would make nanofiber coated clamp inserts ideal for cardiac surgery. The performance advantage of a significantly higher traction surface (~2x) would undoubtedly be desired, e.g., to reduce post surgery complications.

VII) Adhesive Hydrophobic Otic Plug

Tympanic punctures, lacerations or rupture from infection are a common nuisance to patients when showering and swimming. Mechanical ear plugs are uncomfortable and often leak causing vestibulitis (loss of balance) and otitis media (inner ear infection). Reengineered otic plugs using nanofiber surface adhesion properties in combination with hydrophobic characteristics is expected to provide a significant improvement for millions of patients with open tympanums. The high traction forces generated at minimal pressures would make nanofiber coated and hydrophobic coated ear plugs more comfortable and form a better seal against water entry than existing technologies. The performance advantage of a significantly higher traction surface (~2x) would be desired, especially to reduce post otitis media complications and vestibulitis.

The hydrophobic action and traction of the nanofibers would be expected to create a secure plug. In various embodiments, the plug fits within the ear canal, while in other embodiments, it comprises a cap or disk to cover the ear or ear canal. Similar embodiments are optionally used for other meati or orifices (e.g., to prevent nose bleeds, etc.). In some embodiments, the nanofibers release from their substrate backing, e.g., to remain behind on the patient so as to, e.g., not remove a scab or clot. Other embodiments can optionally include anti-biofouling properties and/or anti-microbial properties. See below. Some embodiments are expected to optionally be used for urinary plugs, and the like. For example some embodiments can optionally be used for fallopian tube obstruction to prevent pregnancy.

VIII) Surgical Adhesion Preventative

Post-operative adhesions are a common surgical complication. Presently, and historically, there has been a great deal of activity to develop methods for the prevention of post-operative adhesions. Some of the approaches, e.g., the ingestion of iron powder-laced oatmeal followed by the application of magnets to the abdomen to jostle the bowel and prevent adhesions, are interesting approaches. Adhesions are particularly troublesome in a variety of locations, e.g., between the pericardium and sternum following open heart surgery, in the abdominal cavity following bowel procedures and, especially, in the retroperitoneal space involved with gynecological reconstruction. Two primary approaches have been explored. The first involves implantable barrier films prepared, for example, from hyaluronic acid or hydrogonic acid or oxidized cellulose, but has not met with success because the location of where to place the film to prevent adhesions is not determinable. The second approach involves the instillation of a bolus of solution, e.g., N,O-acetylchitosan, to wet the general area where adhesions might be expected. This seems to be the superior therapeutic direction, but no satisfactory product along this line has been commercialized. If a suitable, proven product were made available, it would have the potential to be used prophylactically in practically every surgical procedure. It should be noted that post-operative adhesions usually form during the first post-operative week and, if not formed during this time, they usually do not occur. Therefore, the task is to prevent fibroblasts (which produce the collagenous adhesions) to adhere to local tissue surfaces because, without cellular attachment during the first week, adhesions will not form. The anti-adhesion solutions of the current invention are expected to prevent such cell attachment. The anti-adhesion embodiments herein are optionally in various forms (e.g., liquid application forms, film application forms, etc.). Creation of adhesions are especially bad for fertility surgery. Because adhesions form relatively quickly, it is desired to avoid fibroblast for 5 days post operations.

An aqueous microcapsule or particle suspension prepared from an absorbable natural (e.g., collagen) or synthetic (e.g., polyglycolic acid) polymer and coated with a nanofiber surface to provide extreme lubricity is a feature of the invention. About 200 ml of this suspension could be poured into the appropriate cavity and would coat the tissue with a surface not hospitable to fibroblast cell attachment and subsequent adhesion formation. The material would be harmlessly absorbed after a few weeks. Some embodiments can optionally be a mesh (e.g., synthetic, metal, fabric) coated with nanofibers or nanowires that is laid directly over the cavity.

IX) Endoscopes and Catheters

One of the more difficult aspects of endoscopy, e.g., colonoscopy, involves the frictional resistance of the device passing through the tubular organ, e.g., bowel, urethra, esophagus, trachea, blood vessel, etc. Besides being difficult to transport the scope or catheter, the friction causes significant discomfort to the patient. Slippery catheters, coated with, for example, polyvinylpyrrolidone have been designed to provide easier passage but these devices have not enjoyed wide market acceptance. A lubricious scope or catheter comprising nanofiber surfaces of the invention, would be expected to provide significantly increased patient comfort and well as more facile transport for the physician.

X) Intraluminal Cameras

One of the latest diagnostic advances is the use of miniaturized, untethered cameras to observe internal organs. Such cameras, the size of pills, may be ingested or injected and float downstream, sending images back to the medical observer. It is expected that improved lubricity due to nanofiber surfaces of the invention will enhance the performance of such devices. An appropriate nanofiber coating is expected to make it easier for the camera to be ingested and manipulated along its path. Other similar embodiments comprise nanofiber coatings on devices to, e.g., create hydrophobic shields (e.g., windows) on devices such as cameras, keep a coating layer (e.g., hyluonic acid, etc.) on a device, to create a transparent coating on contact lenses (which optionally also helps prevent protein build-up), etc.

XI) Mechanical Heart Valves

There are two types of heart valve prostheses used for replacement of aortic and mitral valves. Mechanical valves commonly are metallic cages with a disc that opens at systole to allow blood to flow and closes at diastole to prevent backflow. These valves last indefinitely but require the daily administration of an anticoagulant drug to prevent thrombotic complications. The dose must be carefully regulated to prevent thrombus formation on one hand and internal hemorrhage on the other. The other type of valve is the tissue valve, sometimes isolated en bloc from porcine hearts and sometimes constructed from bovine pericardial tissue. These leaflet valves are more like natural valves and usually do not require anticoagulant drug administration. However, they are susceptible to degradation and have more finite life expectancies than do the mechanical valves. Fortunately, they fail slowly and provide ample time for surgical replacement. It would be of inestimable medical advantage if the long lasting mechanical valves could function successfully without anticoagulation therapy. Nanofiber enhanced surfaces of the invention used thusly are part of the invention. Additionally, nanofiber surfaces also can be used in the improvement of the hemodynamic performance of left ventricular assist devices (LVADs).

With nanofiber specially designed mechanical heart valves, it is expected that: there will be improved hemodynamics resulting from laminar flow; there will be improved blood throughput per systole; the need for anticoagulation will be eliminated or significantly reduced; the incidence of thrombosis will be eliminated or significantly reduced; and the level of hemolysis will be reduced or eliminated.

XII) Small Caliber Vascular Grafts

Presently, a variety of vascular prostheses larger than about 6 mm in diameter perform adequately when implanted from the thoracic aorta through the iliac/femoral regions. Below about 6 mm in diameter, such grafts fail when implanted either as interpositional or bypass grafts, secondary to full lumen thrombosis. Similarly, there is no graft material available for venous reconstruction. For many years, workers have tried to develop a small diameter vascular graft, particularly for coronary artery bypass procedures, to avoid the need to harvest saphenous veins from the leg. Generally, small diameter grafts in the 2-5 mm range fail because a 0.5-1.0 mm thick layer of protein is rapidly deposited on the luminal surface causing a further reduction in luminal diameter which, in turn, induces the formation of mural thrombi. Even conventionally non-wettable surfaces such as polytetrafluoroethylene (Teflon®) and polyurethanes do not resist protein intimal layering.

The ultra non-wettability of nanofiber enhanced surfaces may affect two factors of extreme importance. First, the avoidance of deposition of plasma protein on the luminal surface will preserve the original graft diameter. Equally important, a nanofiber surface may provide close to ideal laminar blood flow which would be expected to reduce or entirely eliminate luminal thrombus formation. This is optionally of great importance in preventing graft thrombosis and/or minimizing anastomotic intimal hyperplasia, well-know causes of graft failure secondary to turbulent flow, particularly at the sutured anastomosis.

Specifically, the nanofiber surface may be beneficially employed for the following grafts: femoral/popliteal (and infrapopliteal) reconstruction; coronary bypass grafts (possibly replacing saphenous veins and IMA procedures); A-V shunts (hemodialysis access); microvascular reconstruction (e.g., hand surgery); and vein reconstruction. Use of such for A-C bypass grafts and for peripheral vascular reconstruction, especially in the diabetic patient population, are contemplated. Microvascular and A-V shunt and vein uses are also contemplated. More detailed descriptions of the use of nanofiber enhanced surfaces for sutureless anastomotic procedures is described further below.

XIII) Bulking Agent for Cosmesis

The Collagen bulking business has taken off in the arena of cosmesis with ~800,000 procedures thought to be performed in 2003. The annual revenues of the space for the materials provider(s) is closing in on $500 Million. The primary issue with Collagen when used for cosmesis (e.g., lips and deep wrinkles, etc.) is durability. The typical collagen bulking injection will last ~3-4 months prior to subsidence of results and need for reapplication. Thus, non-resorbable, yet biocompatible micro-spheres are desired to create a durable cosmetic effect.

The ability to create non-bioburden micro-spheres injectable through a standard gauge needle, is greatly desired in this area, especially if: they are easily applied, injectable and lubricous enough for easy placement; there are durable results; there are no biocompatibility issues; and there is no migration over time. There are reasons to believe that the ability to combine an optimized lubricity (e.g., through balancing hydrophobia & hydrophilia with nanofibers) in conjunction with a non-bioburden technology on a micro-sphere carrier could create a competitive winner. Other embodiments comprise possible reduction of scar tissue and those having erodable polymers with nanofiber scaffold which is optionally functionalized.

XIV) Enhanced Flow and Reduced Thrombogenicity Mechanical Heart Valve

Replacement valve implantation is a large and valuable market that is approaching $1 Billion in sales. First, there has been an on-going pendulum swing between mechanical and tissue valve implantation driven primarily by the real and perceived differences between the two in the areas of longevity, thrombogenicity and flow dynamics. Second, product based competition has ossified as new product development cycles have been protracted on the back of ever more rigorous regulatory/clinical requirements. With the possibility of modifying existing products (resulting in a much shorter regulatory path) potentially delivering improvements in 2 of the key valve metrics (thrombogenicity and fluid dynamics), nanofibers could potentially have a dramatic impact upon the market share within mechanical valve players and between mechanical and tissue valve products.

Although not entirely understood, thrombogenicity and flow dynamics are interrelated issues. In fact, the flow eddies created downstream of the hinge seat for the most popular bi-leaflet valve design is still blamed for much of the thrombogenic effect of such products. A hydrophobic surface coating such as that made possible by nanofiber enhanced surfaces may have dramatic effect in reducing such problems.

This embodiment of the invention offers the benefit of being an addendum to a current product thereby allowing a dramatically reduced cycle time while at the same time delivering true product based differential advantage.

XV) More Durable Functionality of Implantable Sensors and Pacing Leads

The implantable sensor market is in its infancy with the variety of early applications including; glucose sensors, cardiac function sensors (either on-lead or off) and neurological implants of various stripes. Many of these companies have similar problems associated with bio-fouling over time and the difficulty of creating durable reagent beds. It may be possible that the combination of reagent doping pads, arranged in concert with highly hydrophobic structures will deliver a significantly longer lasting functionality to sensors of all types. Current technologies are either accepting this shortcoming (e.g., glucose sensors limited to 3 days of functionality) or are combating it with costly and difficult to engineer solutions involving mechanically active packaging and/or massive parallelization.

A further and related application for the nanofibers herein would be the coating of pacing leads to provide both a better electrical contact with tissue and a non-fouling shaft. Much of the sensor/reagent technology employed in these markets is no longer proprietary due to the long mature run in traditional non-implant diagnostics and the packaging may in-fact be the critical proprietary technology that enables the space. How does one package a sensor (be it reagent or electrical) for long term survival in the highly corrosive and actively encapsulating environment of the human body. This is a significant challenge for all of the indwelling companies. The uniquely non-fouling approach delivered by the nanofibers herein, has the additional property that it leaves no-imprint down-stream or in proximity to the non-fouling surface. This would enable a creative packaging with reagent/sensors to garner accurate readings. Furthermore, with reagent durability being of concern, it may be possible to create reagent doped pads comprising nanofibers in much the same way as the drug doped pads discussed in the drug-eluting stent summary below.

Nanowires having a PN junction along their length or at an end are useful for electrical stimulation. The present invention contemplates that the nanowires disclosed herein have those properties. Synthesis techniques for those wires is known in the art, for example, in U.S. Pat. No. 6,882,051, where nanowires were produced wherein the doping and/or composition of the nanowires was controlled in either the longitudinal or radial direction, or in both directions. Segments of heterostructures can be various materials, including, for example, semiconductor materials which are doped or intrinsic and arranged to form a variety of junctions such as pn, pnp, npn, pin, pip and so forth. Also, various other doping techniques are known. For example, Lieber et al, WO-A-03/005450, disclose nanowires wherein different wires were doped with opposite conductivity type dopants, and two wires of opposite conductivity type were physically crossed, one on top of the other, so that a pn junction was formed at their point of contact. Also, various other doping techniques are known. One technique that is valuable with heterojunctions is known as modulation doping. In this technique, carriers from a doped layer of, e.g., AlGaAs, diffuse across an interface with an undoped material, e.g., GaAs, and form a very thin layer of carriers of very high mobility, within a potential well, next to the interface—see for example FIG. 1 of WO 02/19436. U.S. Pat. No. 5,362,972 discloses an FET wherein the current flowpath between source and drain is composed of GaAs nanowhiskers. The nanowhiskers are surrounded by n-doped AlGaAs, to create by modulation doping a one-dimensional electronic gas within each nanowhisker. WO 02/020820 discloses a modulation doping technique in coaxial heterostructure nanowires, wherein dopants in an outer coaxial layer donate free carriers to an inner nanowire. The contents of the above patents are hereby incorporated by reference in their entirety.

In the arena of pace-maker leads, there are two issues that bother the clinicians involved. The occasional dislodged or poorly placed lead that delivers inadequate charge to the tissue and the over-growth of tissue around the leads over time that can, in some patients who have had multiple leads placed over time, actually cause flow resistance. These can further complicate subsequent procedures/surgeries. Further, abandoned but not removed leads can cause complications. Such devices comprising nanofibers herein could likely remove both of these issues with nanofibers on the sensor head and an anti-bio-fouling coating along the shaft. The present invention contemplates nanowires in accordance with various embodiments of the present invention capped with an electrically conducting material for use as pace-maker leads.

Glucose sensors: The holy grail of the ~$2 Billion worldwide glucose sensing market has been to get away from the finger-stick devices and into a sustained glucose device either through a truly non-invasive approach or an indwelling approach. The two paths remain in fundamental technological competition with neither approach yet showing a clear edge in embodiment or time-to-market over the other. The implantable glucose sensing technologies under development today all bring with them substantial enough limitations so as not to be considered for broad market adoption. While this cannot be said of the non-invasive approaches they face hurdles in development that have for 15 years stymied the market leaders in their quest for workable units. Nanofiber addition to such sensors would prevent/ameliorate several problems listed above.

Cardio Sensors: In its very earliest stages this market promises to provide full cardiac output metrics without the need for an interventional cardiological procedure (perhaps on an on-going basis as an alert) and/or to provide superior real-time control of an active cardiology device (e.g., BV-Pacer, left ventricular assist device (LVAD)). Again, addition of nanofibers to such devices would prevent/ameliorate many problems above.

Neuro sensors/emitters: Again, another early stage space but in this case the primary focus in the area of stimulation as opposed to sensing. Neuromodulation and neurostimulation rely on consistent, uninterrupted contact with nervous tissue. Nanofibers on the tissue contact end of the leads can secure the lead and prevent scar formation (e.g., glial scar) leading to improved conduction. Additionally, nanofibers can be used as conductive materials in the shaft of the lead.

ICD and Pacemaker leads: The numbers in the combined market are large in unit volume with ~1,000,000 implantations per year. This is further experiencing growth as bi-ventricular pacing has taken off even more rapidly than the all ready optimistic projections. The issue with the leads has been that while they, at one time, took quite a large share of the value chain their price-point has been steadily eroded.

Nanofibers on the ICD and pacemaker leads help to create a high surface-to-volume ratio on the lead surface to help secure the lead in place and further to provide improved mechanical and electrical connectivity to the tissue surface. For example, it has been demonstrated that semiconductor nanofibers (e.g., silicon nanowires) often grow nearly normal (e.g., vertical) to the surface of a (111)-oriented Si wafer and make good electrical and mechanical connection to the substrate. See, e.g., Islam M. S. et al., *Ultahigh-density silicon nanobridges formed between two vertical silicon surfaces*, Nanotechnology 15 (2004) L5-L8; Tan Q et al., *Materials Research Society Fall Mtg.* (Boston, Mass., December 2002) (Paper F6.9), the entire contents of which are each incorporated by reference herein. By depositing nanofibers (e.g., nanowires) directly on ICD and pacemaker lead surfaces, the nanofibers can provide enhanced electrical connectivity between the ICD and pacemaker lead and the tissue surface (e.g., heart tissue) to which it is attached. Thus, the use of nanofiber enhanced surfaces is attractive for ICD and pacemaker leads, sensors and other medical device applications requiring electrical (and mechanical) conduction including bone, nerve and muscle stimulation and the like. In some embodiments, nanowires in accordance with the present have PN junctions which are useful for tissue electrostimulation. In addition, the high surface-to-volume ratio created by the nanostructured surface allows for the continued miniaturization of ICD and pacemaker leads, sensors and the like due to the enhanced area of electrical contact to thereby achieve improved size reductions comparable to conventional devices. Nanowires having electrically conducting tips are useful for this purpose.

XVI) Vascular Stents and Next Generation Drug Eluting Coronary Stents

Vascular stents are small metallic devices which are used to keep the blood vessels open following balloon angioplasty. The development of coronary stents, for example, has revolutionized the practice of interventional cardiology over the past 10 years. More than 70 coronary stents have been approved in Europe and over 20 stents are commercially available in the United States such as the Multi-Link Vision™ Coronary Stent System available commercially from Guidant Corporation (Indianapolis, Ind.), and the Driver™ Coronary Stent System or BeStent2™ available commercially from Medtronic; Inc. (Minneapolis, Minn.).

Figure 2C:
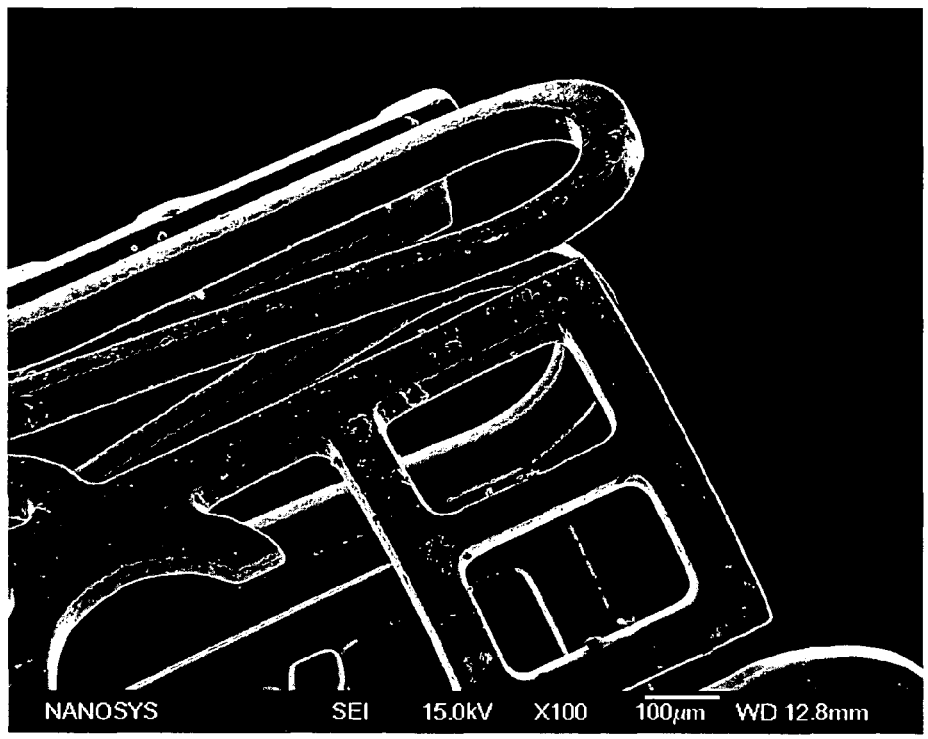
FIG. 2C displays a photomicrograph of a vascular stent prior to deposition of a nanostructured surface on the stent.

Commercially available stents can take a variety of forms. For example, one such stent 210, as shown, for example, in FIGS. 2A-B, is a stainless steel wire which is expanded by balloon dilatation. The stent 210 may be crimped onto a balloon 212, as shown in FIG. 2A, for delivery to the affected region 214 of a vessel 216 such as a coronary artery. For the sake of simplicity, the multiple layers of the vessel wall 216 are shown as a single layer, although it will be understood by those skilled in the art that the lesion typically is a plaque deposit within the intima of the vessel 216.

One suitable balloon for delivery of the stent 210 is the Maverick® PTCA balloon commercially available from Boston Scientific Corporation (Natick, Mass.). The stent-carrying balloon 212 is then advanced to the affected area and across the lesion 214 in a conventional manner, such as by use of a guide wire and a guide catheter 205. A suitable guide wire is the 0.014" Forte™ manufactured by Boston Scientific Corp. and a suitable guiding catheter is the ET 0.76 lumen guide catheter.

Once the balloon 212 is in place across the lesion 214, as shown in FIG. 2A, the balloon 212 may be inflated, again substantially in a conventional manner. In selecting a balloon, it is helpful to ensure that the balloon will provide radially uniform inflation so that the stent 210 will expand equally along each of the peaks. The inflation of the balloon 212 causes the expansion of the stent 210 from its crimped configuration to its expanded position shown in FIG. 2B. The amount of inflation, and commensurate amount of expansion of the stent 210, may be varied as dictated by the lesion itself.

Following inflation of the balloon 212 and expansion of the stent 210 within the vessel 216, the balloon is deflated and removed. The exterior wall of the vessel 216 returns to its original shape through elastic recoil. The stent 210, however, remains in its expanded form within the vessel, and prevents further restenosis of the vessel. The stent maintains an open passageway through the vessel, as shown in FIG. 2B, so long as the tendency toward restenosis is not greater than the mechanical strength of the stent 210.

Another form of stent is a self-expanding stent device, such as those made of Nitinol. The stent is exposed at the implantation site and allowed to self expand.

Significant difficulties have been encountered with all prior art stents. Each has its percentage of thrombosis, restenosis and tissue in-growth, as well as varying degrees of difficulty in deployment. Another difficulty with at least some of the prior art stents is that they do not readily conform to the vessel shape. Anticoagulants have historically been required at least for the first three months after placement.

Thus there has been a long felt need for a stent which is effective to maintain a vessel open, without resulting in significant thrombosis, which may be easily delivered to the affected area and easily conformed to the affected vessel.

Figure 2D:
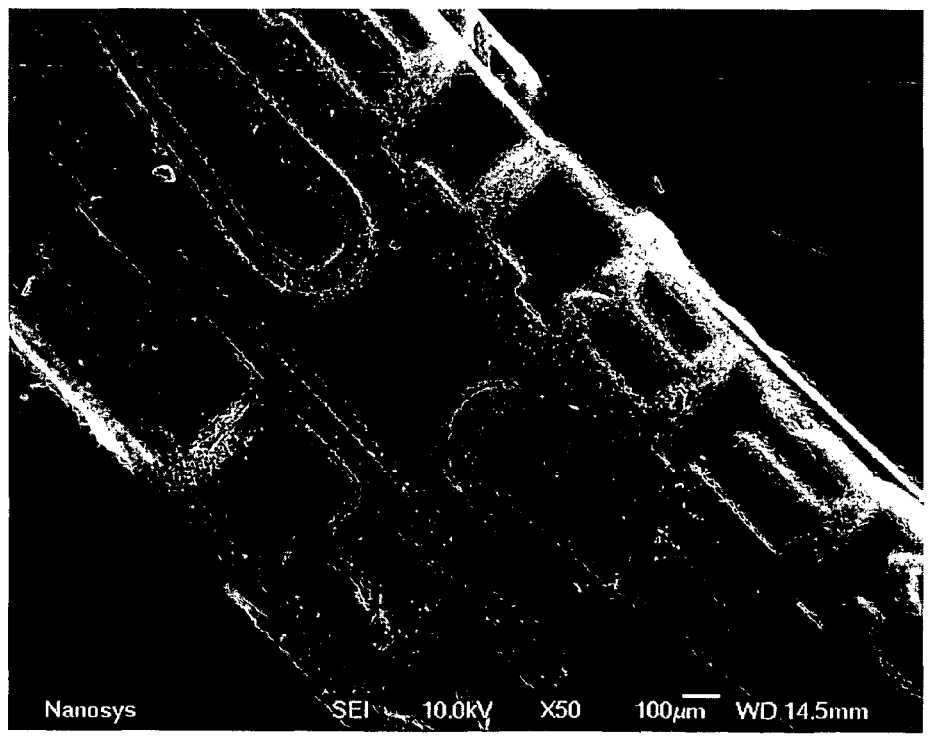
FIG. 2D displays a photomicrograph of a vascular stent following growth of a plurality of nanofibers on the exposed surfaces of the stent.

The present embodiment of the invention is generally directed to endovascular support devices (e.g., commonly referred to as "stents") that are employed to enhance and support existing passages, channels, conduits, or the like, and particularly animal, and particularly mammalian or human lumens, e.g., vasculature or other conductive organs. In particular, in one embodiment the invention provides such stent devices that employ nanostructured components as shown, for example, in FIG. 1 and FIG. 2D, to enhance the interaction of the stent with the passages in which they are used. Typically, such nanostructured surfaces are employed to improve adhesion, friction, biointegration or other properties of the device to enhance its patency in the subject passage. Such enhanced interactivity is generally provided by providing a nanostructured surface that interacts with the surface of the passage, e.g., an inner or outer wall surface, to promote integration therewith or attachment thereto. The nanostructured components (e.g., nanofibers) can either be attached to the outer or inner surface of the stent, e.g., by growing the nanofibers directly on the outer and/or inner surface of the stent, or by separately covalently or ionically attaching the fibers to the stent surfaces. In addition, the nanofibers or other nanostructures can be embedded into the stent material itself to enhance the rigidity and strength of the stent within the vessel into which it is inserted. The shape and size of the nanofibers as well as their density on the graft surfaces can be varied to tune the adhesive (or other) properties of the stent to the desired levels. In particularly preferred aspects, higher aspect ratio nanofibers are used as the nanostructures. Examples of such nanofibers include polymeric nanofibers, metallic nanofibers and semiconductor nanofibers as described previously.

In another embodiment of the present invention there is contemplated stents having composite coatings of a nanostructure and a matrix as disclosed herein.

In another embodiment of the present invention there is contemplated hollow nanotubes and nanowires coated and functionalized as set forth herein associated with stents.

The stents of this invention may also be coated on the inside and/or outside with other materials to still further enhance their bio-utility. Examples of suitable coatings are medicated coatings, drug-eluting coatings (as described below), hydrophilic coatings, smoothing coatings, collagen coatings, human cell seeding coatings, etc. The above-described nanofiber coatings on the stent can provide a high surface area that helps the stent to retain these coatings. The coatings can be adsorbed directly to the nanostructured surface of the stent. Alternatively, the nanostructured surface may be provided with a linking agent which is capable of forming a link to the nanostructure components (e.g., nanofibers) as well as to the coating material which is applied thereto. In such cases, the coating may be directly linked to the nanostructured surface, e.g., through silane groups, or it may be coupled via linker binding groups or other appropriate chemical reactive groups to participate in linkage chemistries (derivitization) with linking agents such as, e.g., substituted silanes, diacetylenes, acrylates, acrylamides, vinyl, styryls, silicon oxide, boron oxide, phosphorus oxide, N-(3-aminopropyl)3-mercaptobenzamide, 3-aminopropyl-trimethoxysilane, 3-mercaptopropyl-trimethoxysilane, 3-maleimidopropyl-trimethoxysilane, 3-hydrazidopropyl-trimethoxysilane, hydroxysuccinimides, maleimides, haloacetyls, pyridyl disulfides, hydrazines, ethyldiethylamino propylcarbodiimide, and/or the like.

There are known in the art drug eluting coronary stents, such as the U.S. FDA-approved Cordis Cypher™ sirolimus-eluting stent and the Boston Scientific Taxus™ paclitaxel-eluting stent system. Drug eluting stents are rapidly gaining market share and may become the standard of care in coronary revascularization by the year 2005. This new therapy involves coating the outer aspect of a standard coronary stent with a thin polymer containing medication that can prevent the formation of scar tissue at the site of coronary intervention. Examples of the medications on the currently available stents are sirolimus and paclitaxel, as well as anti-inflammatory immunomodulators such as Dexamethasone, M-prednisolone, Interferon, Leflunomide, Tacrolimus, Mizoribine, statins, Cyclosporine, Tranilast, and Biorest; antiproliferative compounds such as Taxol, Methotrexate, Actinomycin, Angiopeptin, Vincristine, Mitomycin, RestenASE, and PCNA ribozyme; migration inhibitors such as Batimastat, Prolyl hydroxylase inhibitors, Halofuginone, C-proteinase inhibitors, and Probucol; and compounds which promote healing and re-endothelialization such as VEGF, Estradiols, antibodies, NO donors, BCP671, and the like. Sirolimus, for example, had been used previously to prevent rejection following organ transplantation. Unfortunately, the use of polymer coatings on stents can lead to thrombosis and other complications; anticoagulants are typically required at least for the first three months after placement to alleviate some of these issues.

However, the provision of a nanostructured surface on these newer stents according to the teachings of the present invention can eliminate the need for such polymer coatings and thus minimize some of these complications. Increasing surface area (e.g., through spring coil, micropockets, etc.) through nanofibers is quite desirable. Thus, nanofibers are optionally embedded/empended into tissue to give a more sustained benefit and better drug release. The nanofiber surfaces give greatly enhanced surface area and a longer length of elution and a more intense concentration. The drugs can be directly tethered (e.g., via silane groups) to the nanofibers (or other nanostructured components) or can be linked (e.g., covalently) to the nanofibers through suitable linkage chemistries such as those described above. The linkage chemistry can be tailored to provide for customized drug elution profiles and for the controlled release of the drug compounds over time.

The manufacturers of drug eluting stents are very interested in the several facets of this new technology: increased contact surface area between coated metal and arterial wall; increased depth/durability of coating for pro-longed elution times; and intriguing possibilities of multiple, layers of differing drugs for novel elution profiles. The basic stent structure (conformity, ease of deployment, branching utilization, etc.) still matters a great deal in winning doctors over from other products.

By developing a coating that enables increased contact area and "dose density", that likely can be applied to any and all existing stents, the nanofiber devices herein can pursue a variety of market strategies, e.g., through improved fluid dynamics with a hydrophobic surface coating on the inside, drug elution improvement, etc. By applying a nanofiber coating to the outside surface of the stent it may be possible to then have a thicker and more durable drug coating on the stent than would be possible without the nanofiber technology. Furthermore, the high surface area contact intrinsic to the nanofiber technology may yield improvements in tissue response to the attached drug. Furthermore, the present invention contemplates applying a hydrophobic coating to the inside of the stent to improve flow dynamics—particularly within small arteries.

In addition to coronary stents, the use of nanostructured surfaces may also be beneficially applied to other stents which are used in other parts of the body of a patient, such as urethral and biliary stents. In these body lumens, it is desired to prevent crystallization on the struts of the stents. In the biliary tree, for example, bilirubin crystals deposit on foreign surfaces such as sutures and permanent or temporary stents. Such deposition typically decreases the useful life of the stents and can require patients to undergo multiple procedures for successful therapies. A similar situation exists in the urinary tract. Uric acid precipitates on stents and leads to "stent encrustation," which ultimately leads to device failure. Stents otherwise may be a promising therapy for conditions such as Benign Prostatic Hyperplasia (BPH). A stent with a super hydrophobic nanofiber coating would resist crystal formation because the aqueous phase would not "see" the stent and crystal inducing elements would not have a chance to deposit.

XVII) Small Caliber Vascular Grafts

Presently, a variety of vascular prostheses larger than about 6 mm in diameter perform adequately when implanted from the thoracic aorta through the iliac/femoral regions. Below about 6 mm in diameter, such grafts fail when implanted either as interpositional or bypass grafts, secondary to full lumen thrombosis. Similarly, there is no graft material available for venous reconstruction. For many years, workers have tried to develop a small diameter vascular graft, particularly for coronary artery bypass procedures, to avoid the need to harvest saphenous veins from the leg. Generally, small diameter grafts in the 2-5 mm range fail because a 0.5-1.0 mm thick layer of protein rapidly is deposited on the luminal surface causing a further reduction in luminal diameter which, in turn, induces the formation of mural thrombi. Even conventionally non-wettable surfaces such as polytetrafluoroethylene (Teflon®) and polyurethanes do not resist protein intimal layering. The peripheral vascular market represents a huge, relatively untapped market because of the limitations of small diameter grafts. The nanofiber surfaces herein can aid in reducing bio-fouling, increasing hydrophobicity, etc.

It is suggested that the ultra non-wettability (hydrophobicity) of nanofiber surfaces may affect two factors of extreme importance. First, the avoidance of deposition of plasma protein on the luminal surface will preserve the original graft diameter. Equally important, a nanofiber surface can optionally provide close to ideal laminar blood flow which would be expected to reduce or entirely eliminate luminal thrombus formation. This may be of great importance in preventing graft thrombosis and/or minimizing anastomotic intimal hyperplasia, well-known causes of graft failure secondary to turbulent flow, particularly at the sutured anastomosis.

The nanofiber surface may be beneficially employed for the following grafts: Femoral/popliteal (and below the knee) revascularization; Coronary bypass grafts (possibly replacing saphenous veins and IMA procedures); A-V shunts (hemodialysis access); Cranial (Supra Temporal Artery/Medial Cerebral Artery [STA/MCA]); Microvascular reconstruction (e.g., hand surgery); vein reconstruction By far, coronary bypass grafts have significant medical and commercial value followed by femoral revascularization. In some embodiments the graft material is simply coated with nanofibers herein, while others comprise entirely new substrates specifically designed for nanofiber coating. A nanofiber A-C bypass graft would be quite desirable, particularly if it could be implanted using advanced least invasive surgical procedures to avoid splitting the sternum. A large market exists for peripheral reconstruction, especially in the diabetic patient population. The microvascular, A-V shunt and vein markets are relatively small but together, may be form a significant business. There is potential to carry the vascular graft business into an entirely new level of performance.

Current grafts in small vessels present problems. Current choices include, e.g., Dacron fabric, PTTFE (similar to Gortex), etc. Problems can arise with small diameters and protein layers that are put down (especially true for diameters under 6 mm). Ideal grafts want the vessel to look like a wet noodle for impeding into vein structures and not have film forming. Thus, prevention of protein buildup and perfection of laminar flow in the vessel is desired. Also, less invasive procedures are desired. The current nanofiber devices can optionally fulfill these needs, e.g., be less invasive because devices could be preloaded and, e.g., stapled into the vessel. The hydrophobicity of various embodiments herein can be quite useful in typical uses. The grafts herein are optionally temporary or permanent within the patient. Other embodiments include wherein the nanofiber grafts also comprise drug coatings, etc. (e.g., heparin, etc.).

Other embodiments deal with concerns of, e.g., working with collagen spun vascular grafts. Also, host vessel sutured to a graft can get puckered at interface from sutures, thus, leading to eddies at interface. Thrombus can form at interface and intimal hyperplasia can lead to vessel narrowing at the anastomotic site. Such can cause narrowing of the vessels until the vessel closes down. This is not usually a problem in large vessels, but can be quite problematic in smaller vessels. Therefore, nanofiber surfaces of the invention can be incorporated into grafts at such interfaces. Also, coated spiral structures which are optionally removed are incorporated herein. Sutures, staples, etc. are also optionally nanofiber enhanced.

Other embodiments include nanofiber enhancement with, e.g., blood treatment, left ventricular assist devices (LVAD) treatment regimes (e.g., preventing thrombosis), patent foramen ovale (PFO), atrial septal defects (ASDs), treatment of left atrium aneurysms, treatment of diabetic small vessel disease (i.e., instead of amputation), treatment of venous thrombosis (e.g., over long term, etc.). The nanofiber surfaces herein typically provide longevity, can allow flexibility, provide strength of holding staple/suture. They can be used in, e.g., growth of specific cells for wound healing, as scaffolding for bone growth to occur, etc. For example, with respect to atrial septal defects, when there is a large hole between the right and left atria, oxygen rich blood leaks back to the right side of the heart. The result can be pulmonary hypertension. These defects are often treated surgically, through open heart surgery. A device that could be placed percutaneously, and permanently close the hole, would be desirable over the morbidity associated with open chest surgery. A device incorporating nanofibers can be placed via a catheter through the arterial system, and serve as a patch or plug over or in the defect.

XVIII) Timed Release Nanowire Balls

The past 20 years has seen many research efforts aimed at orally delivered targeted delivery drug vehicles. Specificity, controlled release and low toxicity have been difficult hurdles to overcome and most of these efforts are still in the research phase. Polymers, dendrimers, liposomes and antibodies are four well-studied drug carriers. These structures range from the micron size to several nanometers. The larger particles tend to stick to the desired tissue and then the drug erodes out; the smaller structures often carry only several drug molecules and work on contact or when a bond is broken to the carrier structure (dendrimers). Nanostructures could span this size range from small dots (3-10 nm) to clusters of nanowires (20-500 nm). These structures could be readily conjugated to drug molecules and can be dispersed in aqueous solution.

High drug capacity and ease of functionalization are typical advantages of the current invention. Typical embodiments are chosen based upon, e.g., toxicity testing for patient application, as well as nanofiber accumulation. Some embodiments comprise tericoated tabs and can depend on pH values in the stomach, e.g., for time release due to recognition of an enzyme or the proper pH. Other embodiments comprise air-filled nanofiber balls, e.g., as contrast agents in ultrasound and the like, or drug encapsulated, biodegradable spheres. Also, PEGylated liposomes not taken up by the reticuloendothelial system (RES) are provided. Another advantage of the use of nanofiber surfaces for drug release balls or capsules is that the adherent properties of the nanofiber surfaces can cause attachment of the surface of the drug-release structure to, for example, the mucosal membrane so they might adhere sublingually or in the esophageal pathway prior to exposure to the stomach (or other targheted organ) leading to the precise delivery of drugs over a controlled (e.g., prolonged) period.

XIX) Surgical Needles

Some embodiments herein comprise nanofiber coated surgical needles. Cutting needles are better when serrated. When passing a needle through tissue, the apparent sharpness is based on resistance (correlated to dullness). Protein attaching to the surface of such needles gives the apparent dullness. Thus, coatings (e.g., as with nanofibers) can be more important than "sharpness" of the needles. Such concepts are also applicable to scalpels, etc.

XX) Wound Dressing

Wound dressings are used extensively in trauma, at catheter skin-sites and post surgical applications. This is a very competitive field with an excess of OTC and ethical supply products available. Minimization of infection, allowance of air penetration, adhesion ability, water repellency, ease of application, ease of removal are all important characteristics that influence physician, nurse and patient product preference. All of these characteristics can be found in separate wound dressings but not as an "all-in-one" package. A flexible, breathable, hydrophobic, bacteriostatic sided dressing with an adhesive, bacteriostatic backside would be revolutionary to the medical field. The current nanofiber surfaces herein can optionally supply many or all of such characteristics. This dressing would be able to access ethical as well as OTC markets.

The combination of nanowire coated characteristics would allow patients to shower or bathe, avoid infection, heal, and decrease the need for painful bandage changes. Various embodiments can comprise bacteriostatic dressings and/or bactericidal dressings. Various embodiments can comprise silver and/or zinc and/or titanium oxides. Such dressings are especially contemplated for, e.g., burn victims, etc.

The current invention comprises a number of different embodiments focused on nanofiber enhanced area surface substrates and uses thereof (e.g., in medical devices/uses). As will be apparent upon examination of the present specification and claims, substrates having such enhanced surface areas present improved and unique aspects that are beneficial in a wide variety of applications for medical use. It will be appreciated that enhanced surface areas herein are sometimes labeled as "nanofiber enhanced surface areas" or "NFS" or, alternatively depending upon context, as "nanowire enhanced surface areas" or "NWS."

A common factor in the embodiments is the special morphology of nanofiber surfaces (typically silicon oxide nanowires herein, but also encompassing other compositions and forms) which are optionally functionalized with one or more moietys.

Fibrin is a protein involved in the clotting of blood. It is a fibrillar protein that is polymerised to form a "mesh" that in situ, forms a haemostatic plug or clot (in conjunction with platelets) over a wound site. Naturally, fibrin is made from its zymogen fibrinogen, a soluble plasma glycoprotein that is synthesised by the liver. Processes in the coagulation cascade activate the zymogen prothrombin to the serine protease thrombin, which is responsible for converting fibrinogen into fibrin. Fibrin is then cross linked by factor XIII to form a clot. Fibrinogen is a 340-KD glycoprotein synthesised in the liver hepatocytes and megakaryocytes, which normally has a concentration between 1.5-4.0 g/L (normally measured using the Clauss method) in blood plasma. Dysfunction or disease of the liver can lead to a decrease in fibrinogen production or the production of abnormal fibrinogen molecules with reduced activity (dysfibrinogenaemia). Hereditary abnormalities of fibrinogen (the gene is carried on chromosome 4) are of both quantitative and qualitative in nature and include; afibrinogenaemia, hypofibrinogenaemia, dysfibrinogenaemia, and hypodysfibrinogenaemia. In its natural form, fibrinogen is useful in forming bridges between platelets, by binding to their GpIIb/IIIa surface membrane proteins; though fibrinogen's major use is as a precursor to fibrin. Fibrinogen is a symmetrical dimer composed of 6 paired polypeptide chains. (alpha, beta, and gamma chains). On the alpha and beta chains, there is a small peptide sequence (called a fibrinopeptide). It is these small peptides that prevent fibrinogen spontaneously forming polymers with itself. Following the activation of prothrombin to thrombin (Factor IIa). Thrombin cleaves fibrinopeptide A off the alpha chain and reveals a site in the E domain that can bind to the carboxy terminal end of the gamma chain. Beta chain cleavage occurs more slowly and contributes to the fibril and fiber associations of fibrinogen. These processes convert fibrinogen to fibrin. The active molecules of fibrin stack up on each other, usually incorporating (by trapping) aggregates of platelets and molecules of thrombin. The soluble fibrin molecules are later cross-linked (by factor XIII) with covalent bonds, to form a stable hemostatic plug, thus effectively stopping bleeding.

In one embodiment of the present invention there is contemplated a wound dressing comprising nanostructures (which may be nanotubes, nanowires or nanoparticles) coated with fibrin and/or fibrinogen dispersed in a pharmaceutically acceptable carrier. Optionally the fibrin coated nanostructures may be wholly or partially encapsulated in a biocompatible polymer such as such as polyglycolic acid (PLG), poly-L-lactic acid (PLA), poly-DL-lactic acid, poly-D-lactic acid, poly(lactic acid-glycolic acid) copolymer (PLGA), poly-.epsilon.-caprolactone, poly(glycolic acid-caprolactone) copolymer (PGCL), polyamino acid, polyanhydride, polyorthoester, poly(L-lactic acid), polycaprolactone, poly (lactide-co-glycolide), poly(hydroxybutyrate), poly(hydroxybutyrate-co-valerate), polydioxanone, poly(glycolic acid-co-trimethylene carbonate), polyphosphoester, polyphosphoester urethane, cyanoacrylates, poly(trimethylene carbonate), poly(iminocarbonate), polyalkylene oxalates, polyphosphazenes and biomolecules such as cellulose, starch, collagen and hyaluronic acid. and copolymers and mixtures thereof. It is preferable to use a hydoxy acid which is accepted by the Food and Drug Administration (FDA) and has been used as a biodegradable polymer which can be used in a human body.

In another embodiment of the present invention the nanostructures may be associated with a structure or substrate such as a medical device such as an implant or fibrous web. The size of the structure or substrate may be varied depending on the desired end use. As non-limiting examples, nanowires or nanotubes may be made into an interwoven web or fibrous matt. Fibrinogen may be attached to the nanowires or nanotubes. The wound dressing of the present invention may be made to have gecko adhesive properties as disclosed herein.

In another embodiment of the present invention the nanowires or nanotubes may be formed into a fused network by sintering and used as a wound dressing. One of skill in the art will appreciate the conditions necessary for sintering the different materials comprising the nanostructures without destroying the integrity of the nanowire or nanotube.

In another embodiment of the present invention the wound dressings may be formed from bioscaffolds or VECM as disclosed herein.

XXI) Abdominal (or Thoracic) Aortic Aneurysm (AAA) Medical Procedures

The compositions, apparatus, systems and methods described herein relating to nanostructured surface enhanced coatings can be used, for example, to assist in the device, function and deployment of prostheses during the repair of thoracic or abdominal aortic aneurysms.

An aortic aneurysm generally is an abnormal widening, stretching or ballooning of the thoracic or abdominal portion of the aorta, which is the major artery from the heart which delivers blood to the major organs of the body. The thoracic and abdominal portions of the aorta represent the upper, arched portion and lower, abdominal portion of the aorta, respectively. The exact cause of aneurysm is unknown, but risks include atherosclerosis and hypertension. A common complication is ruptured aortic aneurysm, a medical emergency in which the aneurysm breaks open, resulting in profuse bleeding. Aortic dissection occurs when the lining of the artery tears and blood leaks into the wall of the artery. An aneurysm that dissects is at even greater risk of rupture. Aortic aneurysms occur in approximately 5-7% of people over the age of 60 in the United States alone. Over 15,000 people die each year of ruptured aneurysm, the $13^{th}$ leading cause of death in the U.S.

Generally, when an abdominal or thoracic aortic aneurysm reaches a size of about 5 cm, surgical intervention is necessary. To repair an abdominal or thoracic aortic aneurysm by intraoperative procedure, the thoracic cavity can be accessed by a midline or retroperitoneal incision in the case of an open procedure, or by percutaneous access in a minimally invasive endograft procedure, and an autogenous or prosthetic graft is used to isolate the aneurysm from blood flow and pressurization, thus precluding aneurysm expansion and minimizing the risk of rupture. Typically, the first choice for replacement is typically the autogenous saphenous vein (ASV), but when it is unavailable for transplant, artificial prosthetic grafts may be used. Generally they are used for large diameter vessel applications such as aortic aneurysm repair, however recent research efforts have been directed towards finding suitable methods for medium and small diameter vessel repair as well.

Within the aorta, the endo-graft is under the relentless force of pulsatile blood (approximately 10N of force during the maximum of the heart rhythm. The area where blood enters (proximal neck) and exits (distal neck) the aneurysm along its path from the heart to the iliacs is the area where adhesion (fixation) and tissue integration (seal) of the device occurs. The fixation force is related to the hoop force of the endo-graft (how much spring tension the device can apply radially toward the aorta walls), and the limit of what the aorta can support without damage.

Nitinol™, which is a shape memory alloy of approximately 50/50 Ni and Ti, has been specifically engineered to produce hoop forces that are very stable over time and not in excess of what the aorta can handle. An optimized Nitinol™ endo-graft can provide approximately 10N of frictional force—approximately the same as the down-stream force of blood through the endo-graft. This tight balance between forces means that even a slightly sub-optimal placement of the endo-graft can result in devastating failures over time as migration forces cause the endo-graft to move along the aorta.

Many parameters can adversely the impact fixation force and/or increase migration force, such as the physical dimensions of the aneurysm and device as well as orientation of the aorta at the location of fixation. Generally, long necks are required in order to get high fixation forces. Additionally, migration force increases as a function of device diameter. Another key parameter is the angle of the aneurysm with respect to the aorta, with angles greater than 40 degrees resulting in a rapid decrease in fixation force. Ancillary patient conditions such as hypertension can also reduce fixation.

The prior art has attempted to improve fixation with barbs or hooks built into the graft (Zenith endo-graft by Cook and Excluder endo-graft by W. L. Gore are examples). The clinical outcome of this suprarenal fixation approach is still unclear and potentially does long term damage to the arteries that feed the kidneys since the barbs/hooks attach at the intersection of the renal artery and aorta. While this approach is the most promising so far, 4 yr mortality rates appear to be no different with or without barbs or hooks. Recently the prior art contemplates the use of chemical adhesives to fix the endo-graft in place. A monomer is injected around a placed endo-graft, followed by in-situ polymerization, potentially resulting in greater fixation and seal. While it is still too early to know the long-term success of this approach, there are general concerns that, as is inherent will all polymeric system, residual monomer and leachable components may be an issue for long term biological compatibility.

Overall, the current EVAR technology is ill-suited to addressing the full aortic aneurysm patient population. Currently, more than 70% of all diagnosed abdominal aortic aneurysm (AAA) are ineligible for EVAR because of the risk of migration is too high. Patients who do undergo EVAR require costly and repeated monitoring to ensure that migration or endoleak is not occurring. In addition, even for those patients who do receive EVAR treatment, while 30 day mortality rates are substantially improved, 4 yr mortality rates appear to be no different than for traditional bypass surgery, primarily due to migration and endo-leak occurring over time.

Further, inaccurate deployment of aortic prostheses can lead to inadequate sealing of the aneurysm which can cause further aneurysm expansion due to blood flow around the graft, and/or inadvertent blockage of collateral vessels supplied by the aorta, for example, such as the renal arteries. Aortic prostheses can also slip out of position. To date, as noted below, at least two stent grafts have been pulled from the market due to high rate of failure, and others continue to fail. A need exists to improve the outcome of aortic aneurysm repair by improving the materials of the grafts to make them more adherent thereby minimizing or eliminating failures of conventional devices caused by such complications as leakage and/or mal-positioning or slippage of the prosthetic devices.

Using the methods and compositions of the present invention, both open and minimally invasive endovascular repair procedures can be performed to ensure that an aortic prosthesis, when placed properly at the site of an aneurysm, will adhere firmly to the tissue surface and maintain its patency for longer periods of time than conventional devices. The outer (and/or inner) diameter of the graft prosthesis is coated with nanofibers (or other nanostructured material such as nanotetrapods, nanotubes, nanowires, nanodots, etc.) either by directly growing the nanofibers on the surface of the graft, or by coating the graft with harvested nanofibers, thus providing the graft with a dry adhesive surface. The disclosed methods described above and herein can provide enhanced accuracy, for example, with respect to location and orientation, in the placement of the prostheses within a region of a patient's aorta having an aneurysm or other diseased or damaged condition therein.

Although the techniques of the present invention can be used to facilitate both open and minimally invasive abdominal or thoracic aortic aneurysm procedures (or any other aneurysm procedure in the aorta or other areas of the body as well), the following illustration describes only an endovascular minimally invasive repair procedure which is less traumatic to the patient than an open-chest procedure. One of ordinary skill in the art, however, will appreciate that the techniques disclosed can be readily applied to open chest procedures as well in which access to the thoracic cavity is achieved through a midline partial or median sternotomy, a mini-thoracotomy incision, or a retroperitoneal incision, for example.

In one embodiment of the present invention, it is preferred that the plurality of nanostructures have such composition, density, functionality, etc. so as to impart adhesive properties to the nanostructured surface. Such a nanostructured surface is sometimes known in the art as "Nanofur".

In one embodiment of the present invention the nanowires of the nanostructured surface are fabricated using a bottom-up catalyst assisted vapor-liquid-solid (VLS) synthetic approach based on the work of Dr. Charles Lieber, Harvard University and Dr. Peidong Yang, University of California at Berkeley: Cui Y. et al, "Nanowires as Building Blocks for Nanoscale Science and Technology"; Nanowires and Nanobelts: Materials, Properties and Devices, Z. L. Wang, ed. pp. 3-68 Kluwer Academic/Plenum Publishers (2003) and Qian F. et al., "Core/Multishell Nanowire Heterostructures as Multicolor, High-Efficiency Light-Emitting Diodes," Nano Letters., (5), pp. 2287-2291 (2005), the contents of which are incorporated herein by reference. In this method, a metal such as gold particle catalysts with known diameters are deposited from solution on a substrate. The substrate is heated to 300° C. to 500° C. (if Au is being used) in the presence of metal hydride or metal halide gas precursor. The length of the wires is determined by the growth time and conditions, the diameter is determined by the diameter of the gold catalyst particles used, and the density of wires across the surface is determined by the density of catalyst particles deposited on the surface prior to growth. Orientation, branching and the composition of the wires may be controlled by varying synthesis conditions and materials. The invention contemplates nanostructured surfaces having one, two, three and/or all sides of a substrate having positioned thereon any desired number and optionally compositionally varied nanostructures (nanowires or nanotubes).

Fabrication of nanostructured surfaces in accordance with this invention is possible using a variety of different materials and resulting in a variety of different surface compositions (e.g. nanowire composition), including non-limiting examples such as inorganic materials including inorganic semiconductors such as Si, SiO, SiO2, GaAs, InAs, and medical grade materials such as ZnO and TiO2. Nanostructured surfaces in accordance with this invention have been synthesized and some non-limiting examples of which are set forth in Table I below.

TABLE I

| Material | Form Factor |
| --- | --- |
| Silicon | Planar Wafer |
| Silicon oxide | Planar Wafer |
| 361 stainless steel | Foil |
| 361 stainless steel | Mesh |
| 1100 Aluminum | Foil |
| Titanium | Foil |
| Alumina | Fabric |
| Borosilicate | Fiberglass |
| Cobalt Chromium | Substrate |
| High Temperature Plastic | Fabric |
| Titanium | Orthopedic Substrate |

In one embodiment of manufacture of nanostructured surfaces useful with this invention, the metal (gold, for example) catalysts that define the location and diameter of the nanowires within the nanostructured surface are coated in solution and these films can be fabricated on a variety of substrate materials depending on the end use. One skilled in the art will appreciate that the choice of substrate is in part dictated by reaction conditions and nanowire compatibility. For certain substrate materials such as Nitinol, titanium or stainless steel, which are common materials used in the medical device industry, in order to promote growth of silicon nanowires, for example, on such surfaces it has been found by the inventors of the present invention that a barrier layer may be needed. For silicon nanowires, the barrier layer can be, for example, a thin (e.g., approximately 1 to 20 nm, e.g., about 1 to 10 nm, e.g., about 5 to 10 nm) layer of microcrystalline silicon that is conformally deposited via Chemical Vapor Deposition (CVD) or other suitable technique such as sputtering or Atomic Layer Deposition (ALD) on the substrate surface prior to growth of the wires. This thin silicon layer helps promote silicon nanowire growth and prevents any contamination or detrimental contaminants (e.g., nickel) from rising to the surface during the elevated temperature process. Accordingly, silicon nanowire growth on stainless steel, titanium, nitinol, and possibly many other materials can be improved with the provision of a thin silicon layer that is conformally deposited onto the materials' surface. The invention contemplates many different shaped surfaces, including planar surfaces and even complex three dimensional shapes and shapes having voids therein, even microcellular voids. The invention contemplates voids as small a 1 micron in diameter, with preferred ranges between 10 and 100 microns.

Figure 15:
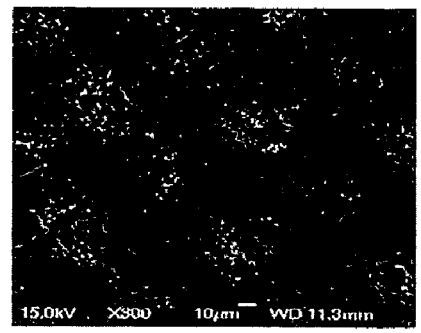
FIG. 15 shows nanostructures grown on stainless steel mesh.

In one embodiment of the present invention there is contemplated a unique nanostructured coating which is formed by growing nanometer-sized wires of various inorganic materials onto a surface. FIG. 15 shows nanostructures grown on stainless steel mesh. The present invention contemplates that the size, shape and other features within the coating may be on a very similar size-scale as many biological structures, allowing the coating to mimic various biological functions. In one preferred embodiment the invention mimics the foot of a gecko, creating a unique non-chemical adhesive, similar to one-sided Velcro™.

In another embodiment of the present invention there is contemplated a method of promoting tissue integration into and/or onto nanostructure coated surfaces, thus mimicking the structure of collagen in an extra-cellular matrix.

According to the present invention the chemistry and morphology of the nanostructured surface may be modified to control and provide biostability and hemocompatibility (blood compatibility) under the conditions of continuous blood-flow.

According to another embodiment of the present invention the total adhesiveness of nanostructured surface may be tailored depending on the material used (different materials will have different attractive forces to other materials), and by varying the amount of nanostructures (nanotubes or nanowires) that comprise the nanostructured surface.

The nano-adhesive like surface of nanostructured surfaces of the present invention employs Van der Waals forces—the intermolecular interactions that result when a spontaneous dipole in one molecule induces a dipole in a neighboring molecule causing a transient attraction between the two. Van der Waals force occurs at the atomic scale and is relatively weak. In nature, geckos and some insects use Van der Waals interaction as a mode of adhesion. They have developed dense arrays of protein fiber structures known as "setae" that are in the 10s to 100s of nanometers in diameter and many microns long. When placed in contact with surfaces these fibers deform against them, making intimate contact, Autumn, K. et al., "*Evidence for van der Waals adhesion in gecko setae*", PNAS Early Edition, pp. 1-5, 2002, the contents of which are hereby incorporated herein by reference.

The Van der Waals interaction of each fiber with the substrate is relatively weak. However, the aggregate interaction of all the fibers to the surface is exceptionally strong, allowing animals to climb vertical walls and hang from ceilings irrespective of material or surface composition. Recently, researchers have created "artificial gecko feet" by using high-resolution lithography and semiconductor processing to fabricate nanofibers of similar dimensions to the setae.

Nanostructured surfaces made according to the present invention have an unexpectedly higher adhesive force than other forms of artificial gecko adhesives that have been demonstrated in the prior art. While the lithographic synthetic setae of the prior art has generated adhesive forces only about ⅓ that of an actual gecko (approximately $3N/cm^2$), nanostructured surface based structures according to the present invention have generated adhesive force that is more than 10× greater (approximately 20 N/cm²), or more than 2× greater adhesive force than an actual gecko.

Figure 14A:
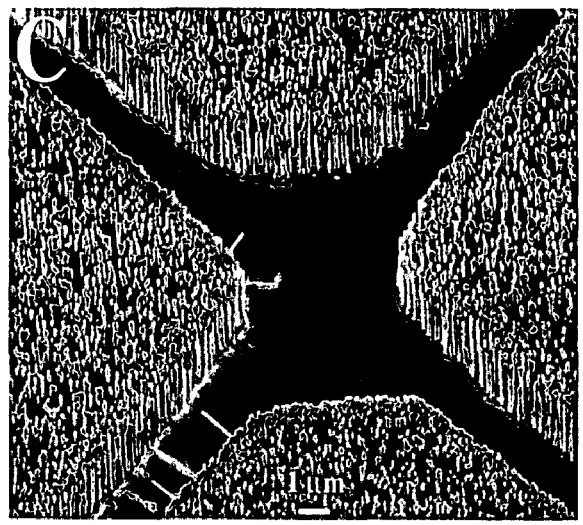
FIGS. 14A-C shows SEM images of patterned (a) and unpatterned (b) nanostructured coatings on planar (a and b) and 3D (c) surfaces.
Figure 14B:
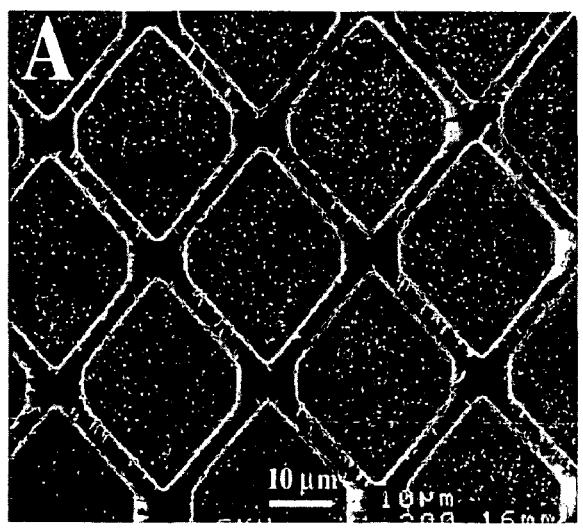
Figure 14C:
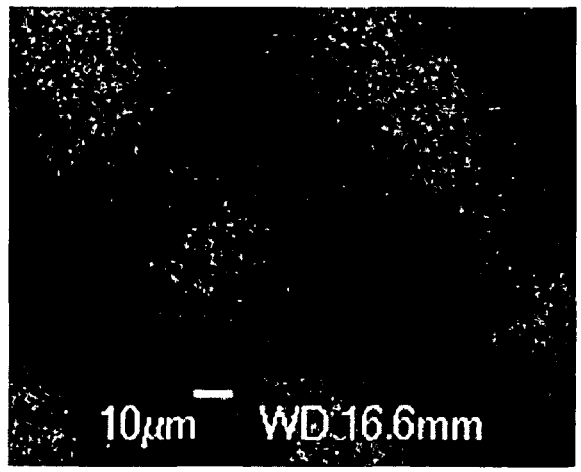

In one embodiment of the present invention the process of making is a growth process allowing for the control and creation of conformal coatings, enabling the facile creation of complex 3-D geometries such as those found in traditional endo-grafts (see FIG. 14C). Further the use of non-plastic inorganic materials provides strong fixation of the implant without the problem of leachable components that are common to many plastic approaches.

Another embodiment of the present invention is the ability of the nanostructured surface to peel even though the adhesion force is very strong. This is because the force is strong in shear but not in peel. By breaking the wire to contact substrate interactions a few at a time, the adhesive force can be readily overcome. This is not so when trying to lift the entire coating off at once. The analogy would be to peeling tape or Velcro™ off of a surface at an angle versus trying to slide it across a surface after it is stuck down. Nanostructured films of the present invention employing nanotubes or nanowires are akin to single sided Velcro. The ability to reposition the endo-graft during the implantation procedure to ensure optimum fixation and integration is a practical advantage of our proposed approach that this strength in shear, but weakness in peel allows.

In one embodiment of the present invention, the nanostructures adhere by Van der Waals forces alone, without chemical bonds. Because of the non-chemical nature of the nanostructured film of the present invention, films adhere to both dry and wet surfaces.

To demonstrate the adhesiveness of the films of the present invention, the nanowire film of one embodiment of the present invention is made to adhere to a blood worm; blood worms are a common surrogate used for purposes of evaluating clamping force on blood vessels. Nanostructured surface made according to the present invention was able to adhere to the blood worm to such an extent that ultimate adhesion could not be measured, since the bloodworm would break before the adhesion between the nanowire coating and bloodworm released.

The present invention contemplates that the surface morphology can be engineered to support soft-tissue integration. In addition, the nanowire structure is such that the matrix or structure can be engineered to enhance endothelial integration, including the incorporation of vascular endothelial growth factor (VEGF) or some other tissue integrating agent, see Genove E. et al., "*The effect of functionalize self-assembling peptide scaffolds on human aortic endothelial cell formation*", Biomaterials, (26), pp. 3341-3351, (2005), the contents of which are hereby incorporated herein by reference.

Nanostructured films according to the present invention have a chosen morphology, hydrophillicity and porosity of the wire network to create a surface hospitable to cellular in-growth and integration. The wire networks form a structure analogous to extra-cellular matrix (ECM). ECM is the natural scaffold on which many of the cells within tissue reside. The major component of ECM is collagen, a high aspect ratio, hydrophilic protein composed of fibrils approximately 50 nm in diameter. These attributes are mimicked by nanowires. Nanowire diameters can be controlled in a range comparable to that of collagen fibrils to full collagen protein. Also, much like collagen, the outer surface may be hydrophilic. The nanowire network appears similar to ECM in that matrix is a porous network of connected proteins between which cells can adhere. Similarly, even a nanowire network that has strong gecko adhesive properties is quite porous. Nanowire networks that support 20N/cm² are approximately 98% porous.

An advantage of the nanostructured films of the present invention is the ability to promote adhesion of the endo-graft to the aorta wall, and simultaneously promotes endothelial growth into to the endo-graft.

Of course, high adhesive force and enhanced tissue integration are only important if the coating is also hemocompatible. Hemocompatibility refers to how the device interacts with blood and its constituent elements. The less the nanostructured film is thrombus generating (or clot forming) on its surface, the more suitable it is for uses in aneurysm repair, Hanson S. R. et al. "*Blood Coagulation and Blood-Materials Interactions*", In: Biomaterials Science—An Introduction to Materials In Medicine, Ratner, B. D. (ed), pp. 193-200, Academic Press, (1996), the contents of which are hereby incorporated herein by reference and discloses suitable materials for hemocompatibility. Silicon dioxide (glass) is considered to be highly clot forming, and therefore has poor hemocompatibility. According to the present invention, the van der Waals interactions are relatively independent of the composition of the nanowires, thus allowing for the independent tailoring of the hemocompatibility properties. This provides flexibility in use for a biostable and hemocompatible coating. For aneurysm uses, the coating must be equivalent in hemocompatibility to the currently used Nitinol endo-graft.

The present invention contemplates coatings of hemocompatible materials known in the art such as pyrolytic carbon and $TiO_2$ on the nanostructures (nanowires or nanotubes). $TiO_2$ is preferred in one embodiment. Techniques for coating various materials are known in the art. Chemical vapor deposition (CVD), e-beam evaporation or atomic layer deposition are non limiting examples. Atomic layer deposition (ALD) is a preferred technology for depositing thin conformal layers of material at low temperature. With ALD, complex structures can be coated to create heterostructures. The outer layer is referred as a shell and the overall architecture is referred to as a core-shell architecture, see for example Ferguson J. D., et al. "TiO2 Atomic Layer Deposition on ZrO2 Particles Using Alternating Exposures of TiCl4 and H2O", Applied Surface Science, (226), pp. 393-404, (2004). This process is conformal even when coating structures with very high aspect ratios such as nanowires. This conformality comes from the layer by layer deposition process. To add a shell (herein, a non-limiting example of $TiO_2$ is set forth) on a nanowire by this method, generally begins by adsorbing a layer of a titanium containing precursor, such as $TiCl_4$. until the wire structure is substantially saturated with precursor. This exposure to the point of saturation is what makes end coating conformal and pinhole free. After purging the vessel, the next reactive species is introduced. For $TiO_2$ synthesis this would be $H_2O$. HCl(g) and $TiO_2$(s) are end products of this reaction. Again, the step is performed to saturation to ensure conformatility. This cycle can be continued numerous times to attain a $TiO_2$ film of desired thickness.

The shape memory of Nitinol is a key property that makes it very amenable for use in medical devices. Cold working—the temperature at which the shape of the metal is fixed—is usually around 500° C. to 650° C. Wire synthesis is done at a temperature above the eutectic point of gold and silicon, between 360° C. and 550° C. Disilane may be used as a silicon precursor to enhance wire growth at lower temperatures approaching the eutectic point of gold and silicon.

In another embodiment of the present invention, multiple pieces or strips of nanostructured surfaces may be applied to the patient to treat aneurysm thus allowing for overlap and increased positional accuracy.

Figure 3A:
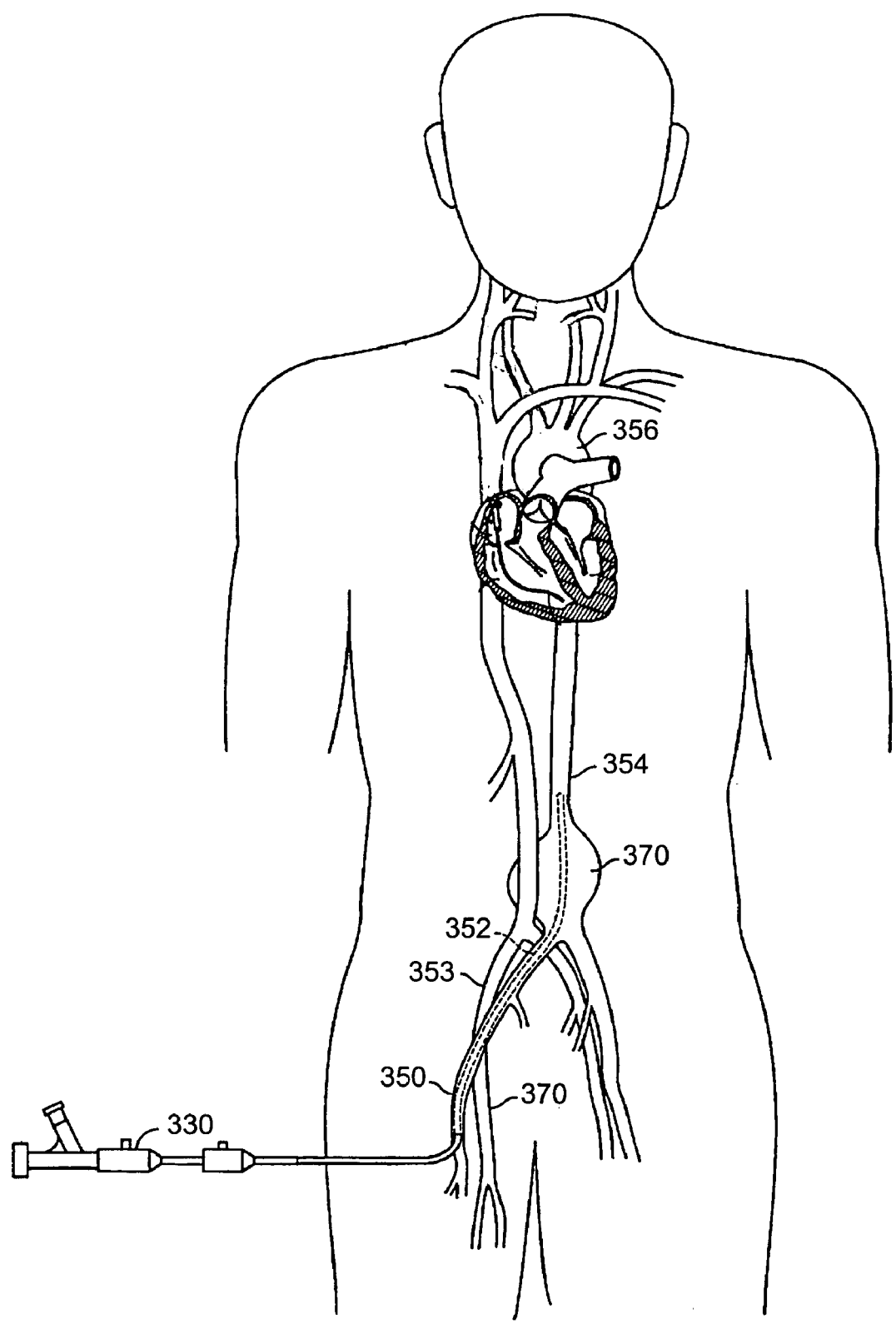
FIG. 3A diagrammatically illustrates an endovascular aortic prosthetic delivery system for delivering an aortic aneurysm graft having a nanostructured surface to the site of an aortic aneurysm in a body of a patient.
Figure 3B:
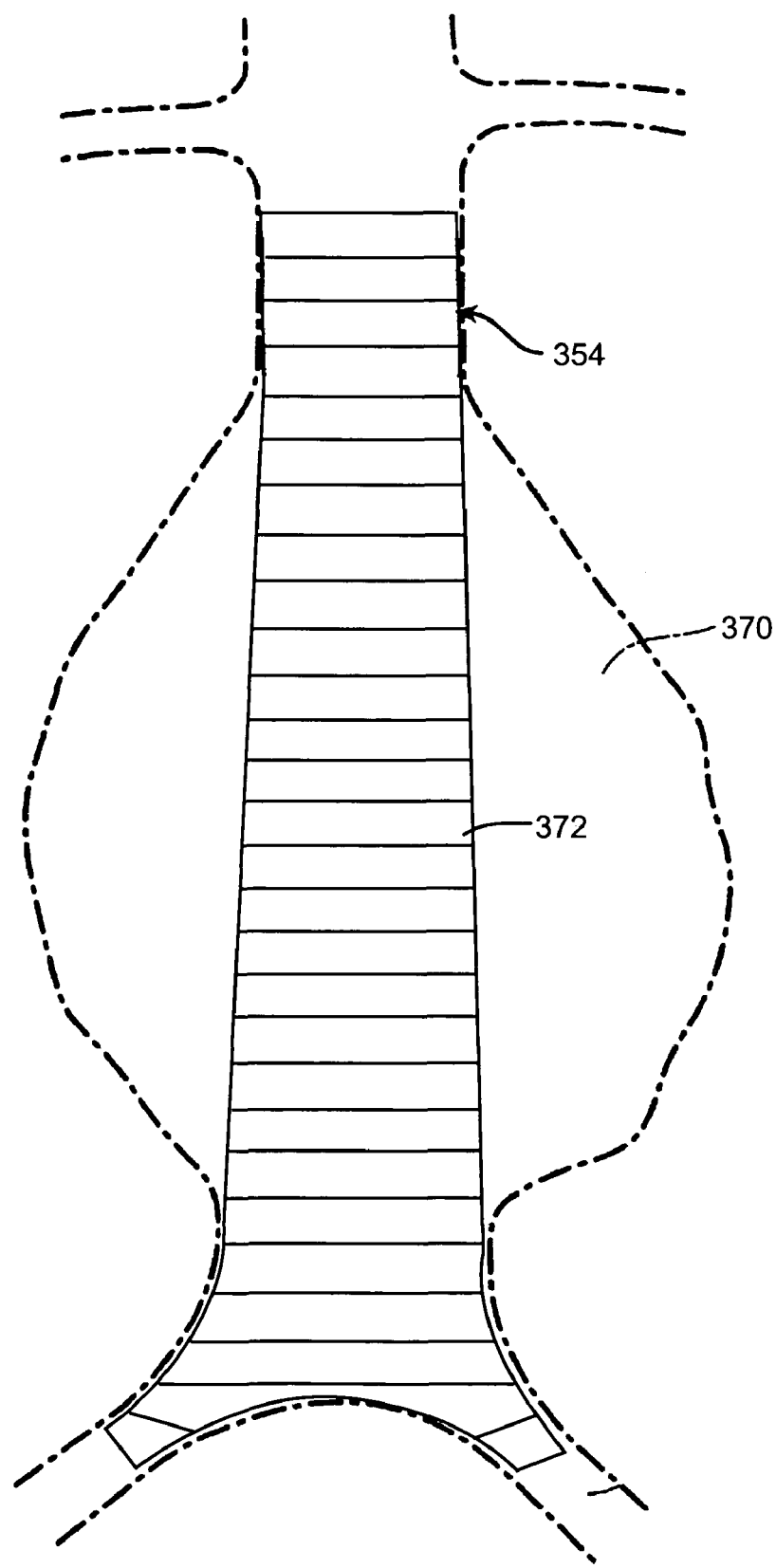
FIG. 3B illustrates placement of an endovascular aortic graft having a nanostructured surface adjacent an aneurysm in an aorta of a body of a patient.

Referring now to FIGS. 3A-B, a system is schematically illustrated for placing a prosthetic graft during a closed-chest abdominal or thoracic aortic aneurysm repair procedure using the methods and compositions of the present invention. In one embodiment, a patient is anesthesized and generally prepared for surgery in a conventional manner. The procedure then involves positioning the stent graft deployment mechanism and stent graft 372 (FIG. 3B within the abdominal aorta 354 (or thoracic aorta 356) at the site of aneurysm 370. Endovascular devices which can be used for aortic aneurysm repair include, for example, balloon-expandable or self-expandable devices. Balloon-expandable stent designs are described, for example, in Parodi et al., Ann. Vasc. Surg. 1991; 5:491-499 and White et al., J. Endovasc. Surg. 1994; 1:16-24, the disclosures of which are incorporated by reference herein. The following devices have received FDA approval for use in the abdominal aorta and are examples of systems that can be used in practicing the present invention:

(1) Ancure® Endograft® System (Guidant Corporation). In this system, which was approved in 1999, the endograft is placed in the aorta and expanded using balloon dilation. The graft is anchored to the vessel wall using sutureless hooks at its superior and inferior ends. On Mar. 16, 2001, Guidant suspended production of this system and announced a recall of all existing inventories. The company reported to the FDA that they had failed to report many device malfunctions and adverse events, including severe vessel damage associated with problems with the deployment of the device. There were also manufacturing changes that were not properly reported to the FDA. The FDA issued a Public Health Notification: Problems with Endovascular Grafts for Treatment of Abdominal Aortic Aneurysm (AAA), regarding both this device and the AneuRx device.

(2) Ancure® Aortoiliac System (Guidant Corporation). This new version was approved in 2002 and is identical to the earlier Guidant Endovascular Grafting System except that the aortoiliac Ancure® grafts have suture loops on the superior and inferior attachment systems. The device is intended for use in patients whose anatomy is not suited for the use of the single tube or bifurcated endograft device.

(3) AneuRx® Stent Graft System (Medtronic AVE). The AneuRx system, approved in 1999, consists of a woven polyester interior surface with a self-expanding Nitinol exoskeleton. The radial force of the expanding stent embeds in the exoskeleton into the aneurysm wall, and thus constitutes the attachment mechanism. This device was also the subject of the above FDA Public Health Notification. In December 2003, the FDA published updated information on the mortality risks associated with the AneuRx® Stent Graft System based on an analysis of longer term follow-up data from the premarket study. Based on the findings of the study, the FDA recommended that the AneuRx® Stent Graft be used "only in patients who meet the appropriate risk-benefit profile and who can be treated in accordance with instructions for use."

(4) EXCLUDER™ Bifurcated Endoprosthesis (W.L. Gore and Associates, Inc.). Approved in 2002, this device self-expands inside the aorta to the diameter of the aorta and iliac arteries, thus sealing off the aneurysm and relining the artery wall.

(5) Zenith™ AAA Endovascular Graft and H&L-B One-Shot™ Introduction System (Cook, Inc.). This device was approved in 2003; it is self-expanding and attaches to the vessel wall via barbs.

Each of these devices may be deployed across the aneurysm such that the aneurysm is effectively "excluded" from the circulation with subsequent restoration of normal blood flow. The above-referenced systems generally consist of an endograft prosthesis 372 (FIG. 3B) and a corresponding delivery catheter 330. The prosthesis is a vascular graft which isolates the aneurysm 370 from blood flow and pressurization, thus precluding aneurysm expansion and minimizing the risk of rupture. The delivery catheter 330 is an over-the wire system which may nor may not be coated with nanostructures in accordance with the present invention, and which is subcutaneously inserted into a femoral or iliac artery 350, 352 in the groin area using known techniques such as a cut-down or a percutaneous technique such as the Seldinger technique. The delivery catheter 330 is advanced into the aorta 354 under image (e.g., fluoroscopic, echocardiographic, MRI, or CT scan) guidance to the site of the aneurysm 370 and is designed to transport the preloaded prosthesis to the aorta. The compressed prosthesis is pre-loaded within a special delivery sheath. Some prostheses consist of modular components such that the delivery is comprised of the primary prosthesis plus one or two "docking limbs." Due to the large size of the delivery sheaths, open surgical exposure of one or both groins is required to establish vascular access. After entry into the arterial system, the prosthesis is fluoroscopically guided through the iliac arteries into the aneurysm site, followed by deployment of the prosthesis with the use of a compliant low-pressure balloon.

Artificial grafts can include, for example, treated natural tissue, laboratory-engineered tissue, and synthetic polymer fabrics. Synthetic polymers such as Dacron® and Teflon® (i.e., expanded polytetrafluoroethylene (ePTFE)) are the most commonly used of the synthetic grafts. See, for example, "Tissue Engineering of Vascular Prosthetic Grafts," P. P. Zilla, H. P. Griesler, and P. Zilla, Pub. by Landes Bioscience (May 1999), the entire contents of which are incorporated by reference herein. Other synthetic materials can be used as well such as poly (alpha-hydroxy ester)s, polyanhydrides, polyorthoesters, polyphosphazens, as well as synthetics such as tyrosine-derived polycarbonates and polyarylates, lactide based polydepsipeptide polymer, poly(L-lactide acid-co-L-aspartic acid), and lactide based poly(ethylene glycol). Metals such as stainless steel, titanium, or Nitinol metal mesh may also be used as the synthetic graft material, as well as other alloys as well such as woven glass (e.g., knitted or spun) or ceramics. The present embodiment of the invention entails the further use of nanostructured components (e.g., nanofibers or nanowires) to enhance the interaction of the graft with the passages in which they are used as shown, for example, in FIG. 1. Typically, such nanostructured surfaces are employed to improve adhesion, friction, biointegration or other properties of the device to enhance its patency in the subject passage. Such enhanced interactivity is generally provided by a nanostructured surface that interacts with the surface of the passage, e.g., an inner or outer wall surface, to promote integration therewith or attachment thereto.

As described above, the nanostructured components can take a variety of forms and configurations depending on the application, such as nanofibers or other nanostructured component, e.g., nanowires, nanorods, nanotetrapods, nanodots and the like as described in more detail below, which are incorporated into or onto the synthetic graft to improve its properties such as adhesion. The nanofibers can either be attached to the outer or inner surface of the synthetic graft, e.g., by growing the nanofibers directly on the outer and/or inner surface of the graft, or by separately covalently (or otherwise) attaching the fibers to the graft surfaces. In addition, the nanofibers or other nanostructures can be embedded into the graft material to provide it with enhanced properties such as improved rigidity and strength within the aorta. The shape and size of the nanofibers as well as their density on the graft surfaces can be varied to tune the adhesive properties of the graft to the desired levels.

The artificial grafts of this invention may also be coated (in the case of tubular grafts, on the inside and/or outside) with other materials to still further enhance their bio-utility. Examples of suitable coatings are medicated coatings, hydrophilic coatings, smoothing coatings, collagen coatings, human cell seeding coatings, etc. The above-described nanofiber coatings on the graft provide a high surface area to volume ratio that helps the graft to retain these coatings. For example, the artificial graft may be coated with additional biocompatible materials to minimize thrombogeneity of the graft. Coatings such as endothelial cell linings found in autologous vessels, polymers, polysaccharides, etc can provide a non-thrombogenic surface to increase endothelial cell proliferation. The graft can also be modified with one or more proteins or growth factors to increase cell adhesion, growth, and proliferation such as, for example, VEGF, FGF-2 and other HBGF (Heparin Binding Growth Factors), fibrin and fibrinogen.

In one embodiment of the present invention it is contemplated that a nanostructure or plurality of nanostructures (nanowire, nanotube or nanoparticle or combinations thereof) attached or associated with a substrate that in one embodiment may be an embolic device, such as a coil or patch, may have a coating of fibrin and/or fibrinogen thereon. In another embodiment the fibrin and/or fibrinogen is partially or wholly encapsulated by a biocompatable polymer, non-limiting examples of which include polyglycolic acid, poly-L-lactic acid, poly-DL-lactic acid, poly-D-lactic acid, poly(lactic acid-glycolic acid) copolymer, poly-epsilon-caprolactone, poly(glycolic acid-caprolactone) copolymer, polyamino acid, polyanhydride, polyorthoester, and copolymers and mixtures thereof. It is preferable to use compositions which are accepted by the Food and Drug Administration (FDA) and have been used as a biodegradable polymer which can be used in a human body. The biocompatible polymer may be configured to be biodegradable such that the polymer helps to prevent any potential physical or mechanical damage to the wires during insertion of the coil into the vessel at the site of the aneurysm, and then erodes over time in the vessel to expose the nanowires to assist in clot formation.

In one embodiment of the present invention, the coatings are adsorbed directly to the nanostructured surface of the graft. Alternatively, the nanostructured surface may be provided with a linking agent capable of forming a link to the nanostructured components (e.g., nanofibers, nanotubes or nanoparticles) as well as to the coating material optionally applied thereto. In such cases, the coating may be directly linked to the nanostructured surface, e.g., through silane groups (or other linking agents known in the art), or it may be coupled via linker binding groups or other appropriate chemical reactive groups to participate in linkage chemistries (derivitization) with linking agents such as, e.g., substituted silanes, diacetylenes, acrylates, acrylamides, vinyl, styryls, silicon oxide, boron oxide, phosphorus oxide, N-(3-aminopropyl)3-mercapto-benzamide, 3-aminopropyl-trimethoxysilane, 3-mercaptopropyl-trimethoxysilane, 3-maleimidopropyl-trimethoxysilane, 3-hydrazidopropyl-trimethoxysilane, hydroxysuccinimides, maleimides, haloacetyls, pyridyl disulfides, hydrazines, ethyldiethylamino propylcarbodiimide, and/or the like.

XXII) Occlusion of Blood Vessels in the Brain and Other Organs of the Body

The compositions, apparatus, systems and methods relating to nanostructured surface coatings described herein can further be used in the treatment of various diseases and conditions of the circulatory system and other organs of the body that are beneficially treated by the occlusion of blood vessels. Examples of the numerous diseases that can be treated by blocking associated blood vessels using, for example, intravascular coils, beads, synthetic grafts or other liquid embolic agents which are treated with nanofibers (or other nanostructured components), include arteriovenous (AV) fistulas, AV malformations, aneurysms and pseudoaneurysms, patent ductus arteriosus, patent foramen ovale, gastrointestinal bleeding, renal and pelvic bleeding, and tumors.

Placement of various substances (e.g., a liquid adhesive such as isobutylcyanoacrylate (IBCA)) within the blood vessels is one of the methods of encouraging the formation of thrombus (clot) which leads to the complete occlusion of the vessels. Occlusive coils have also been used to occlude blood vessels. The purpose of the coil is to encourage quick formation of a thrombus around the coil.

Of the many diseases that may be treated with embolic coils, cerebral aneurysms are of particular interest. Ruptured and unruptured cerebral aneurysms may in some cases be treated by a surgical approach in which the aneurysm is visualized directly and then surgically clipped thereby blocking blood flow into the aneurysm. Once the aneurysm is eliminated from the blood flow the risk of hemorrhage is eliminated. Another less invasive approach to the treatment of cerebral aneurysms is an endovascular approach, in which a catheter is introduced into the cerebral vascular system from a peripheral access point, such as a femoral artery, to access the aneurysm internally. The catheters can be used to deliver embolic devices, such as a balloon or a coil, to the site of the aneurysm to block blood flow into the aneurysm. The use of embolic coils, however, can lead to complications because the coils can compact over time and allow re-filling of the aneurysm, posing risk of rupture.

The present embodiment of the invention involves the use of an endoluminal patch for the repair of, for example, side wall aneurysms in the brain or elsewhere in the arterial vasculature. Although the present methods are discussed in relation to the treatment of cerebral side wall aneurysms in particular, it is to be appreciated that the systems and methods of the present invention may be used in connection with a variety of other embolotherapy procedures in various blood vessels and organs of the body where an embolic device, such as a coil or embolic patch material, may be deployed.

Figure 4A:
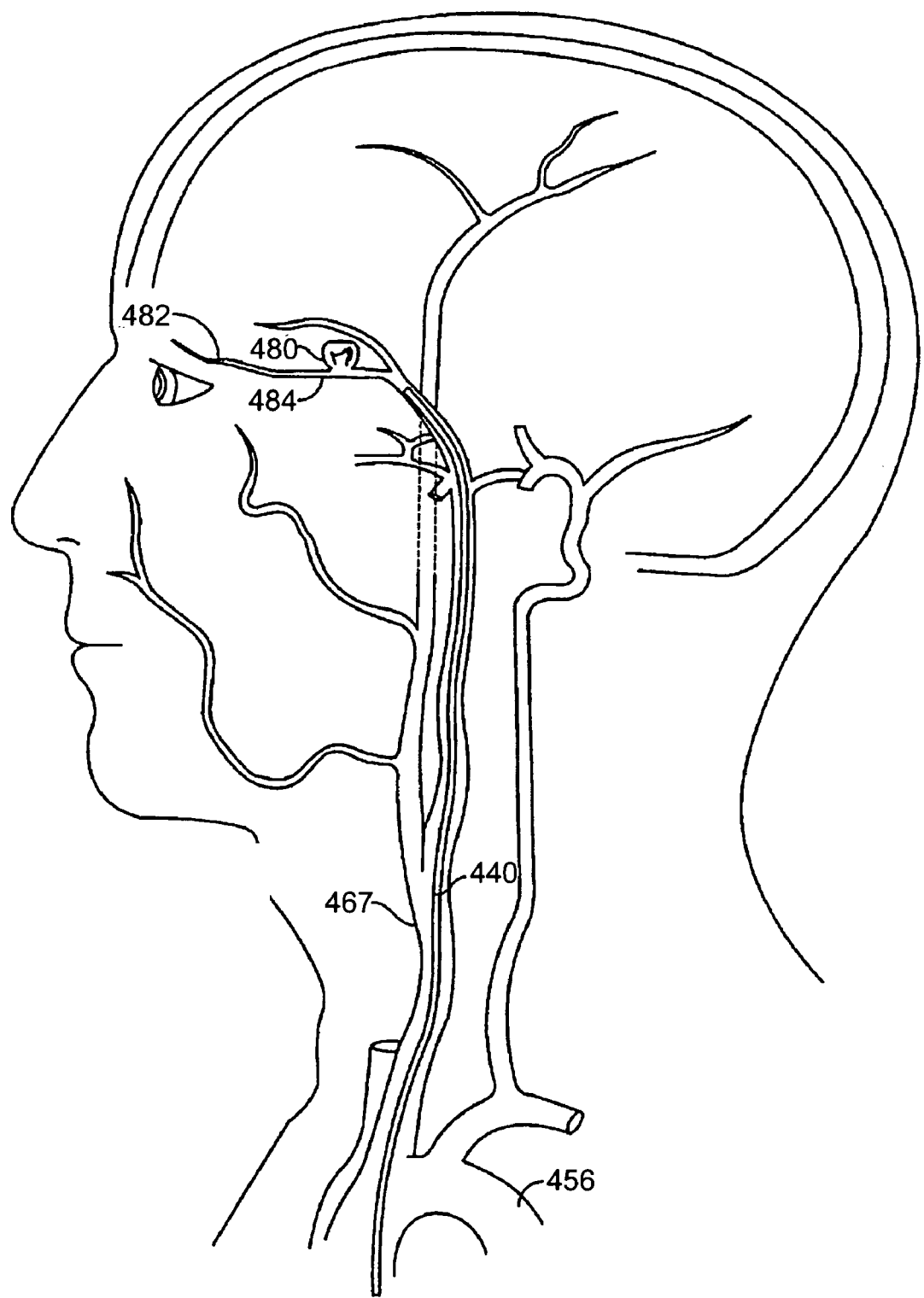
FIG. 4A illustrates a detailed view of a patient's head region showing advancement of a neurovascular catheter delivery system for treatment of an aneurysm in a side wall of a cerebral vessel of a patient in accordance with the invention.
Figure 4B:
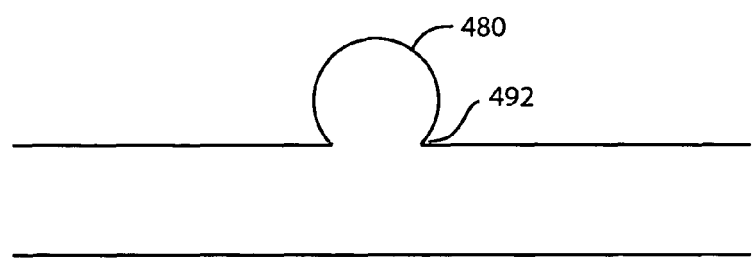
FIG. 4B illustrates a side wall aneurysm in a cerebral vessel of a patient.
Figure 4C:
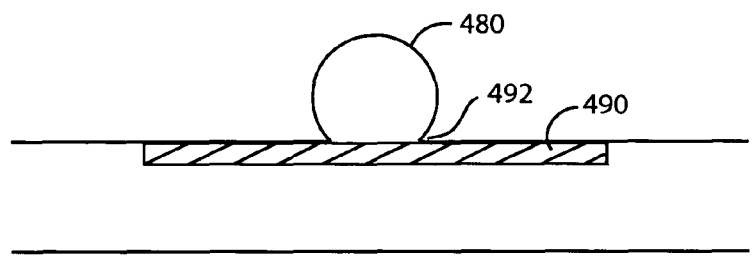
FIG. 4C illustrates placement of a patch having a nanostructured surface at the site of the side wall aneurysm of FIG. 4B.

The systems and methods disclosed can be used to facilitate the accurate deployment of embolic devices and/or materials within the cerebral vasculature system of a patient, such as at the site of an aneurysm, as schematically illustrated in FIGS. 4A-C. A patch of any suitable biocompatible material including, for example, metal mesh, alloys, treated natural tissue, laboratory-engineered tissue, and synthetic polymer fabrics or other polymeric material, is coated with nanostructured components (e.g., nanofibers, nanowires, nanotetrapods, nanodots and the like) on all or select portions of its exterior (and/or interior) surface rendering it adhesive. The size, shape and density of the nanofibers can be varied as described above in relation to previous embodiments to alter and control the adhesive properties of the patch. The nanofibers, for example, may be grown directly on the external (and/or internal) surfaces of the patch or grown separately and applied to the patch material after harvesting. The nanofibers may also be incorporated directly into the material of the patch to further strengthen its rigidity.

The artificial patches of this invention may be coated with other materials to still further enhance their bio-utility. Examples of suitable coatings are medicated coatings, hydrophilic coatings, smoothing coatings, collagen coatings, human cell seeding coatings, etc. The above-described nanofiber coatings on the patch helps the patch to retain these coatings. For example, the patch may be coated with additional biocompatible materials to minimize thrombogeneity of the patch. Coatings such as endothelial cell linings found in autologous vessels, polymers, polysaccharides, etc. can provide a non-thrombogenic surface to increase endothelial cell proliferation. The patch can also be modified with one or more proteins or growth factors to increase cell adhesion, growth, and proliferation such as, for example, VEGF, FGF-2 and other HBGF (Heparin Binding Growth Factors).

The coatings can be adsorbed directly to the nanostructured surface of the patch. Alternatively, the nanostructured surface may be provided with a linking agent which is capable of forming a link to the nanostructured components (e.g., nanofibers) as well as to the coating material which is applied thereto. In such cases, the coating may be directly linked to the nanostructured surface, e.g., through silane groups, or it may be coupled via linker binding groups or other appropriate chemical reactive groups to participate in linkage chemistries (derivitization) with linking agents such as, e.g., substituted silanes, diacetylenes, acrylates, acrylamides, vinyl, styryls, silicon oxide, boron oxide, phosphorus oxide, N-(3-aminopropyl)3-mercapto-benzamide, 3-aminopropyl-trimethoxysilane, 3-mercaptopropyl-trimethoxysilane, 3-maleimidopropyl-trimethoxysilane, 3-hydrazidopropyl-trimethoxysilane, hydroxysuccinimides, maleimides, haloacetyls, pyridyl disulfides, hydrazines, ethyldiethylamino propylcarbodiimide, and/or the like.

The endoluminal patch 490, (FIG. 4C) is mounted on a compliant, low-pressure balloon catheter such as those shown in U.S. Pat. Nos. 4,739,768 and 4,884,575, the disclosures are of which are incorporated by reference herein. These procedures use catheters introduced into the cerebral vascular system from a peripheral access point, e.g. a femoral artery, to access the aneurysm internally. The catheters can be used to deliver the patch 490 to the site of the aneurysm 480 to block blood flow into the aneurysm. The embolic delivery catheter 440 is introduced into a blood vessel in the brain having a side wall aneurysm or other disease condition therein. The diseased site may be an aneurysm 480 as shown in FIG. 4A, or a fistula, AV malformation, or other disease in which deployment at, on or near the disease condition would result in reduced or stopped flow to the abnormal area. To accomplish this, FIGS. 4A-C show one exemplary use in which the embolic device, in this case a patch 490, is placed via the delivery catheter 440 over the aneurysm neck, to block blood from entering the aneurysm. The catheter 440 is typically introduced into the cerebral vasculature system of the patient from a peripheral access point such as a femoral artery and guided with the aid of fluoroscopy to the brain through the aorta 456 and through one of the carotid (or vertebral) arteries 467 in the neck. Once the insertion catheter 440 and the patch are threaded through the vasculature system to the site of the aneurysm 480 in the brain, the patch is aligned with the aneurysm neck 492 under radioscopic guidance. The patch is applied to the vessel wall by dilating the balloon catheter 440 to press-fit the patch onto the vessel wall.

Figure 4D:
FIGS. 4D, 4E, and 4F show one example of a commercially available embolic device (i.e., Hilal Embolization Microcoils™ available commercially from Cook, Inc. (Bloomington, Ind.)) that can be provided with a nanostructured surface according to the teachings of the present invention to enhance the treatment of intracranial aneurysms and AV malformations.
Figure 4E:
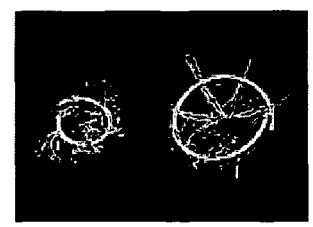
Figure 4F:
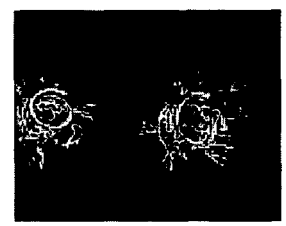

In yet another embodiment, nanostructures (e.g., nanofibers) grown on an embolic device, such as aneurysm coils or beads, e.g., Hilal Embolization Microcoils™ available commercially from Cook, Inc. (Bloomington, Ind.) shown in FIG. 4D, can enhance the thrombogenicity of the embolic device through hydrophilic native platelets from sticking and forming thrombosis. In one embodiment of the present invention there is contemplated an embolic device comprising nanostructures (which may be nanotubes, nanowires or nanoparticles) coated with fibrin and/or fibrinogen. Optionally the fibrin coated nanostructures may be wholly or partially encapsulated in a biocompatible and/or biodegradable polymer such as such as polyglycolic acid (PLG), poly-L-lactic acid (PLA), poly-DL-lactic acid, poly-D-lactic acid, poly (lactic acid-glycolic acid) copolymer (PLGA), poly-.epsilon.-caprolactone, poly(glycolic acid-caprolactone) copolymer (PGCL), polyamino acid, polyanhydride, polyorthoester, poly(L-lactic acid), polycaprolactone, poly(lactide-co-glycolide), poly(hydroxybutyrate), poly(hydroxybutyrate-co-valerate), polydioxanone, poly(glycolic acid-co-trimethylene carbonate), polyphosphoester, polyphosphoester urethane, cyanoacrylates, poly(trimethylene carbonate), poly (iminocarbonate), polyalkylene oxalates, polyphosphazenes and biomolecules such as cellulose, starch, collagen and hyaluronic acid and copolymers and mixtures thereof. It is preferable to use a hydroxy acid which is accepted by the Food and Drug Administration (FDA) and has been used as a biodegradable polymer which can be used in a human body.

XXIII) Sutureless Graft Prostheses

The methods, devices and systems of the invention generally described above may also be used in the performance of anastomosis of blood vessels, ducts, lumens or other tubular organs, e.g., for sutureless anastomosis procedures in which one vessel is joined to another vessel without the use of sutures.

Arterial bypass surgery is a common modality for the treatment of occlusive vascular disease. Such surgery typically involves an incision and exposure of the occluded vessel followed by the joinder of a graft, e.g., a mammary artery, saphenous vein, or synthetic graft (all collectively referred to hereinafter as the "bypass graft"), to the occluded vessel (hereinafter the "native" blood vessel) distally (downstream) of the occlusion. The upstream or proximal end of the bypass graft is secured to a suitable blood vessel upstream of the occlusion, e.g., the aorta, to divert the flow of blood around the blockage. Other occluded or diseased blood vessels, such as the carotid artery, may be similarly treated. Moreover, similar procedures are conducted to place a graft between an artery and a vein in dialysis patients.

Current methods available for creating an anastomosis include hand suturing the vessels together. Suturing the anastomosis is time-consuming and often does not provide a leak-free seal and can lead to a site of turbulent blood flow on occlusion. Thus, it is desirable to reduce the difficulty of creating the vascular anastomosis and provide a rapid method for making a reliable anastomosis between a graft vessel and artery.

One method currently available involves the use of stapling devices. These instruments are not easily adaptable for use in vascular anastomosis. It is often difficult to manipulate these devices through the vessels without inadvertently piercing a side wall of the vessel. In addition to being difficult to operate, these devices often do not provide a reliable leak-free seal.

Myriad other attempts to develop a successful sutureless anastomotic technique are represented by U.S. Pat. Nos. 3,221,746, 3,357,432, 3,648,295, 3,683,926 and 4,267,842, for example. All of these feature an inner tube-like device placed inside the vessels to be anastomosed. Various other devices and methods of use have been disclosed for effecting anastomosis of blood or other vessels, ducts, lumens or other tubular organs. Examples of such devices and methods are found, for example, in U.S. Pat. Nos. 3,221,746, 3,357,432, 3,648,295, 4,366,819, 4,470,415, 4,553,542, 5,591,226, 5,586,987, 5,591,226, and 6,402,767, the contents of which are incorporated by reference herein.

Figure 5A:
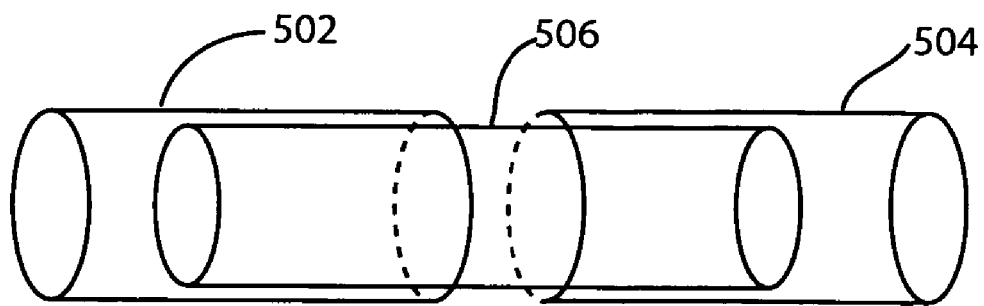
FIG. 5A is an illustration of a tubular device having a nanostructured surface for performance of an end-to-end anastomosis.
Figure 5B:
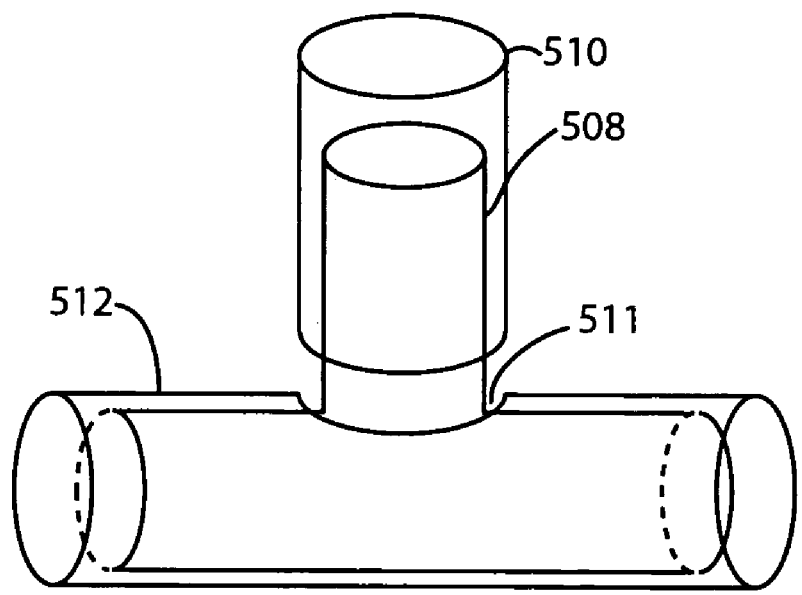
FIG. 5B is an illustration of a T-tube device having a nanostructured surface for performance of an end-to-side anastomosis.

The present embodiment of the invention involves improvements to conventional devices and methods for performing vascular anastomoses. The invention facilitates positioning one vessel in the fluid path of another vessel to enhance the fluid flow juncture therebetween. The invention provides artificial graft tubing by which anatomical structures, such as blood vessels, fallopian tubes, intestine, bowel, ureters, vas deferens and outer nerve sheaths are anastomosed, preferably without the use of sutures. The new tubing may be artificial graft tubing in the form of a simple tube (as shown in FIG. 5A, for example), or a T-tube as shown in FIG. 5B, for example, or any other suitable tubing shape or configuration. Alternatively, the new tubing may be a combination of artificial and natural tubing (e.g., natural tubing disposed substantially concentrically inside artificial tubing).

The artificial tubing may comprise any suitable biocompatible material including, for example, a flexible, semi-porous metal mesh (e.g., Nitinol mesh, stainless steel mesh, titanium mesh and the like), treated natural tissue, laboratory-engineered tissue, and synthetic polymer fabrics or other polymeric material such as Dacron®, PTFE, polyimide mesh, ceramic, glass fabrics and the like.

The present embodiment of the invention entails the further use of nanostructured components to enhance the interaction of the tubing with the passages in which it is used as shown, for example, in FIG. 1. Typically, such nanostructured surfaces are employed to improve adhesion, friction, biointegration or other properties of the device to enhance its patency in the subject passage. Such enhanced interactivity is generally provided by providing a nanostructured surface that interacts with the surface of the passage, e.g., an inner or outer wall surface, to promote integration therewith or attachment thereto.

The new tubing for sutureless anastomosis is coated with nanofibers or other nanostructured components such as nanowires, nanotetrapods, nanodots and the like on all or select portions of its exterior (and/or interior) surface rendering it adhesive. The nanofibers may also be incorporated into the tubing material itself to form a composite material with added rigidity and strength. The size, shape and density of the nanofibers can be varied as described above in relation to previous embodiments to alter and control the adhesive properties of the tubing. The nanofibers may be grown directly on the external (and/or internal) surfaces of the tubing or grown separately and applied to the tubing material after harvesting.

The artificial grafts of this invention may be coated (in the case of tubular grafts, on the inside and/or outside) with other materials to still further enhance their bio-utility. Examples of suitable coatings are medicated coatings, hydrophilic coatings, smoothing coatings, collagen coatings, human cell seeding coatings, etc. The above-described nanofiber coatings on the graft helps the graft to retain these coatings. For example, the graft tubings may be coated with additional biocompatible materials to minimize thrombogeneity of the tubing. Coatings such as endothelial cell linings found in autologous vessels, polymers, polysaccharides, etc can provide a non-thrombogenic surface to increase endothelial cell proliferation. The nanofibers or tubing material can also be modified with one or more proteins or growth factors to increase cell adhesion, growth, and proliferation such as, for example, VEGF, FGF-2 and other HBGF (Heparin Binding Growth Factors). The coatings can be adsorbed directly to the nanostructured surface of the tubing. Alternatively, the nanostructured surface may be provided with a linking agent which is capable of forming a link to the nanostructure components (e.g., nanofibers) as well as to the coating material which is applied thereto. In such cases, the coating may be directly linked to the nanostructured surface, e.g., through silane groups, or it may be coupled via linker binding groups or other appropriate chemical reactive groups to participate in linkage chemistries (derivitization) with linking agents such as, e.g., substituted silanes, diacetylenes, acrylates, acrylamides, vinyl, styryls, silicon oxide, boron oxide, phosphorus oxide, N-(3-aminopropyl)3-mercapto-benzamide, 3-aminopropyl-trimethoxysilane, 3-mercaptopropyl-trimethoxysilane, 3-maleimidopropyl-trimethoxysilane, 3-hydrazidopropyl-trimethoxysilane, hydroxysuccinimides, maleimides, haloacetyls, pyridyl disulfides, hydrazines, ethyldiethylamino propylcarbodiimide, and/or the like.

The nanofibers on the inside and/or outside diameter of the tubing have substantial dry adhesive properties that allow a firm press-fit into the inner (or outer) diameter of the native host vessel or to connect other synthetic graft vessels.

An exemplary form of artificial tubing includes a tube frame of a first highly elastic material (such as Nitinol) covered with a second highly elastic material (such as silicone rubber) to substantially fill in the apertures in the frame. This combination produces an artificial graft that is distensible like natural body organ tubing such as a natural artery. Additional advantages of the artificial grafts of this invention are their elasticity and distensibility (mentioned above), their ability to be deployed through tubes of smaller diameter (after which they automatically return to their full diameter), the possibility of making them modular, their ability to accept natural body organ tubing concentrically inside themselves, their ability to support development of an endothelial layer, their compatibility with MRI procedures, their ability to be made fluoroscopically visible, etc.

A first method of the present invention is for coupling a first vessel 502 and a second vessel 504 in an end-to-end anastomosis (e.g., FIG. 5A) and generally includes inserting an artificial tubular graft 506 as described above with a nanofiber coating into an opening in a bypass graft vessel (which can include a natural or synthetic graft vessel) and a native vessel to be connected, and preferably radially expanding (e.g., with the use of a balloon catheter, for example) at least a portion of the tubular graft to sealingly press-fit and secure the tubular graft to the inner wall of the vessels. The tubular graft member preferably is sufficiently rigid to substantially retain the tubular member in its preformed configuration after the tubular member is radially expanded. The tubular graft member may be radially self-expandable to a pre-formed configuration (e.g., via the use of a shape memory alloy for the tubing such as Nitinol, for example), and thus may assume a press-fit configuration within the vessels to sealingly join them without the use of an access device such as a balloon catheter. In another aspect of the present invention, the tubular member is in the form of a T-tube 508 for an end-to-side anastomosis in which a bypass graft vessel 510 is secured to an opening 511 in a side wall of the native vessel 512 as shown in FIG. 5B. Although grafts in the form of tubing are described above, certain aspects of the invention are equally applicable to other graft procedures and to grafts having virtually any cross-sectional shape depending upon the desired application, including, e.g., circular, elliptical, polygonal, e.g., square, rectangular, pentagonal, hexagonal, octagonal, trapezoidal, rhomboid, etc. Further, it will be appreciated that the cross-sectional shape of the body structure of the graft may be the same as or different from the cross-sectional shape of the vessel into which it is inserted, depending upon a number of factors, including, e.g., the method used to fabricate the graft, and/or its desired application.

XXIV. Orthopedic (and Dental) Implants

Figure 6A:
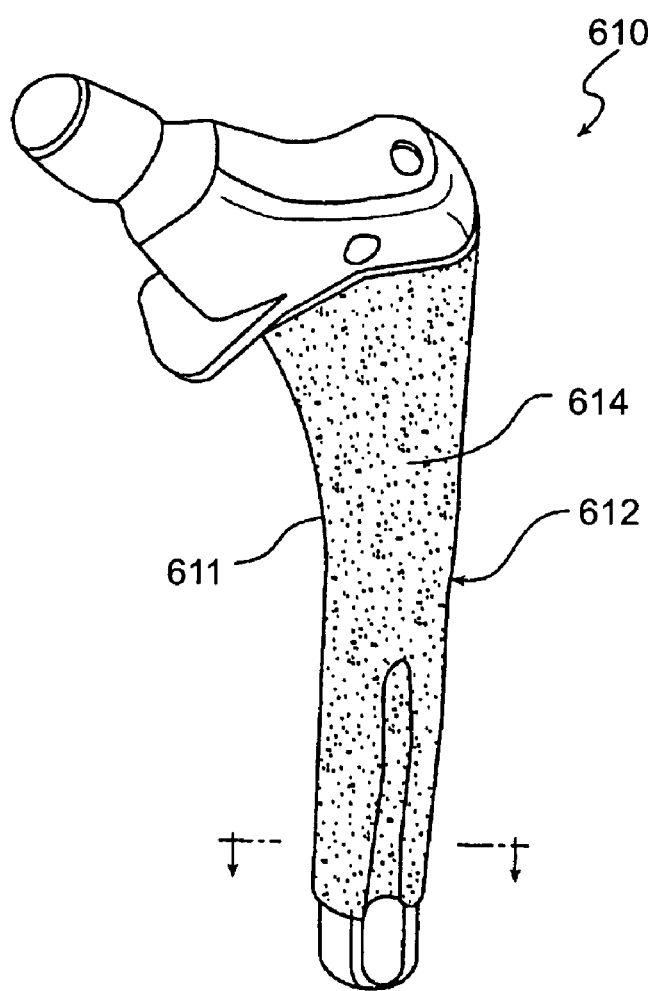
FIG. 6A is a perspective view of a an exemplary orthopedic implant (in this case a hip stem) having a nanofibers attached thereto in accordance with the illustrated embodiment.
Figure 6B:
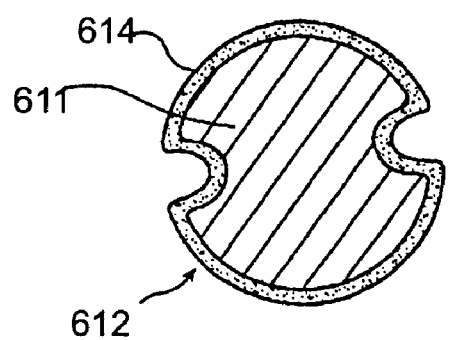
FIG. 6B is a cross sectional view taken along line 6A-6A of FIG. 6A.

Nanostructures (e.g., nanowires, nanorods, nanotetrapods, nanodots and other similar structures) incorporated into or onto orthopedic implants can improve biocompatibility, infection resistance, bone integration, prevention of unwanted cell growth, and durability of those implants when used in and around orthopedic tissues, such as bone, ligaments, muscles, etc. Examples of orthopedic implants that can benefit from nanofiber enhanced surfaces include without limitation total knee joints, total hip joints, ankle, elbow, wrist, and shoulder implants including those replacing or augmenting cartilage, long bone implants such as for fracture repair and external fixation of tibia, fibula, femur, radius, and ulna, spinal implants including fixation and fusion devices, maxillofacial implants including cranial bone fixation devices, artificial bone replacements, dental implants, orthopedic cements and glues comprised of polymers, resins, metals, alloys, plastics and combinations thereof, nails, screws, plates, fixator devices, wires and pins and the like that are used in such implants, and other orthopedic implant structures as would be known to those of ordinary skill in the art. As shown in FIG. 6A, for example, an orthopedic implant 610 in the form of hip stem 612 comprises a substrate 611 and porous layer 614. Porous layer 614 may comprise beads, fibers, wire mesh and/or other known materials and shapes thereof used to form porous layer 614. Nanostructured components can be applied to substrate 611 by any of the methods described herein to form nanostructured surfaces, as shown, for example in FIG. 1.

In particular, the present embodiment of the invention provides such orthopedic implantable devices with nanostructured components to enhance the interaction of the devices with the tissues, joints, cartilage, bones, and other bodily structures with which they make contact at the implantation site. The nanostructured components (e.g., nanofibers) can either be attached to the outer or inner surface of the implantable device, e.g., by growing the nanofibers directly on the outer and/or inner surface of the device, or by separately covalently attaching the fibers to the device surfaces. Nanostructures on the surface of implants can enhance bone growth reaction at the implant site by encouraging and enhancing proliferation of osteoblasts, versus fibroblasts and other undesirable cells. It is to be appreciated that the nanostructured (e.g., nanofiber, nanowires and/or nantube) surfaces of the present invention can be used to encourage and enhance the proliferation of other cell types as well, including, for example, myocytes, adipocytes, fibromyoblasts, ectodermal cell, muscle cells, chondrocytes, endothelial cells, pancreatic cells, hepatocytes, bile duct cells, bone marrow cells, neural cells, genitourinary cells and combinations thereof. Enhanced bone growth activity encourages good fixation of the implant over time, e.g., by enhancing osteoblast differentiation and matrix production, and prevents loosening from fibroblastic response. In addition, nanostructured surfaces on orthopedic implants can prevent infection at the implant site, e.g., by preventing the growth of bacteria and other infectious organisms such as viruses, viral spores and fungus. The shape and size of the nanofibers as well as their density on the implant surfaces can be varied to allow differentiation of cell types.

For example, as shown below in the Examples section, it has been shown that the three-dimensional network formed by depositing nanofibers (e.g., silicon nanowires) on an implant surface can be tuned precisely to optimize osteoblast adhesion, proliferation and function. Furthermore nanofibers offer an external surface that can easily be modified using any number of coating or functionalization chemistries (e.g., growth of nitride or carbide layers for improved strength and durability, growth of titanium oxide, Ag, Zn etc. layers for improved biocompatibility with existing implant materials (e.g., titanium), and/or growth of specific organosilanes to facilitate linkage chemistries such as hydrophobic and/or hydrophilic coatings, etc.) developed for attaching biomolecules. For example, the nanofiber surface can be functionalized with a coating material to render it hydrophobic, lipophobic, or amphiphobic. The coating material can comprise, for example, polymers, inorganic materials, organic materials, or organic/inorganic hybrid materials including, for example, Teflon®, Tri-sil, tridecafluoro 1,1,2,2, tetrahydrooctyl-1-trichlorosilane, a fluoride containing compound, a silane containing compound, PTFE, hexamethyldisilazane, an aliphatic hydrocarbon containing molecule, an aromatic hydrocarbon containing molecule, a halogen containing molecule and paralyene. Interestingly, it has been found that higher density nanofiber (e.g., nanowire) surfaces (e.g., using longer nanofibers) showed highest adhesion and proliferation followed by high density shorter nanofibers and lower density longer nanofibers. Without being bound to any particular theory, it is believed that this is because higher density, longer nanofibers provide high surface area at a nanolevel which promotes osteoblast adhesion and eventually proliferation. The plurality of nanofibers may comprise, for example, nanowires having an average length, for example, of from about 1 micron to at least about 500 microns, e.g. more preferably from about 5 microns to at least about 150 microns, e.g. more preferably from about 10 microns to at least about 125 microns, e.g. more preferably from about 25 microns to at least about 100 microns. The plurality of nanowires may comprise an average density on the one or more surfaces of the medical device implant, for example, of from about 1 nanowire per square micron to at least about 1000 nanowires per square micron, e.g. more preferably from about 1 nanowire per square micron to at least about 500 nanowires per square micron, e.g. more preferably from about 10 nanowires per square micron to at least about 250 nanowires per square micron, e.g. more preferably from about 10 to 25 nanowires per square micron to at least about 100 nanowires per square micron.

The present invention contemplates that coatings applied to the nanotubes and nanorods of the present invention may be chosen so that they dissolve at different times so as to expose the underlying drug at different or specific chosen times. The coatings may be made thicker or thinner, resulting in different exposure times for the underlying drugs. In one embodiment a first substance in the hollow core of the nanotube has slower release kinetics than the second substance coated on the nanotube. In this way, the second substance is released first and serves its purpose prior to the first substance inside the hollow nanotube core which has greater time to elute.

Nanostructures in accordance with the present invention may be functionalized to target a particular cell, tissue or organ. Techniques and chemistries are known for the precise drug delivery to a particular cell or organ, see for example Cotten et al. Methods Enzym. 217:618, 1993 the contents of which are hereby incorporated by reference in its entirety.

Contolled drug delivery may be accomplished by those techniques known in the art, such as Iontophoresis. Iontophoresis is a process of transportation of ions into the tissues by passage of electric current through a medium containing the ions using a suitable electrode polarity. In one embodiment in situ, ions with a positive charge(+) are driven into the skin at the anode and those with negative charge (−) at the cathode. The delivery process can be controlled by selectively activating an electro-release system and/or by adjusting the rate of release. Several systems of this nature are described in U.S. Pat. Nos. 5,876,741 and 5,651,979 which describe a system for delivering active substances into an environment using polymer gel networks. Another drug delivery system sutiable with one embodiment of the present invention is described in U.S. Pat. No. 5,797,898 to Santini, Jr. which discloses the use of switches provided on a microchip to control the delivery of drugs. Also contemplated are techniques disclosed in U.S. Pat. No. 5,368,704 which discloses the use of an array of valves formed on a monolithic substrate that can be selectively activated to control the flow rate of a substance through the substrate. The disclosures of each of the above U.S. patents (U.S. Pat. Nos. 5,368,704, 5,797,898, and 5,876,741) are hereby incorporated by reference in their entirety. One of ordinary skill in the art will be able to adjust the ionized state of the compound, i.e. drug or bioactive substance. Lignocaine is most effective iontophoretically at a pH range of 3.4-5.2 With iontophoresis transdermal permission is maximum at pH of 9.4 and above when it is mainly in the non-ionized state and at this pH, iontophoretic delivery is minimum. Also, the presence of extraneous ions maydecrease the iontophoretic delivery of the drug ions because these ions compete with the drug for the iontophoretic flux. Higher ionic strength of material subjected to iontophoretic current resulted in decreased iontophoretic transport of the material into the tissues as increase in ionic strength yields higher concentration of extraneous ions which compete for the electric current. Increased concentration of the charged molecule generally, but not always, yields increased concentration in the tissues.

In another embodiment the present invention contemplates a pharmaceutical composition within or on the nanotubes or nanorods. These compositions may also include other pharmaceutically acceptable excipients. The compositions may be in the form of tablets, suspensions, solutions, capsules, emulsions, or other pharmaceutically acceptable carriers. Pharmacetically acceptable carriers are known in the art.

Nanostructures that are nanotubes are a preferred embodiment for implant devices for the purpose of delivering drugs and other bioactive substances. Note that the present invention is not limited to orthopedic implants as substrates for nanotube drug delivery. All of the substrates, coatings and functionalities disclosed herein are suitable for this purpose. The size of the hollow core in the nanotube may be tailored by synthetic techniques to increase diameter to speed release or a shrink the diameter to hinder release of the material therein. As used herein "hollow" does not mean completely hollow. For example, in a nanotube having a length of 10 nm, only 5 nm of the length of the tube may be hollow, and the other 5 nm not hollow, capped, coated, filled, etc. A nanotube set on a structure or substrate may be hollow along some, most or all of its shaft. For example the nanotube may be attached to the substrate by a linking agent and the nanotube by chemistries occuring on a side of the nanotube. The nanotube may have a branch that is used to bond or attach to a substrate, either directly or through linking agents.

Nanowire "heterostructures" such as those disclosed herein and in Published Application US 20050054004 A1, published Mar. 10, 2005, the contents of which are hereby incorporated by reference in its entirety, allow for different functionalization and targeted delivery of different molecules, by "designing" the segments along the length of each nanowire. For example, different segments of the nanowires may be made of different materials, and the different materials may be chosen such that they have different affinities for different functional linking agents or functional moieties. In one non-limiting embodiment compositions for stimulating receptors may selectively be attached to a first segment of a nanowire and a DNA sequence can be attached to a second segment. In another embodiment DNA encoding an antigen can be attached to a segment and an immune system stimulating adjuvant molecule can be bonded to a second segment, and an antigen can be bonded to a third segment.

Any number of tracers or tags (such as rhodamine or semiconductor nanocrystal) may be used for confirmation of internalization and intracellular tracking of the nanowires.

Hollow nanoparticles such as disclosed in "Formation of hollow nanocrystals through the naoscale Kirkendall effect" by Yadong Yin, Robert M. Rioux, Can K. Erdonmez, Steven Hughes, Gabor A. Somorjai, and A. Paul Alivisatos in *Science,* 30 Apr. 2004, the contents of which are hereby incorporated by reference in its entirety for all purposes are particularly suitable for use in the coatings and composites of this invention.

In a preferred embodiment, the hollow core of a nanotube is loaded with a drug and the shell is coated and/or functionalized so that the tube targets a specific cell type, etc. This reslts in a directed drug delivery system, a so called "magic bullet".

Alternatively, or additionally, the nanofibers or other nanostructures can be embedded into the implant material to enhance the durability and resistance to wear that occurs in a load bearing implantation site, thereby preventing microdegradation and resultant debris in the joints. Further alternatively, the nanofibers can be formed into a highly dense bioengineered scaffold or mat and, in certain instances, can be used in lieu of an implant for, e.g., insertion (e.g., injection) into and treatment of widespread diseases such as delayed union and nonunion in fractures, false joints (including infected ones), arthroses of the big articulations of the body's members (e.g., femoral, knee, humeral, ankle etc.) and the like. The nanoscale bioengineered scaffold, which could be substantially three dimensional due to the high surface area of the nanostructured components (e.g., nanofibers), can be used as an osteogenesis stimulator to encourage osteoblast adhesion and proliferation at its insertion (e.g., injection) site at a fracture, joint etc. Examples of nanofiber mats or scaffolds which could be used in practicing this aspect of the current invention are described, for example, in co-pending and commonly assigned U.S. Ser. No. 60/634,472 filed Dec. 9, 2004, the entire contents of which are incorporated herein by reference. The bioengineered scaffold may also comprise a base membrane or matrix onto and/or into which the nanostructure components (e.g., nanofibers) are incorporated or deposited. The base membrane or matrix may comprise a variety of materials such as natural or synthetic polymers including electrically conducting polymers, metals, alloys, ceramics or glass fabrics, silicone, etc. The bioengineered scaffold can be impregnated or bound with drugs, cells (e.g., cells such as osteoblasts, chondrocytes, stem cells (all types, adult and embryonic) or endothelial cells), or other specific compounds such as RGD adhesion peptides, cell seeding compounds, bioactive molecules such as BMP-2, or other such compounds, such that when implanted, the compound(s) or cells encourage osseointegration and stimulate new bone formation.

The implants of this invention (and/or the nanofibers) may also be coated on the inside and/or outside with other materials to still further enhance their bio-utility. As used herein "coating" may includes both a partial covering and a complete covering. Examples of suitable coatings are medicated coatings, drug-eluting coatings, drugs or other compounds, hydrophilic coatings, smoothing coatings, collagen coatings, human cell seeding coatings, antiinfectives, hormones, analgesics, anti-inflammatory agents, growth factors, chemotherapeutic agents, anti-rejection agents, prostaglandins, proteins such as fibrin, fibrinogen, adhesion promoting peptides such as RDG peptides (described below) and combinations thereof, or any other organic, inorganic or organic/inorganic hybrid materials. For example, nanostructured surfaces on orthopedic implants can deliver drugs or other compounds to the implantation site. Drugs delivered from nanowires, for example, by elution, binding, dissolution, and/or dissolving of the nanowires themselves can prevent infection, enhance bone growth, prevent scar tissue, hyperproliferation, and prevent rejection of the implant. The above-described nanofiber coatings on the implant can provide a high surface area that helps the implant to retain these coatings. The coatings can be adsorbed directly to the nanostructured surface of the implant. Alternatively, the nanostructured surface may be provided with a linking agent which is capable of forming a link to the nanostructured components (e.g., nanofibers) as well as to the coating material which is applied thereto. In such cases, the coating may be directly linked to the nanostructured surface, e.g., through silane groups, or it may be coupled via linker binding groups or other appropriate chemical reactive groups to participate in linkage chemistries (derivitization) with linking agents such as, e.g., substituted silanes, diacetylenes, acrylates, acrylamides, vinyl compounds, styryls, silicon oxide, boron oxide, phosphorus oxide, N-(3-aminopropyl)3-mercapto-benzamide, 3-aminopropyl-trimethoxysilane, 3-mercaptopropyl-trimethoxysilane, 3-maleimidopropyl-trimethoxysilane, 3-hydrazidopropyl-trimethoxysilane, hydroxysuccinimides, maleimides, haloacetyls, pyridyl disulfides, hydrazines, ethyldiethylamino propylcarbodiimide, combinations thereof, and the like.

An orthopedic (or dental, etc.) implant according to the present invention may include an adhesion-promoting peptide, if desired. Peptides that promote adhesion between osteoblasts and a substrate, for example, integrin-binding peptides containing the Arginine-Glycine-Aspartic Acid (RGD) sequence [Puleo and Bizios, Bone 12, 271-276 (1991)], are known. Published PCT application WO 97/25999, entitled "Peptides for Altering Osteoblast Adhesion," describes specific peptides, including peptides incorporating the sequence KRSR, for enhancement of adhesion to substrates. Adhesion-promoting materials are typically used by attaching the peptide to the surface of a substrate to which adhesion is desired. WO 97/25999 teaches a technique for immobilizing peptides on the surface of a substrate by a silanization reaction. Substrates include conventional orthopedic implants composed of titanium metal or other conventional materials. This technique or others known in the art may be used to immobilize adhesion-promoting peptides on the surface of implants containing nanofibers (e.g., nanowires) thereon.

Enhancement of long-term osteoblast functions, subsequent to adhesion of osteoblasts to material surfaces, is required for long-term osseointegration of orthopedic implants. Such functions include osteoblast proliferation, alkaline phosphatase synthesis and deposition of extracellular matrix calcium on the implant. It has been unexpectedly found that manufacturing an orthopedic implant to include nanofiber surfaces as described herein, and exposing the implant to osteoblast cells leads to enhancement of long-term functions and osseointegration of the implant, as demonstrated in the following Examples provided below.

XXV. Bioengineered Nerve Scaffolds and Virtual Extra-Cellular Matrix (VECM)

Damage to peripheral and central nerves occurs during trauma, other surgical procedures, and injury. Typically, pieces of a patient's own nerve (e.g., autograft) have been used to bridge the gap in a damaged nerve and provide a scaffold for nerve regeneration. These autografts are less than 50% effective. Attempts have been made to grow new peripheral nerves on artificial substrates typically impregnated with compounds to enhance nerve growth. New micro-devices to bridge the gap and induce nerve repair would be useful, especially in connection with spinal cord injuries and brain damage.

The present invention contemplates a nanoscale bioengineered scaffold or VECM (In some embodiments, the terms are interchangeable), which could be substantially three dimensional due to high surface area of the nanostructured components incorporated into and/or into the scaffold (e.g., nanofibers), to stimulate and encourage nerve cell growth. In addition, 3-D shaped nanostructures could encourage nerve regeneration. The bioengineered scaffold may comprise a base membrane or matrix onto and/or into which the nanostructure components (e.g., nanofibers, nanotubes and nanoparticles) are incorporated. The base membrane or matrix may comprise a variety of materials such as natural or synthetic polymers including electrically conducting polymers, metals, alloys, ceramics or glass fabrics, silicone, etc. A useful method for fabricating a suitable membrane or matrix from electrically conducting polymers, for example, which may be useful in the present invention is disclosed in U.S. Pat. Nos. 6,095,148 and 6,696,575, the entire contents of which are incorporated herein by reference.

The scaffold material and/or VECM may constitute nonwoven mesh or mat of nanostructures. By "non-woven mesh" it is meant that there is a plurality of nanostructures and that some nanostructures overlap at least partly, touching or not touching. The porosity may vary widely depending on the desired end use. The scaffold material may be blended or coated on a suitable support such as a polymeric film or polymeric beads. As described by Langer et al., J. Ped. Surg. 23(1), 3-9 (1988), WO88/03785 and EPA 88900726.6 by Massachusetts Institute of Technology, the contents of which are incorporated by reference herein, a matrix for implantation to form new tissue should be a pliable, non-toxic, porous template for vascular in-growth. The pores should allow vascular in-growth and the seeding of cells without damage to the cells or patient. These are generally interconnected pores in the range of between approximately 100 and 300 microns. The matrix should be shaped to maximize surface area, to allow adequate diffusion of nutrients and growth factors to the cells. In an exemplary embodiment, the matrix is formed of a bioabsorbable, or biodegradable, synthetic polymer such as polyesters, polyamides, polyethers, polythioethers, polyureas, polycarbonates, polycarbamides, proteins, polysaccharides, polyaryls, polyvinylpyrrolidones, etc. Non-limiting examples include polyesters synthesized from monomers selected from the group consisting of D, L-lactide, D-lactide, L-lactide, D, L-lactic acid, D-lactic acid, L-lactic acid, glycolide, glycolic acid, gamma.-butyrolactone, gamma.-hydroxy butyric acid, delta-valerolactone, delta.-hydroxy valeric acid, hydroxybutyric acids, and malic acid. Also included are poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g. PEO/PLA), polyalkylene oxalates, polyphosphazenes and biomolecules such as fibrin, fibrinogen, cellulose, starch, collagen and hyaluronic acid. The invention contemplates that both hydrophilic and hydrophobic block copolymers ma be used in some embodiments. Block copolymers may have hydrophobic A blocks (e.g., polyesters) and hydrophilic B block (e.g., polyethylene glycol). Other polymers could also be used in some embodiments if they can be dissolved and cured or polymerized such as polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; alkyd resins; polyoxymethylenes; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose. Non-degradable plastics and materials can also be used to form the matrix in some embodiments.

Alternatively, the scaffold can be made entirely of nanostructures such as, but not limited to, organic and inorganic nanocrystals as described above and below such as nanowires, nanodots, nanotetrapods, and other shapes on the nanoscale. The bioengineered scaffold can be impregnated or bound with drugs, cells (e.g., nerve cells such as Schwann cells, stem cells or embryonic cells), fibroblasts, or other specific compounds such as nerve growth factor (NGF), cell seeding compounds, neurotrophic growth factors (or genetically engineered cells producing such factors), VEGF, laminin or other such compounds, such that when implanted, the compound(s) encourage axonal elongation and functional nerve performance. Nerve explants also may be cultured and regenerated in vitro for implantation in vivo. For example, primary sciatic nerve explants may be isolated from mammalian tissue and cultured for example in high glucose DMEM supplemented with glucose, fetal bovine serum (FBS), sodium pyruvate, and NGF. Methods for isolating the sciatic nerve from 16-d chick embryos have been described in: Y.-W. Hu and C. Mezei, Can. J. Biochem., 49:320 (1971). Different compositions, including serum, serum substitutes, growth factors, such as nerve growth factor, hormones, and/or drugs can be used in the medium which are optimized for the particular nerve cell being cultured, to enhance proliferation and regeneration of nerve cells.

In one embodiment the coatings can be adsorbed directly to the nanostructured surface of the scaffold. The high surface area of the nanostructured components helps to retain the compound coatings on the scaffold. Alternatively, the nanostructured surface may be provided with a linking agent which is capable of forming a link to the nanostructured components (e.g., nanofibers) as well as to the coating material which is applied thereto. In such cases, the coating containing the desired compounds may be directly linked to the nanostructured surface, e.g., through silane groups, or it may be coupled via linker binding groups or other appropriate chemical reactive groups to participate in linkage chemistries (derivitization) with linking agents as described previously.

The nanofibers (or other nanostructured components) on the scaffold surfaces can optionally be embedded in a slowly-soluble biocompatible polymer (or other) matrix disclosed and described herein to alter nanofiber surfaces depending on the desired end use. For example, the polymer matrix can protect most of the length of each nanofiber, leaving only the ends uncovered. In one embodiment water soluble polymers are used in a number of different ways. For example, polymer chains can be formed in situ in a dilute aqueous solution primarily consisting of a monomer and an oxidizing agent. In this case, the polymer is actually created in the solution and subsequently spontaneously adsorbed onto the nanofiber surfaces as a uniform, ultra-thin film of between approximately 10 to greater than 250 angstroms in thickness, more preferably between 10 and 100 angstroms.

Nerve gaps to be treated with such scaffold devices can range in size from between about 5 mm to about 50 mm, for example between about 10 to about 30 mm, for example between about 20 mm to 30 mm. The scaffold devices can be made in a range of sizes and configurations to fit the application, and the nanostructures can be doped as necessary to provide enhanced electrical conductivity to transmit electrical nerve signals to nerve fibers. The scaffold devices may be implanted in vivo into a patient in need of therapy to repair or replace damaged cells or tissue, such as nervous system tissue. Materials which can be used for implantation include sutures, tubes, sheets, adhesion prevention devices (typically films, polymeric coatings applied as liquids which are polymerized in situ, or other physical barriers), and wound healing products (which vary according to the wound to be healed from films and coating to support structures).

To enhance the effectiveness of the treatment, compositions which further promote nervous tissue healing, such as proteins, antibodies, nerve growth factors, hormones, and attachment molecules, can be applied together with the scaffold, and as discussed above optionally can be covalently attached to the nanofibers and/or the scaffold support material. Those skilled in the art can readily determine exactly how to use these materials and the conditions required without undue experimentation. The scaffold may be implanted adjacent to or seeded with cells which are to be affected. The scaffold device is optionally electrically connected to a source of voltage or current. The electrical connection can be, for example, needles which are inserted to contact the scaffold, or electrodes attached to the nanostructured surfaces or scaffold membrane which can be externally connected to an appropriate electrical power source. Voltage or current may be applied to the nanostructures and/or scaffold membrane in a range which induces the desired effect on the cells while not damaging the cells.

It is in known that embryonic stem (ES) cells, transplanted into mouse hearts damaged by experimentally induced heart attacks formed functional forms of the major cell types that comprise a healthy heart. In essence healthy heart cells and tissue was synthesized using engineered ES cells. The present invention contemplates incorporating engineered stem cells into a biostable, biocompatible "scaffold" with tunable properties of size, porosity and surface chemistry that promote the formation of the desired tissue. This in effect entails the creation of a virtual extra-cellular matrix (VECM) or a biological scaffold. While biodegradable scaffolds (including polymer scaffolds, though the invention is not so limited to the material comprising the scaffold) have been proposed for such applications, the prior art scaffolds aren't easily tunable in their biological response and they lack the size/surface area advantages of the present invention.

The present invention, in one embodiment, uses a "bottom-up" synthetic method to build a biomimetic VECM or scaffold using the nanostructures described herein. This nanostructure comprises materials chosen such that the nanostructure has the ablity to interact with biology at the nano size scale. Exploiting control of material science at the nanometer scale, VECM's in accordance with the present invention can be designed to mimic the tissue integrating characteristics of collagen fiber matrices to promote adhesion and accelerated tissue integration while also readily allowing the creation of complex 3-D geometries useful for practical employment in vivo.

Figure 16A:
FIGS. 16A-B show histological staining inllustrating enhanced bone integration with VECM.
Figure 16B:
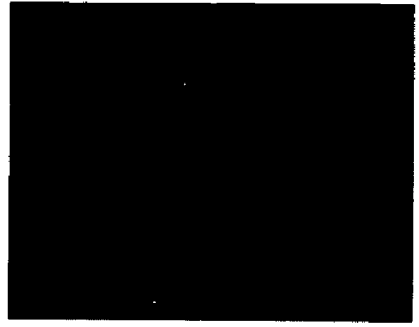

The present inventors have demonstrated accelerated in vivo tissue integration of bone with this VECM coating by mimicking the structure of collagen in the extra-cellular matrix (see FIG. 16A and FIG. 16B). FIG. 16A and FIG. 16B shows the histological staining illustrating enhanced bone integration with VECM. FIG. 16A is a control sample without a VECM coating; the dark area is the implant. FIG. 16B shows the implant with VECM. The darkened portion stained and indicates enhanced bone growth around the implant.

According to one embodiment of the present invention the directed conversion of ES cells into endothelial cells with the specifically engineered VECM may accomplish this goal. It is known in the art that a mixture of vascular endothelial growth factor (VEGF), basic fibroblast growth factor (bFGF), insulin-like growth factor (IGF), and epidermal growth factor (EGF) may be used to promote ES cell to endothelial cell conversion. The present invention contemplates that a variety of growth factors, including these can be readily incorporated into the VECM technology of the present invention. In another embodiment the VECM may be used as a coating in implants to ensure proper endothelialization. In another embodiment artificial blood vessels could be fabricated that would form completely natural vessels once placed into the body.

It will be appreciated that the aggregate of many wires form a VECM of the present invention and thus in a preferred embodiment is analogous to a web or mesh of collagen fiber or fibril. The chemistries for functionalizations and linking agents for the various coatings, drugs and other therapeutic agents useful in the nanotubes, nanowires, hollow nanotubes and nanoparticles, and for VECM and bioscaffolds are interchangeable depending on the desired end use. For example, the invention contemplates growing nanowires on a coil for an aneurysm treatment and coating the wires with fibrinogen, then applying a coating of poly-lactic acid copolymer or other biodegradable polymer. Alternatively, a fibrous mat of fibers may be synthesized as described herein to create a bioscaffold, the fibrous mat of fibers coated with fibrinogen and poly-lactic acid, and the fibrous mat applied to the coil.

In another embodiment of the present invention the VECM and the bioscaffolds of the present invention may be synthesized to have gecko adhesive properties. This embodiment may be particularly useful for EVAR or an adhesive patch for drug delivery in the eye.

The present invention will enable the facile creation of complex tissue geometries both in-vitro and in-vivo. Engineering at the nanoscale in accordance with the present invention will make possible a tunable platform hospitable to a desired tissue type with control over all aspects of the matrix including: size, geometry, porosity, stability, compatibility, surface chemistry and elution of chemistries such as growth factors.

Timed dosages and release using two or more compounds synergistically is known in the art, for example Nakayama et al., Blood, Vol. 95 No. 7 (April 1), 2000: pp. 2275-2283 (the contents of which are hereby incorporated herein by reference in its entirety). When combined with BMP-4, 2 to 20 ng/mL VEGF synergistically augmented the BMP-4-dependent generation of erythro-myeloid CFCs and lymphoid progenitors from ES cells, which were enriched in $CD34^+$ $CD31^{lo}$ and $CD34^+$ CD45 cell populations, respectively, in a dose-dependent manner. During the 7 days of in vitro differentiation, BMP-4 was required within the first 4 days, whereas VEGF was functional after the action of BMP-4 (in the last 3 days). Thus, timed release of the compositions in accordance with some embodiments of the present invention disclosed herein are important.

Growth factors suitable for inclusion with the present invention include but are not limited to basic fibroblast growth factor, epidermal growth factor, insulin-like growth factor, platelet-derived growth factor, placental growth factor and endothelial growth factor (VEGF).

In one embodiment of the present invention there is contemplated a method for controlling differentiation of stem cells (includes all types of stem cells, adult and embryonic), said method comprising providing a substrate for growing cells said substrate comprising a plurality of nanostructures, a population of stem cells, and at least one growth factor compound capable of promoting cell reproduction. The population of stem cells and the growth factor may be associated with the substrate containing the nanostructures in a variety of ways according to the present invention. Preferably the substrate containing the nanostructures is a VECM according to the present invention. The different growth factors may be incorporated into the VECM as set forth herein.

XXVI) Nanofiber Surface Substrates and Composite Coatings

As noted previously, increased surface area is a property that is sought after in many fields (e.g., in substrates for assays or separation column matrices). For example, fields such as tribology and those involving separations and adsorbents are quite concerned with maximizing surface areas. The current invention offers surfaces and applications having increased or enhanced surface areas (i.e., increased or enhanced in relation to structures or surfaces without nanofibers).

As used herein "nanostructured surface" includes all surfaces having at least one nanostructure thereon or associated therewith. This includes films, substrates, coatings, sheets, woven and non-woven mats and mesh having a plurality of nanostructures thereon. As used herein, "nanostructure" is meant to include nanowires, nanorods, nanotubes and nanoparticles synthesized as set forth herein, as well as those nanostructures described and synthesized in Somorjai, G. et al., J. Phys. Chem. B 2003, 107, 3340-3343, the contents of which are hereby incorporated herein by reference in its entirety. As used herein a surface having nanostructures thereon may also be termed herein "nanostructured film", "nanostructured coating" or "nanostructured sheet".

A "nanofiber enhanced surface area" herein corresponds to a substrate comprising a plurality of nanofibers (e.g., nanowires, nanotubes, etc.) attached to the substrate so that the surface area within a certain "footprint" of the substrate is increased relative to the surface area within the same footprint without the nanofibers. In typical embodiments herein, the nanofibers (and often the substrate) are composed of silicon oxides. It will be noted that such compositions convey a number of benefits in certain embodiments herein. Also, in many preferred embodiments herein, one or more of the plurality of nanofibers is functionalized with one or more moiety.

See, below. However, it will also be noted that the current invention is not specifically limited by the composition of the nanofibers or substrate, unless otherwise noted.

As used herein "coating", "coatings", "coated" and "coat" are forms of the same term defining material and process for making a material where a first substance is at least partially covered or associated with a second substance. Both the first and second substance do not have to be different. Further, when a nanostructure is "coated" as used herein, the coating may be may be effectuated by any chemical or mechanical bond or force, including linking agents. Thus a nanowire comprising a first substance may be "coated" with a second substance via a linking agent that is a third substance. As used herein, the "coating" need not be complete or cover the entire surface of the first substance to be "coated". The "coating" may be complete as well, i.e. completely covering the first substance. There may be multiple coatings and multiple substances within each coating. Also, the invention contemplates that a "coating" is complete if a nanowire is composed of two or three or more different materials, such as a heterostructure, and there are two or more different materials functionalized onto the same nanowires.

By "the plurality of nanostructures are dispersed in the matrix material" it is meant that at least some of the nanostructures are embedded in the matrix material. All of the nanostructures need not be totally embedded. The dispersion need not be uniform, though in some embodiments this substantial uniformity of dispersion is preferred.

Coatings contemplated in accordance with the present invention comprise "pharmaceutical agents" and include, but not limited to medicated coatings, drug-eluting coatings, drugs or other compounds, hydrophilic coatings, smoothing coatings, collagen coatings, human cell seeding coatings, antiinfectives, hormones, analgesics, anti-inflammatory agents, growth factors, chemotherapeutic agents, anti-rejection agents, prostaglandins, pharmaceutically acceptable carriers, proteins such as fibrin, fibrinogen, adhesion promoting peptides such as RDG peptides (described below) and combinations thereof, or any other organic, inorganic or organic/inorganic hybrid materials. In some embodiments the coating comprises nanostructures. Thus the invention contemplates nanostructures on nanostructures, for example nanoparticles on nanowires. For example, in a preferred embodiment for anti-infective properties, i.e. anti-bacterial, Ag and/or Zn (or other nanoparticles having antibacterial properties) nanoparticles are "coated" on a nanowires, i.e. the nanoparticles are deposited onto a nanowire in any desired density.

In some preferred embodiments the coatings and compositions disclosed herein are flowable. These are useful for injecting into the human body, as a wound dressing or a bone paste, for example. The term "flowable" means able to flow without external pressure. In a preferred embodiment, as used herein, a material that is "flowable" at a temperature between 19-50° C. and 1 atm, is sufficiently viscous and having sufficient adhesive and cohesive properties as not to substantially flow spontaneously (e.g. gravity-induced flow) without the application of an external pressure to overcome the material's flow-resistance due to the above-stated properties. Preferably, as used herein, a "flowable" composition has a viscosity at body temperature and pressure of at least 10 cP, preferably at least 100 cP, preferably at least 1,000 cP, preferably at least 10,000 cP. In one embodiment there is disclosed a bone paste made of compositions containing nanostructures therein. The bone paste may be made flowable at different rates by changing the viscosity of the composition.

In one embodiment of the invention there is contemplated coated nanostructures and compositions comprising composite coatings containing nanostructures therein. The composite coatings may be deposited on or formed on substrates including medical devices. In one embodiment the composite coatings comprise a matrix material and at least one nanostructure. A plurality of nanostructures, either the same or different, are preferred. Preferably the nanostructures comprise a material or has a material coated or associated therewith having a biological function (pharmaceutical agent) such as a nanoparticle comprising Ag which is useful for antibacterial properties. For example, the nanostructure may comprise Ag and/or Zn (in any oxidation state, alloy or a composition capable or releasing metal ions in situ, including $Ag_2O$), or have metal nanoparticles deposited (or coated or associated therewith) on a nanostructure. Nanostructures such as nanotubes (coated inside and/or out) are preferred, more preferred are nanoparticles. The nanoparticles may be coated with multiple coatings if desired. The different layered coatings may serve different functions. As non-limiting examples, growth factors or peptides (for example BMP, VEGF, IKVAV) may be attached to nanowires. Bone morphogenic protenin may be added for bone integration. Vascular endothelial growth factor (VEGF) may be added for endothelialization. Peptides such as IKVAV may be added to attach nerves and have those express neuritis. Other coatings comprise tracers.

In one embodiment the nanowires comprise a silicon oxide and/or silicon dioxide shell. It is contemplated that the coating could comprise fired $CaCO_3$ or calcium polyphosphate with known bone integration properties.

The matrix material may be a polymer or other substance. The polymer may be either a biostable or a bioabsorbable polymer depending on the desired rate of release or the desired degree of polymer stability, but a bioabsorbable polymer is preferred since, unlike a biostable polymer, it will not be present long after implantation to cause any adverse, chronic local response. The prior art has used polymer composites to deliver drugs, see for example U.S. Pat. No. 5,605,696, the contents of which are hereby incorporated by reference in its entirety.

In one embodiment of the present invention, fast dissolving polymers are used for the biodegradable polymer. Also, combinations of different polymers or similar polymers with definite molecular weight characteristics may be used in order to achieve preferred film forming capabilities, mechanical properties, and kinetics of dissolution. Polyethylene glycol (PEG) is a water-soluble, waxy solid that is used extensively in the cosmetic and toiletry industry. It is very soluble having a solubility of greater than 1 g/100 mL $H_2O$ at 21° C. As the molecular weight of PEG increases, viscosity and freezing point increase. PEG 600 is used in WAXWORKS experiments due to its freezing point just below room temperature (about 19.5° C.). Although PEG is water soluble, solubility is greatly reduced at temperatures approaching 0° C., allowing experiments to run for 15-20 minutes before dissolution of PEG becomes pronounced. At higher temperatures (above 10° C.) this length of time is much shorter.

Matrix materials for the composite coating in according with the present invention may include a bioabsorbable, or biodegradable, synthetic polymer such as polyesters, polyamides, polyethers, polythioethers, polyureas, polycarbonates, polycarbamides, proteins, polysaccharides, polyaryls, polyvinylpyrrolidones (PVP), etc. Non-limiting examples include polyesters synthesized from monomers selected from the group consisting of D, L-lactide, D-lactide, L-lactide, D, L-lactic acid, D-lactic acid, L-lactic acid, glycolide, glycolic acid, gamma.-butyrolactone, gamma.-hydroxy butyric acid, delta-valerolactone, delta-hydroxy valeric acid, hydroxybutyric acids, and malic acid. Also included are poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g. PEO/PLA), polyalkylene oxalates, polyphosphazenes and biomolecules such as fibrin, fibrinogen, cellulose such as hydroxypropyl cellulose, hydroxypropylmethyl cellulose, or hydroxyethyl cellulose, starch, $TiO_2$, Si, $SiO_2$, $CaCO_3$, collagen and hyaluronic acid The PVP can be N-vinyl pyrrolidone, 3-methyl N-vinylpyrrolidone, N-vinyl amide pyrrolidone, N-vinyl acetate pyrrolidone, vinylpyrrolidone-vinyl acetate copolymer, and/or acrylamide-vinylpyrrolidone co-polymer.

Preferably the matrix material dissolves over time. By "dissolves over time" it is meant that the matrix material will dissolve, evaporate, disintegrate or otherwise engage in some physical or chemical process that will cause it to substantially disappear from the site applied. "Over time" is a relative term; one skilled in the art will be able to tailor a material that will dissolve in situ depending on the appropriate conditions. Combinations of different polymers or similar polymers with definite molecular weight characteristics may be used in order to achieve preferred film forming capabilities, mechanical properties, and kinetics of dissolution. In order to modify the water dissolution kinetics of the backing layer without resulting in a non-water soluble material, partial and limited crosslinking may be used. Crosslinking agents known in the art are appropriate for use in the invention and may include glyoxal, propylene glycol, glycerol, dihydroxy-polyethylene glycol of different sizes, and butylene glycol. U.S. Pat. No. 6,159,498, the contents of which are incorporated herein by reference in its entirety, discloses some non-limiting examples of biodegradable polymers useable for some embodiments of the present invention.

The invention contemplates that both hydrophilic and hydrophobic block copolymers may be used in some embodiments. Block copolymers may have hydrophobic A blocks (e.g., polyesters) and hydrophilic B block (e.g., polyethylene glycol).

Other polymers could also be used in some embodiments if they can be dissolved and cured or polymerized such as polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; alkyd resins; polyoxymethylenes; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

The ratio of matrix material (esp. matrix polymer) to nanostructure will depend in one embodiment on the the rate at which the coating is to release the nanostructure to the tissue. More polymer may be needed in order to provide an elution matrix that limits the elution of a very soluble nanostructure. A wide ratio of nanostructure to matrix material mixture is contemplated ranging from about 0.01 to 95 wt %, or about 0.1 to about 80 wt %, or about 0.2 to about 50 wt %, or about 0.5 to about 10 wt %, preferably 1 wt % to about 5 wt %.

In one embodiment the matrix material comprises $SiO_2$.

The matrix polymer is chosen based on the entrapment and release kinetics of the active agent. In one embodiment the active agent is covalently linked to the polymer matrix. To covalently link the agent to be delivered to the polymer matrix, the polymer may be chemically activated using any technique known in the art. The activated polymer is then mixed with the agent under suitable conditions to allow a covalent bond to form between the polymer and the agent. In one example, a nucleophile, such as a thiol, hydroxyl group, or amino group, on the agent attacks an electrophile (e.g., activated carbonyl group) on the polymer to create a covalent bond.

The coating and/or bioscaffolds of the present invention may be prepared or further processed after or during synthesis using micromolding, electro-deposition machining, laser ablation, laser drilling, micromachining, wet etching, reactive ion etching, and embossing.

In one embodiment of the present invention there is contemplated coatings comprising "tracers". "Tracers" as used herein means materials capable of being detected either ex situ and/or in situ. One having skill in the art will appreciate which tracers are suitable for a particular purpose and what detection means are practical for detecting the tracers. Nanostructures made in accordance with the present invention, particulary nanodots and nanowires, are capable of stimulated emission over a range of wavelengths. One skilled in the art knows how to synthesize a nanostructure that will emit a desired wavelength of radiation, or a plurality of nanostructures, or arrays of nanostructures that will emit desired wavelengths of radiation by varying the composition and/or thickness of the nanostructures. Nanostructured surfaces in accordance with this embodiment may be coated or uncoated and functionalized or unfunctionalized. The invention contemplates arrays comprising substrates having thereon nanostructures wherein the substrate has multiple areas having either different nanostructures, or different functionalization or coating, or combinations of the above. The arrays could serve a variety of analytical uses, both in situ and ex situ. The array or microarry according to one embodiment of the present invention may comprise a woven mat, nonwoven mat, fibrous mat or mess of nanofibers or nanotubes. This embodiment may comprise an auxiliary substrate, but it is not required.

In one embodiment nanostructures or medical devices containing nanostructures or having nanostructures thereon may comprise a coating of fibrin. Preferably the fibrin is partially or wholly encapsulated by a biocompatable polymer such as polyglycolic acid, poly-L-lactic acid, poly-DL-lactic acid, poly-D-lactic acid, poly(lactic acid-glycolic acid) copolymer, poly-epsilon-caprolactone, poly(glycolic acid-caprolactone) copolymer, polyamino acid, polyanhydride, polyorthoester, and copolymers and mixtures thereof. It is preferable to use compositions that are accepted by the Food and Drug Administration (FDA) and have been used as a biodegradable polymer, which can be used in a human body.

The various embodiments of the current invention are adaptable to, and useful for, a great number of different applications. For example, as explained in more detail below, various permutations of the invention can be used in, e.g., binding applications (e.g., microarrays and the like), separations (e.g., bioscaffolds (e.g., as a base for cell culture and/or medical implants, optionally which resist formation of biofilms, etc.), and controlled release matrices, etc. Other uses and embodiments are examined herein.

Examined herein, are other beneficial uses of various embodiments of the current invention. For example, the distinct morphology of the nanofiber surfaces herein can be utilized in numerous biomedical applications such as scaffolding for growth of cell culture (both in vitro and in vivo). In vivo uses can include, e.g., aids in bone formation, etc. Additionally, the surface morphology of some of the embodiments produces surfaces that are resistant to biofilm formation and/or bacterial/microorganism colonization. Other possible biomedical uses herein, include, e.g., controlled release matrices of drugs, etc. See, above.

As also will be appreciated by those of skill in the art, many aspects of the current invention are optionally variable (e.g., surface chemistries on the nanofibers, surface chemistries on any end of the nanofibers or on the substrate surface, etc.). Specific illustration of various modifications, etc. herein, should therefore not be taken as limiting the current invention. Also, it will be appreciated, and is explained in more detail below, that the length to thickness ratio of the nanofibers herein is optionally varied, as is, e.g., the composition of the nanofibers. Furthermore, a variety of methods can be employed to bring the fibers in contact with surfaces. Additionally, while many embodiments herein comprise nanofibers that are specifically functionalized in one or more ways, e.g., through attachment of moieties or functional groups to the nanofibers, other embodiments comprise nanofibers that are not functionalized XXVII) Nanofibers and Nanofiber Construction In typical embodiments herein the surfaces (i.e., the nanofiber enhanced area surfaces) and the nanofibers themselves can optionally comprise any number of materials. The actual composition of the surfaces and the nanofibers is based upon a number of possible factors. Such factors can include, for example, the intended use of the enhanced area surfaces, the conditions under which they will be used (e.g., temperature, pH, presence of light (e.g., UV), atmosphere, etc.), the reactions for which they will be used (e.g., within a patient, etc.), the durability of the surfaces and the cost, etc. The ductility and breaking strength of nanowires will vary depending on, e.g., their composition. For example, ceramic ZnO wires can be more brittle than silicon or glass nanowires, while carbon nanotubes may have a higher tensile strength.

As explained more fully below, some possible materials used to construct the nanofibers and nanofiber enhanced surfaces herein, include, e.g., silicon, ZnO, TiO, carbon, carbon nanotubes, glass, and quartz. See, below. The nanofibers of the invention are also optionally coated or functionalized, e.g., to enhance or add specific properties. For example, polymers, ceramics or small molecules can optionally be used as coating materials. The optional coatings can impart characteristics such as water resistance, improved mechanical or electrical properties or specificities for certain analytes. Additionally, specific moieties or functional groups can also be attached to or associated with the nanofibers herein.

Of course, it will be appreciated that the current invention is not limited by recitation of particular nanofiber and/or substrate compositions, and that, unless otherwise stated, any of a number of other materials are optionally used in different embodiments herein. Additionally, the materials used to comprise the nanofibers can optionally be the same as the material used to comprise the substrate surfaces or they can be different from the materials used to construct the substrate surfaces.

In yet other embodiments herein, the nanofibers involved can optionally comprise various physical conformations such as, e.g., nanotubules (e.g., hollow-cored structures), etc. A variety of nanofiber types are optionally used in this invention including carbon nanotubes, metallic nanotubes, metals and ceramics.

It is to be understood that this invention is not limited to particular configurations, which can, of course, vary (e.g., different combinations of nanofibers and substrates and optional moieties, etc. which are optionally present in a range of lengths, densities, etc.). It is also to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "a nanofiber" optionally includes a plurality of such nanofibers, and the like. Unless defined otherwise, all scientific and technical terms are understood to have the same meaning as commonly used in the art to which they pertain. For the purpose of the present invention, additional specific terms are defined throughout.

A) Nanofibers

The term "nanofiber" as used herein, refers to a nanostructure typically characterized by at least one physical dimension less than about 1000 mm, less than about 500 nm, less than about 250 nm, less than about 150 nm, less than about 100 nm, less than about 50 nm, less than about 25 nm or even less than about 10 mm or 5 nm. In many cases, the region or characteristic dimension will be along the smallest axis of the structure.

Nanofibers of this invention typically have one principle axis that is longer than the other two principle axes and, thus, have an aspect ratio greater than one, an aspect ratio of 2 or greater, an aspect ratio greater than about 10, an aspect ratio greater than about 20, or an aspect ratio greater than about 100, 200, or 500. In certain embodiments, nanofibers herein have a substantially uniform diameter. In some embodiments, the diameter shows a variance less than about 20%, less than about 10%, less than about 5%, or less than about 1% over the region of greatest variability and over a linear dimension of at least 5 nm, at least 10 nm, at least 20 nm, or at least 50 nm. For example, a wide range of diameters could be desirable due to cost considerations and/or to create a more random surface. Typically the diameter is evaluated away from the ends of the nanofiber (e.g. over the central 20%, 40%, 50%, or 80% of the nanofiber). In yet other embodiments, the nanofibers herein have a non-uniform diameter (i.e., they vary in diameter along their length). Also in certain embodiments, the nanofibers of this invention are substantially crystalline and/or substantially monocrystalline. The invention contemplates diameters that have different cross sectional areas, and different cross sectional shapes, i.e. triangular, round, elliptical, complex, irregular, etc. and/or combinations thereof.

It will be appreciated that the term nanofiber, can optionally include such structures as, e.g., nanowires, nanowhiskers, semi-conducting nanofibers, carbon nanotubes or nanotubules and the like The nanofibers can comprise "pure" materials, substantially pure materials, doped materials and the like and can include insulators, conductors, and semiconductors. Additionally, while some illustrative nanofibers herein are comprised of silicon (or silicon oxides), as explained above, they optionally can be comprised of any of a number of different materials, unless otherwise stated. Composition of nanofibers can vary depending upon a number of factors, e.g., specific functionalization (if any) to be associated with or attached to the nanofibers, durability, cost, conditions of use, etc. The composition of nanofibers is quite well known to those of skill in the art. Some embodiments herein comprise nanofibers composed of one or more organic or inorganic compound or material. Any recitation of specific nanofiber compositions herein should not be taken as limiting.

Additionally, the nanofibers of the invention are optionally constructed through any of a number of different methods, and examples listed herein should not be taken as limiting. Thus, nanofibers constructed through means not specifically described herein, but which fall within the parameters as sets forth herein are still nanofibers of the invention and/or are used with the methods of the invention.

In a general sense, the nanofibers of the current invention often (but not exclusively) comprise long thin protuberances (e.g., fibers, nanowires, nanotubules, etc.) grown from a solid, optionally planar, substrate. Of course, in some embodiments herein the nanofibers are deposited onto their ultimate substrates, e.g., the fibers are detached from the substrate on which they are grown and attached to a second substrate. The second substrate need not be planar and, in fact, can comprise a myriad of three-dimensional conformations, as can the substrate on which the nanofibers were grown originally. In some embodiments herein, the substrates are flexible. Also, as explained in greater detail below, nanofibers of the invention can be grown/constructed in, or upon, variously configured surfaces, e.g., within capillary tubes, shunts, etc. See, infra.

In various embodiments herein, the nanofibers involved are optionally grown on a first substrate and then subsequently transferred to a second substrate which is to have the enhanced surface area. Such embodiments are particularly useful in situations wherein the substrate desired needs to be flexible or conforming to a particular three-dimensional shape that is not readily subjected to direct application or growth of nanofibers thereon. For example, nanofibers can be grown on such rigid surfaces as, e.g., silicon wafers or other similar substrates. The nanofibers thus grown can then optionally be transferred to a flexible backing such as, e.g., rubber or the like. Again, it will be appreciated, however, that the invention is not limited to particular nanofiber or substrate compositions. For example, nanofibers are optionally gown on any of a variety of different surfaces, including, e.g., flexible foils such as aluminum or the like. Additionally, for high temperature growth processes, any metal, ceramic or other thermally stable material is optionally used as a substrate on which to grow nanofibers of the invention. Furthermore, low temperature synthesis methods such as solution phase methods can be utilized in conjunction with an even wider variety of substrates on which to grow nanofibers. For example, flexible polymer substrates and other similar substances are optionally used as substrates for nanofiber growth/attachment.

As one example, the growth of nanofibers on a surface using a gold catalyst has been demonstrated in the literature. Applications targeted for such fibers are based on harvesting them from the substrate and then assembling them into devices. However, in many other embodiments herein, the nanofibers involved in enhanced surface areas are grown in place. Available methods, such as growing nanofibers from gold colloids deposited on surfaces are, thus, optionally used herein. The end product which results is the substrate upon which the fibers are grown (i.e., with an enhanced surface area due to the nanofibers). As will be appreciated, specific embodiments and uses herein, unless stated otherwise, can optionally comprise nanofibers grown in the place of their use and/or through nanofibers grown elsewhere, which are harvested and transferred to the place of their use. For example, many embodiments herein relate to leaving the fibers intact on the growth substrate and taking advantage of the unique properties the fibers impart on the substrate. Other embodiments relate to growth of fibers on a first substrate and transfer of the fibers to a second substrate to take advantage of the unique properties that the fibers impart on the second substrate.

For example, if nanofibers of the invention were grown on, e.g., a non-flexible substrate (e.g., such as some types of silicon wafers) they could be transferred from such non-flexible substrate to a flexible substrate (e.g., such as rubber or a woven layer material). Again, as will be apparent to those of skill in the art, the nanofibers herein could optionally be grown on a flexible substrate to start with, but different desired parameters may influence such decisions.

A variety of methods may be employed in transferring nanofibers from a surface upon which they are fabricated to another surface. For example, nanofibers may be harvested into a liquid suspension, e.g., ethanol, which is then coated onto another surface. Additionally, nanofibers from a first surface (e.g., ones grown on the first surface or which have been transferred to the first surface) can optionally be "harvested" by applying a sticky coating or material to the nanofibers and then peeling such coating/material away from the first surface. The sticky coating/material is then optionally placed against a second surface to deposit the nanofibers. Examples of sticky coatings/materials, which are optionally used for such transfer, include, but are not limited to, e.g., tape (e.g., 3M Scotch® tape), magnetic strips, curing adhesives (e.g., epoxies, rubber cement, etc.), etc. The nanofibers could be removed from the growth substrate, mixed into a plastic, and then surface of such plastic could be ablated or etched away to expose the fibers.

The actual nanofiber constructions of the invention are optionally complex. The nanofibers can form a complex three-dimensional pattern. The interlacing and variable heights, curves, bends, etc. form a surface which greatly increases the surface area per unit substrate (e.g., as compared with a surface without nanofibers). Of course, in other embodiments herein, it should be apparent that the nanofibers need not be as complex. Thus, in many embodiments herein, the nanofibers are "straight" and do not tend to bend, curve, or curl. However, such straight nanofibers are still encompassed within the current invention. In either case, the nanofibers present a non-tortuous, greatly enhanced surface area.

B) Functionalization

Some embodiments of the invention comprise nanostructures including nanofiber and nanofiber enhanced area surfaces in which the fibers include one or more functional moiety (e.g., a chemically reactive group) attached to them. The term "coating" used herein will also include functional moieties and their optional linking agents. Functionalized nanofibers are optionally used in many different embodiments, e.g., to confer specificity for desired analytes in reactions such as separations or bioassays, etc. Beneficially, typical embodiments of enhanced surface areas herein are comprised of silicon oxides, which are conveniently modified with a large variety of moieties. Of course, other embodiments herein are comprised of other nanofiber compositions (e.g., polymers, ceramics, metals that are coated by CVD or sol-gel sputtering, etc.) which are also optionally functionalized for specific purposes. Those of skill in the art will be familiar with numerous functionalizations and functionalization techniques which are optionally used herein.

For example, details regarding relevant moiety and other chemistries, as well as methods for construction/use of such, can be found, e.g., in Hermanson Bioconjugate Techniques Academic Press (1996), Kirk-Othmer Concise Encyclopedia of Chemical Technology (1999) Fourth Edition by Grayson et al. (ed.) John Wiley & Sons, Inc., New York and in Kirk-Othmer Encyclopedia of Chemical Technology Fourth Edition (1998 and 2000) by Grayson et al. (ed.) Wiley Interscience (print edition)/John Wiley & Sons, Inc. (e-format). Further relevant information can be found in CRC Handbook of Chemistry and Physics (2003) 83$^{rd}$ edition by CRC Press. Details on conductive and other coatings, which can also be incorporated onto nanofibers of the invention by plasma methods and the like can be found in H. S. Nalwa (ed.), Handbook of Organic Conductive Molecules and Polymers, John Wiley & Sons 1997. See also, ORGANIC SPECIES THAT FACILITATE CHARGE TRANSFER TO/FROM NANOCRYSTALS U.S. Ser. No. 60/452,232 filed Mar. 4, 2003 by Whiteford et al., U.S. Published Application No. 2005 0205850 A1, published Sep. 22, 2005 and assigned to the assignee of the present application, the contents of which are incorporated herein by reference in its entirety. Details regarding organic chemistry, relevant for, e.g., coupling of additional moieties to a functionalized surface of nanofibers can be found, e.g., in Greene (1981) Protective Groups in Organic Synthesis, John Wiley and Sons, New York, as well as in Schmidt (1996) Organic Chemistry Mosby, St Louis, Mo., and March's Advanced Organic Chemistry Reactions, Mechanisms and Structure, Fifth Edition (2000) Smith and March, Wiley Interscience New York ISBN 0-471-58589-0. Those of skill in the art will be familiar with many other related references and techniques amenable for functionalization of NFS herein.

The terms "polypeptide" and "protein" are used interchangeably herein and refer to a polymeric form of amino acids of any length, which can include coded and non-coded amino acids, chemically or biochemically modified or derivatized amino acids, and polypeptides having modified peptide backbones.

The term "Alkyl" refers to a branched, unbranched or cyclic saturated hydrocarbon group of 1 to 24 carbon atoms optionally substituted at one or more positions, and includes polycyclic compounds. Examples of alkyl groups include optionally substituted methyl, ethyl, n-propyl, isopropyl, n-butyl, s-butyl, t-butyl, n-pentyl, isopentyl, neopentyl, n-hexyl, n-heptyl, n-octyl, n-decyl, hexyloctyl, tetradecyl, hexadecyl, tetracosyl as well as cycloalkyl groups such as cyclopropyl, cyclobutyl, cyclopentyl, cyclohexyl, cycloheptyl, cyclooctyl, adamantyl, and norbornyl. The term "lower alkyl" refers to an alkyl group of 1 to 6 carbon atoms, preferably 1 to 4 carbon atoms. Substituents on substituted alkyl groups include hydroxyl, cyano, halogen, haloalkyl, heteroalkyl, carboxyalkyl, amine, amide, thioether and —SH.

The term "Alkoxy" refers to an "—Oalkyl" group, where alkyl is as defined above. A "lower alkoxy" group intends an alkoxy group containing one to six, more preferably one to four, carbon atoms.

The term "Alkenyl" refers to a branched, unbranched or cyclic hydrocarbon group of 2 to 24 carbon atoms containing at least one carbon-carbon double bond optionally substituted at one or more positions. Examples of alkenyl groups include ethenyl, 1-propenyl, 2-propenyl (allyl), 1-methylvinyl, cyclopropenyl, 1-butenyl, 2-butenyl, isobutenyl, 1,4-butadienyl, cyclobutenyl, 1-methylbut-2-enyl, 2-methylbut-2-en-4-yl, prenyl, pent-1-enyl, pent-3-enyl, 1,1-dimethylallyl, cyclopentenyl, hex-2-enyl, 1-methyl-1-ethylallyl, cyclohexenyl, heptenyl, cycloheptenyl, octenyl, cyclooctenyl, decenyl, tetradecenyl, hexadecenyl, eicosenyl, tetracosenyl and the like. The term "lower alkenyl" intends an alkenyl group of 2 to 6 carbon atoms, preferably 2 to 4 carbon atoms. The term "cycloalkenyl" intends a cyclic alkenyl group of 3 to 8, preferably 5 or 6, carbon atoms.

The term "Alkenyloxy" refers to an "—Oalkenyl" group, wherein alkenyl is as defined above.

The term "Alkylaryl" refers to an alkyl group that is covalently joined to an aryl group. Preferably, the alkyl is a lower alkyl. Exemplary alkylaryl groups include benzyl, phenethyl, phenopropyl, 1-benzylethyl, phenobutyl, 2-benzylpropyl, etc.

The term "Alkylaryloxy" refers to an "-Oalkylaryl" group, where alkylaryl is as defined above.

The term "Alkynyl" refers to a branched or unbranched hydrocarbon group of 2 to 24 carbon atoms containing at least one carbon-carbon triple bond, optionally substituted at one or more positions. Examples of alkynyl groups include ethynyl, n-propynyl, isopropynyl, propargyl, but-2-ynyl, 3-methylbut-1-ynyl, octynyl, decynyl, etc. The term "lower alkynyl" intends an alkynyl group of 2 to 6, preferably 2 to 4, carbon atoms, and one carbon-carbon triple bond.

The term "Amide" refers to —C(O)NR'R", where R' and R" are independently selected from hydrogen, alkyl, aryl, and alkylaryl.

The term "Amine" refers to an —N(R')R" group, where R' and R" are independently selected from hydrogen, alkyl, aryl, and alkylaryl.

The term "Aryl" refers to an aromatic group that has at least one ring having a conjugated pi electron system and includes carbocyclic, heterocyclic, bridged and/or polycyclic aryl groups, and can be optionally substituted at one or more positions. Typical aryl groups contain 1 to 5 aromatic rings, which may be fused and/or linked. Exemplary aryl groups include phenyl, furanyl, azolyl, thiofuranyl, pyridyl, pyrimidyl, pyrazinyl, triazinyl, biphenyl, indenyl, benzofuranyl, indolyl, naphthyl, quinolinyl, isoquinolinyl, quinazolinyl, pyridopyridinyl, pyrrolopyridinyl, purinyl, tetralinyl and the like. Exemplary substituents on optionally substituted aryl groups include alkyl, alkoxy, alkylcarboxy, alkenyl, alkenyloxy, alkenylcarboxy, aryl, aryloxy, alkylaryl, alkylaryloxy, fused saturated or unsaturated optionally substituted rings, halogen, haloalkyl, heteroalkyl, sulfonyl, etc.

The term "Aryloxy" refers to an "—Oaryl" group, where aryl is as defined above.

The term "Halo" or "halogen" refers to fluoro, chloro, bromo or iodo. "Halide" refers to the anionic form of the halogens.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. These terms refer to the primary structure of the molecule. Thus, the terms includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide.

More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing a phosphate or other polyanionic backbone, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms are used interchangeably herein. These terms refer only to the primary structure of the molecule. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, and hybrids thereof including for example hybrids between DNA and RNA, and also include known types of modifications, for example, labels, alkylation, "caps," substitution of one or more of the nucleotides with an analog, internucleotide modifications such as, for example, those with negatively charged linkages (e.g., phosphorothioates, phosphorodithioates, etc.), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

Terms such as "connected," "attached," and "linked" are used interchangeably herein and encompass direct as well as indirect connection, attachment, linkage or conjugation unless the context clearly dictates otherwise.

Further contemplated by the present invention is functionalized nanostructures using chemoselective ligation. First described in the arena of protein chemistry, the term is used to describe the coupling of two functional groups in an aqueous environment. The coupling partners are mutually and uniquely reactive, thereby eliminating the need for protecting groups on surrounding functional groups. Chemoselective ligation reactions have been designed for modification of cell surfaces, as well as to provide for ligation reactions in peptide synthesis. Chemoselective ligation reactions have also been designed to modify only one cellular component among all others have provided unique insight into cellular processes (Winans et al. Chem. Biol. 1998, 5, R313), the contents of which are hereby incorporated by reference for all purposes. Chemoselective ligation reactions and functional moieties contemplated for the present invention are found in Published Application No. US 20050148032 A1, published Jul. 7, 2005, the contents of which are hereby incorporated by reference in its entirety.

Thus, again as will be appreciated, the substrates involved, the nanofibers involved (e.g., attached to, or deposited upon, the substrates), and any optional functionalization of the nanofibers and/or substrates, and the like can be varied. For example, the length, diameter, conformation and density of the fibers can be varied, as can the composition of the fibers and their surface chemistry.

C) Nanostructure Density

In terms of density, it will be appreciated that by including more nanofibers emanating from a surface, one automatically increases the amount of surface area that is extended from the basic underlying substrate. This, thus, increases the amount of intimate contact area between the surface and any analyte, etc. coming into contact with the nanofiber surfaces. As explained in more detail below, the embodiments herein optionally comprise a density of nanofibers on a surface of from about 0.1 to about 1000 or more nanofibers per micrometer$^2$ of the substrate surface. Again, here too, it will be appreciated that such density depends upon factors such as the diameter of the individual nanofibers, etc. See, below. The nanowire density influences the enhanced surface area, since a greater number of nanofibers will tend to increase the overall amount of area of the surface. Therefore, the density of the nanofibers herein typically has a bearing on the intended use of the enhanced surface area materials because such density is a factor in the overall area of the surface.

For example, a typical flat planar substrate, e.g., a silicon oxide chip or a glass slide, can typically comprise 10,000 possible binding sites for an analyte or 10,000 possible functionalization sites, etc. per square micron (i.e., within a square micron footprint). However, if such a substrate surface were coated with nanofibers, then the available surface area would be much greater. In some embodiments herein each nanofiber on a surface comprises about 1 square micron in surface area (i.e., the sides and tip of each nanofiber present that much surface area). If a comparable square micron of substrate comprised from 10 to about 100 nanofibers per square micron, the available surface area is thus 10 to 100 times greater than a plain flat surface. Therefore, in the current illustration, an enhanced surface area would have 100,000 to 10,000,000 possible binding sites, functionalization sites, etc. per square micron footprint. It will be appreciated that the density of nanofibers on a substrate is influenced by, e.g., the diameter of the nanofibers and any functionalization of such fibers, etc.

Different embodiments of the invention comprise a range of such different densities (i.e., number of nanofibers per unit area of a substrate to which nanofibers are attached). The number of nanofibers per unit area can optionally range from about 1 nanofiber per 10 micron$^2$ up to about 200 or more nanofibers per micron$^2$; from about 1 nanofiber per micron$^2$ up to about 150 or more nanofibers per micron 2; from about 10 nanofibers per micron$^2$ up to about 150 or more nanofibers per micron$^2$; or from about 25 nanofibers per micron$^2$ up to about 75 or more nanofibers per micron. In yet other embodiments, the density can optionally range from about 1 to 3 nanowires per square micron to up to approximately 2,500 or more nanowires per square micron.

In terms of individual fiber dimensions, it will be appreciated that by increasing the thickness or diameter of each individual fiber, one will again, automatically increase the overall area of the fiber and, thus, the overall area of the substrate. The diameter of nanofibers herein can be controlled through, e.g., choice of compositions and growth conditions of the nanofibers, addition of moieties, coatings or the like, etc. Preferred fiber thicknesses are optionally between from about 5 nm up to about 1 micron or more (e.g., 5 microns); from about 10 nm to about 750 nanometers or more; from about 25 nm to about 500 nanometers or more; from about 50 nm to about 250 nanometers or more, or from about 75 nm to about 100 nanometers or more. In some embodiments, the nanofibers comprise a diameter of approximately 40 nm.

In addition to diameter, surface area of nanofibers (and therefore surface area of a substrate to which the nanofibers are attached) also is influenced by length of the nanofibers. Of course, it will also be understood that for some fiber materials, increasing length may yield increasing fragility. Accordingly, preferred fiber lengths will typically be between about 2 microns (e.g., 0.5 microns) up to about 1 mm or more; from about 10 microns to about 500 micrometers or more; from about 25 microns to about 250 microns or more; or from about 50 microns to about 100 microns or more. Some embodiments comprise nanofibers of approximately 50 microns in length. Some embodiments herein comprise nanofibers of approximately 40 nm in diameter and approximately 50 microns in length.

Nanofibers herein can present a variety of aspect ratios. Thus, nanofiber diameter can comprise, e.g., from about 5 nm up to about 1 micron or more (e.g., 5 microns); from about 10 nm to about 750 nanometers or more; from about 25 nm to about 500 nanometers or more; from about 50 nm to about 250 nanometers or more, or from about 75 nm to about 100 nanometers or more, while the lengths of such nanofibers can comprise, e.g., from about 2 microns (e.g., 0.5 microns) up to about 1 mm or more; from about 10 microns to about 500 micrometers or more; from about 25 microns to about 250 microns or more; or from about 50 microns to about 100 microns or more Fibers that are, at least in part, elevated above a surface are often preferred, e.g., where at least a portion of the fibers in the fiber surface are elevated at least 10 nm, or even at least 100 nm above a surface, in order to provide enhanced surface area available for contact with, e.g., an analyte, etc.

The nanofibers optionally form a complex three-dimensional structure. The degree of such complexity depends in part upon, e.g., the length of the nanofibers, the diameter of the nanofibers, the length:diameter aspect ratio of the nanofibers, moieties (if any) attached to the nanofibers, and the growth conditions of the nanofibers, etc. The bending, interlacing, etc. of nanofibers, which help affect the degree of enhanced surface area available, are optionally manipulated through, e.g., control of the number of nanofibers per unit area as well as through the diameter of the nanofibers, the length and the composition of the nanofibers, etc. Thus, it will be appreciated that enhanced surface area of nanofiber substrates herein is optionally controlled through manipulation of these and other parameters.

Also, in some, but not all, embodiments herein, the nanofibers of the invention comprise bent, curved, or even curled forms. As can be appreciated, if a single nanofiber snakes or coils over a surface (but is still just a single fiber per unit area bound to a first surface), the fiber can still provide an enhanced surface area due to its length, etc.

D) Nanofiber Composition

As will be appreciated, the current invention is not limited by the means of synthetic method or composition of the nanofibers herein. For example, while some of the nanofibers used as examples herein are composed of silicon, the use of silicon should not be construed as limiting. The formation of nanofibers is possible through a number of different approaches that are well known to those of skill in the art, all of which are amenable to embodiments of the current invention.

Typical embodiments herein can be used with existing methods of nanostructure fabrication, as will be known by those skilled in the art, as well as methods mentioned or described herein. Typical, but not all, embodiments herein comprise substances that are chosen to be non-harmful (e.g., non-reactive, non-allergenic, etc.) in medical settings. In other words, a variety of methods for making nanofibers and nanofiber containing structures have been described and can be adapted for use in various of the methods, systems and devices of the invention.

The nanofibers can be fabricated of essentially any convenient material (e.g., a semiconducting material, a ferroelectric material, a metal, ceramic, polymers, etc.) and can comprise essentially a single material or can be heterostructures. For example, the nanofibers can comprise a semiconducting material, for example a material comprising a first element selected from group 2 or from group 12 of the periodic table and a second element selected from group 16 (e.g., ZnS, ZnO, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, and like materials); a material comprising a first element selected from group 13 and a second element selected from group 15 (e.g., GaN, GaP, GaAs, GaSb, InN, InP, InAs, InSb, and like materials); a material comprising a group 14 element (Ge, Si, and like materials); a material such as PbS, PbSe, PbTe, AlS, AlP, and AlSb; or an alloy or a mixture thereof.

In some embodiments herein, the nanofibers are optionally comprised of silicon or a silicon oxide. It will be understood by one of skill in the art that the term "silicon oxide" as used herein can be understood to refer to silicon at any level of oxidation. Thus, the term silicon oxide can refer to the chemical structure $SiO_x$, wherein x is between 0 and 2 inclusive. In other embodiments, the nanofibers can comprise, e.g., silicon, glass, quartz, plastic, metal, polymers, TiO, ZnO, ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, PbS, PbSe, PbTe, AlS, AlP, AlSb, Ge, SiGe, SiO, $SiO_2$, silicon carbide, silicon nitride, polyacrylonitrile (PAN), polyetherketone, polyimide, aromatic polymers, or aliphatic polymers.

The nanofibers of this invention can be substantially homogeneous in composition, or in certain embodiments they are heterogeneous, i.e. heterostructures. Non-limiting examples of such heterostructures are disclosed in U.S. Published Application No. 20050054004 A1, published Mar. 10, 2005, the contents of which are hereby incorporated herein by reference in its entirety. Non-limiting examples include graded core/shell semiconductor nanofibers comprising at least a first segment comprising a core comprising a Group II-VI, Group III-V or a Group IV semiconductor, a graded shell overlying the core, wherein the graded shell comprises at least two monolayers, wherein the at least two monolayers each independently comprise a Group II-VI, Group III-V or a Group IV semiconductor.

Other examples of heterostructures include a first segment of a first material and a second segment of a second material joined longitudinally to said first segment; wherein the at least one of the first and second segment is capable of generating emission in response to excitation energy. In one embodiment the first and second segments comprise a nanorod core and said first and second segment cores independently comprises either a semiconductor material selected from the group consisting of Group II-VI, Group III-V and Group IV semiconductors or a metal selected from the group consisting of transition metals, oxides and nitrides thereof. Also included are a third segment connected longitudinally to said first segment core, and said third segment core comprising a semiconductor material selected from the group consisting of Group II-VI, Group III-V and Group IV semiconductors.

One skilled in the art is able to construct nanowires of such compounds having desired band gaps so as to emit a desired radation or radiation at a combination of wavelengths, in response to a stimulation, usually electromagnetic radation, i.e. light. When these nanowires are used in accordance with the present invention there is the ability to monitor a variety of biologically important processes, in situ.

Methods for synthesizing heterostructures are known in the art and is accomplished by providing a core, combining the core with at least one surfactant, heating the mixture, combining the mixture with a CdS/ZnS stock solution, wherein the core comprises a semiconductor material, and graded core/shell nanorods are produced. Preferably the core is rod shaped and comprises CdSe. The mixture is heated to a temperature between 100-360° C. Preferably the mixture is heated to a temperature of 160° C. Preferably the core is combined with only one surfactant. Preferably the surfactant is chosen from the group consisting of TOPO, TBP, HDA, HPA and TDPA. In one embodiment the mixture is kept at a temperature of approximately 160° C. for between 5 minutes and 24 hours after combining the CdS/ZnS stock solution, preferably the mixture is kept at a temperature of 160 C° for 10 minutes after combining the CdS/ZnS stock solution. The graded core/shell nanorods may be photochemically annealed using an Ar+ laser. By "TOPO, TOP, TBP, HDA, HPA and TDPA" it is meant trioctylphosphine oxide, trioctylphosphine, tri-n-butylphosphine, hexadecylamine, hexylphosphonic acid and tetradecylphosphonic acid, respectfully.

Also contemplated as nanostructures for use with the invention herein are hollow nanoparticles such as disclosed in "Formation of Hollow Nanocrystals throught the Kirkendall effect" by Yadong Yin, Robert M. Rioux, Can K. Erdonmez, Steven Hughes, Gabor A. Somorjai, and A. Paul Alivisatos in *Science*, 30 Apr. 2004, the contents of which are hereby incorporated by reference in its entirety for all purposes.

It will be appreciated that in some embodiments, the nanofibers can comprise the same material as one or more substrate surface (i.e., a surface to which the nanofibers are attached or associated), while in other embodiments the nanofibers comprise a different material than the substrate surface. Additionally, the substrate surfaces can optionally comprise any one or more of the same materials or types of materials as do the nanofibers (e.g., such as the materials illustrated herein).

As previously stated, some, but by no means all, embodiments herein comprise silicon nanofibers. Common methods for making silicon nanofibers include vapor liquid solid growth (VLS), laser ablation (laser catalytic growth) and thermal evaporation. See, for example, Morales et al. (1998) "A Laser Ablation Method for the Synthesis of Crystalline Semiconductor Nanowires" Science 279, 208-211 (1998). In one example approach, a hybrid pulsed laser ablation/chemical vapor deposition (PLA-CVD) process for the synthesis of semiconductor nanofibers with longitudinally ordered heterostructures, and variations thereof, can be used. See, Wu et al. (2002) "Block-by-Block Growth of Single-Crystalline Si/SiGe Superlattice Nanowires," Nano Letters Vol. 0, No. 0.

In general, multiple methods of making nanofibers have been described and can be applied in the methods, systems and devices herein. In addition to Morales et al. and Wu et al. (above), see, for example, Lieber et al. (2001) "Carbide Nanomaterials" U.S. Pat. No. 6,190,634 BI; Lieber et al. (2000) "Nanometer Scale Microscopy Probes" U.S. Pat. No. 6,159,742; Lieber et al. (2000) "Method of Producing Metal Oxide Nanorods" U.S. Pat. No. 6,036,774; Lieber et al. (1999) "Metal Oxide Nanorods" U.S. Pat. No. 5,897,945; Lieber et al. (1999) "Preparation of Carbide Nanorods" U.S. Pat. No. 5,997,832; Lieber et al. (1998) "Covalent Carbon Nitride Material Comprising $C_2N$ and Formation Method" U.S. Pat. No. 5,840,435; Thess, et al. (1996) "Crystalline Ropes of Metallic Carbon Nanotubes" Science 273:483-486; Lieber et al. (1993) "Method of Making a Superconducting Fullerene Composition By Reacting a Fullerene with an Alloy Containing Alkali Metal" U.S. Pat. No. 5,196,396; and Lieber et al. (1993) "Machining Oxide Thin Films with an Atomic Force Microscope: Pattern and Object Formation on the Nanometer Scale" U.S. Pat. No. 5,252,835. Recently, one dimensional semiconductor heterostructure nanocrystals, have been described. See, e.g., Bjork et al. (2002) "One-dimensional Steeplechase for Electrons Realized" Nano Letters Vol. 0, No. 0.

It should be noted that some references herein, while not specific to nanofibers, are optionally still applicable to the invention. For example, background issues of construction conditions and the like are applicable between nanofibers and other nanostructures (e.g., nanocrystals, etc.).

In another approach which is optionally used to construct nanofibers of the invention, synthetic procedures to prepare individual nanofibers on surfaces and in bulk are described, for example, by Kong, et al. (1998) "Synthesis of Individual Single-Walled Carbon Nanotubes on Patterned Silicon Wafers," Nature 395:878-881, and Kong, et al. (1998) "Chemical Vapor Deposition of Methane for Single-Walled Carbon Nanotubes," Chem. Phys. Lett. 292:567-574.

In yet another approach, substrates and self assembling monolayer (SAM) forming materials can be used, e.g., along with microcontact printing techniques to make nanofibers, such as those described by Schon, Meng, and Bao, "Self-assembled monolayer organic field-effect transistors," Nature 413:713 (2001); Zhou et al. (1997) "Nanoscale Metal/Self-Assembled Monolayer/Metal Heterostructures," Applied Physics Letters 71:611; and WO 96/29629 (Whitesides, et al., published Jun. 26, 1996).

In some embodiments herein, nanofibers (e.g., nanowires) can be synthesized using a metallic catalyst. A benefit of such embodiments allows use of unique materials suitable for surface modifications to create enhanced properties. A unique property of such nanofibers is that they are capped at one end with a catalyst, typically gold. This catalyst end can optionally be functionalized using, e.g., thiol chemistry without affecting the rest of the wire, thus, making it capable of bonding to an appropriate surface. In such embodiments, the result of such functionalization, etc., is to make a surface with end-linked nanofibers. These resulting "fuzzy" surfaces, therefore, have increased surface areas (i.e., in relation to the surfaces without the nanofibers) and other unique properties. In some such embodiments, the surface of the nanowire and/or the target substrate surface is optionally chemically modified (typically, but not necessarily, without affecting the gold tip) in order to give a wide range of properties useful in many applications.

In other embodiments, to slightly increase or enhance a surface area, the nanofibers are optionally laid "flat" (i.e., substantially parallel to the substrate surface) by chemical or electrostatic interaction on surfaces, instead of end-linking the nanofibers to the substrate. In yet other embodiments herein, techniques involve coating the base surface with functional groups which repel the polarity on the nanofiber so that the fibers do not lay on the surface but are end-linked.

Synthesis of nanostructures, e.g., nanocrystals, of various composition is described in, e.g., Peng et al. (2000) "Shape control of CdSe nanocrystals" Nature 404:59-61; Puntes et al. (2001) "Colloidal nanocrystal shape and size control: The case of cobalt" Science 291:2115-2117; U.S. Pat. No. 6,306, 736 to Alivisatos et al. (Oct. 23, 2001) entitled "Process for forming shaped group III-V semiconductor nanocrystals, and product formed using process"; U.S. Pat. No. 6,225,198 to Alivisatos et al. (May 1, 2001) entitled "Process for forming shaped group II-VI semiconductor nanocrystals, and product formed using process"; U.S. Patent No. U.S. Pat. No. 5,505, 928 to Alivisatos et al. (Apr. 9, 1996) entitled "Preparation of III-V semiconductor nanocrystals"; U.S. Pat. No. 5,751,018 to Alivisatos et al. (May 12, 1998) entitled "Semiconductor nanocrystals covalently bound to solid inorganic surfaces using self-assembled monolayers"; U.S. Pat. No. 6,048,616 to Gallagher et al. (Apr. 11, 2000) entitled "Encapsulated quantum sized doped semiconductor particles and method of manufacturing same"; and U.S. Pat. No. 5,990,479 to Weiss et al. (Nov. 23, 1999) entitled "Organo luminescent semiconductor nanocrystal probes for biological applications and process for making and using such probes."

Additional information on growth of nanofibers, such as nanowires, having various aspect ratios, including nanofibers with controlled diameters, is described in, e.g., Gudiksen et al. (2000) "Diameter-selective synthesis of semiconductor nanowires" J. Am. Chem. Soc. 122:8801-8802; Cui et al. (2001) "Diameter-controlled synthesis of single-crystal silicon nanowires" Appl. Phys. Lett. 78:2214-2216; Gudiksen et al. (2001) "Synthetic control of the diameter and length of single crystal semiconductor nanowires" J. Phys. Chem. B 105:4062-4064; Morales et al. (1998) "A laser ablation method for the synthesis of crystalline semiconductor nanowires" Science 279:208-211; Duan et al. (2000) "General synthesis of compound semiconductor nanowires" Adv. Mater. 12:298-302; Cui et al. (2000) "Doping and electrical transport in silicon nanowires" J. Phys. Chem. B 104:5213-5216; Peng et al. (2000), supra; Puntes et al. (2001), supra; U.S. Pat. No. 6,225,198 to Alivisatos et al., supra; U.S. Pat. No. 6,036,774 to Lieber et al. (Mar. 14, 2000) entitled "Method of producing metal oxide nanorods"; U.S. Pat. No. 5,897,945 to Lieber et al. (Apr. 27, 1999) entitled "Metal oxide nanorods"; U.S. Pat. No. 5,997,832 to Lieber et al. (Dec. 7, 1999) "Preparation of carbide nanorods"; Urbau et al. (2002) "Synthesis of single-crystalline perovskite nanowires composed of barium titanate and strontium titanate" J. Am. Chem. Soc., 124:1186; Yun et al. (2002) "Ferroelectric Properties of Individual Barium Titanate Nanowires Investigated by Scanned Probe Microscopy" Nano Letters 2, 447; and published PCT application nos. WO 02/17362, and WO 02/080280.

Growth of branched nanofibers (e.g., nanotetrapods, tripods, bipods, and branched tetrapods) is described in, e.g., Jun et al. (2001) "Controlled synthesis of multi-armed CdS nanorod architectures using monosurfactant system" J. Am. Chem. Soc. 123:5150-5151; and Manna et al. (2000) "Synthesis of Soluble and Processable Rod-, Arrow-, Teardrop-, and Tetrapod-Shaped CdSe Nanocrystals" J. Am. Chem. Soc. 122:12700-12706, and U.S. Pat. No. 6,855,202Synthesis of nanoparticles is described in, e.g., U.S. Patent No. U.S. Pat. No. 5,690,807 to Clark Jr. et al. (Nov. 25, 1997) entitled "Method for producing semiconductor particles"; U.S. Patent No. U.S. Pat. No. 6,136,156 to El-Shall, et al. (Oct. 24, 2000) entitled "Nanoparticles of silicon oxide alloys"; U.S. Patent No. U.S. Pat. No. 6,413,489 to Ying et al. (Jul. 2, 2002) entitled "Synthesis of nanometer-sized particles by reverse micelle mediated techniques"; and Liu et al. (2001) "Sol-Gel Synthesis of Free-Standing Ferroelectric Lead Zirconate Titanate Nanoparticles" J. Am. Chem. Soc. 123:4344. Synthesis of nanoparticles is also described in the above citations for growth of nanocrystals, and nanofibers such as nanowires, branched nanowires, etc.

Synthesis of core-shell nanofibers, e.g., nanostructure heterostructures, is described in, e.g., Peng et al. (1997) "Epitaxial growth of highly luminescent CdSe/CdS core/shell nanocrystals with photostability and electronic accessibility" J. Am. Chem. Soc. 119:7019-7029; Dabbousi et al. (1997) "(CdSe)ZnS core-shell quantum dots: Synthesis and characterization of a size series of highly luminescent nanocrystallites" J. Phys. Chem. B 101:9463-9475; Manna et al. (2002) "Epitaxial growth and photochemical annealing of graded CdS/ZnS shells on colloidal CdSe nanorods" J. Am. Chem. Soc. 124:7136-7145; and Cao et al. (2000) "Growth and properties of semiconductor core/shell nanocrystals with InAs cores" J. Am. Chem. Soc. 122:9692-9702. Similar approaches can be applied to growth of other core-shell nanostructures. See, for example, U.S. Pat. No. 6,207,229 (Mar. 27, 2001) and U.S. Pat. No. 6,322,901 (Nov. 27, 2001) to Bawendi et al. entitled "Highly luminescent color-selective materials."

Nanostructures may also be fabricated by the method disclosed in Somorjai G., et al. J. Phys. Chem. B 2003, 107, 3340-3343, the contents of which are hereby incorporated by reference in its entirety. Hollow nanoparticles such as disclosed in "Formation of hollow nanocrystals through the nanoscale Kirkendall effect," by Yadong Yin, Robert M. Rioux, Can K. Erdonmez, Steven Hughes, Gabor A. Somorjai, and A. Paul Alivisatos in Science, 30 Apr. 2004, the contents of which are hereby incorporated by reference in its entirety for all purposes are particularly suitable for use in this invention in some embodiments requiring a high surface area and nanoparticles.

Growth of homogeneous populations of nanofibers, including nanofibers heterostructures in which different materials are distributed at different locations along the long axis of the nanofibers is described in, e.g., published PCT application nos. WO 02/17362, and WO 02/080280; Gudiksen et al. (2002) "Growth of nanowire superlattice structures for nanoscale photonics and electronics" Nature 415:617-620; Bjork et al. (2002) "One-dimensional steeplechase for electrons realized" Nano Letters 2:86-90; Wu et al. (2002) "Block-by-block growth of single-crystalline Si/SiGe superlattice nanowires" Nano Letters 2, 83-86; and U.S. patent application 60/370,095 (Apr. 2, 2002) to Empedocles entitled "Nanowire heterostructures for encoding information." Similar approaches can be applied to growth of other heterostructures and applied to the various methods and systems herein.

In some embodiments the nanofibers used to create enhanced surface areas can be comprised of nitride (e.g., AlN, GaN, SiN, BN) or carbide (e.g., SiC, TiC, Tungsten carbide, boron carbide) in order to create nanofibers with high strength and durability. Alternatively, such nitrides/carbides (and other materials as well such as silica, Al2O3 etc.) are used as hard coatings on lower strength (e.g., silicon or ZnO) nanofibers. While the dimensions of silicon nanofibers are excellent for many applications requiring enhanced surface area (e.g., see, throughout and "Structures, Systems and Methods for Joining Articles and Materials and Uses Therefore," filed Apr. 17, 2003, U.S. Ser. No. 60/463,766 and U.S. 10/661,381, filed Sep. 12, 2003 published as published application US 2004-0206448 A1) other applications require nanofibers that are less brittle and which break less easily. Therefore, some embodiments herein take advantage of materials such as nitrides and carbides which have higher bond strengths than, e.g., Si, $SiO_2$ or ZnO. The nitrides and carbides are optionally used as coatings to strengthen the weaker nanofibers or even as nanofibers themselves. The nanofibers may also be coated with any other biologically compatible material (e.g., a silicon nanowire with an ALD coating of TiO such as $TiO_2$) suitable for use with a medical device according to the teachings of the present invention, including any other organic, inorganic or hybrid organic/inorganic material.

Carbides and nitrides can be applied as coatings to low strength fibers by deposition techniques such as sputtering, atomic layer deposition and plasma processes. In some embodiments, to achieve high strength nanocoatings of carbide and nitride coatings, a random grain orientation and/or amorphous phase are grown to avoid crack propagation. Optimum conformal coating of the nanofibers can optionally be achieved if the fibers are growing perpendicular to a substrate surface. The hard coating for fibers in such orientation also acts to enhance the adhesion of the fibers to the substrate. For fibers that are randomly oriented, the coating is preferential to the upper layer of fibers.

Low temperature processes for creation of silicon nanofibers are achieved by the decomposition of silane at about 400° C. in the presence of a gold catalyst. However, as previously stated, silicon nanofibers are too brittle for some applications to form a durable nanofiber matrix (i.e., an enhanced surface area). Thus, formation and use of, e.g., SiN is optionally utilized in some embodiments herein. In those embodiments, $NH_3$, which has decomposition at about 300° C., is used to combine with silane to form SiN nanofibers (also by using a gold catalyst). Other catalytic surfaces to form such nanofibers can include, e.g., Ti, Fe, etc.

Forming carbide and nitride nanofibers directly from a melt can sometimes be challenging since the temperature of the liquid phase is typically greater than 1000° C. However, a nanofiber can be grown by combining the metal component with the vapor phase. For example, GaN and SiC nanofibers have been grown (see, e.g., Peidong, Lieber, supra) by exposing Ga melt to $NH_3$ (for GaN) and graphite with silane (SiC). Similar concepts are optionally used to form other types of carbide and nitride nanofibers by combing metal-organic vapor species, e.g., tungsten carbolic [W(CO)6] on a carbon surface to form tungsten carbide (WC), or titanium dimethoxy dineodecanoate on a carbon surface to form TiC. It will be appreciated that in such embodiments, the temperature, pressure, power of the sputtering and the CVD process are all optionally varied depending upon, e.g., the specific parameters desired in the end nanofibers. Additionally, several types of metal organic precursors and catalytic surfaces used to form the nanofibers, as well as, the core materials for the nanofibers (e.g., Si, ZnO, etc.) and the substrates containing the nanofibers, are all also variable from one embodiment to another depending upon, e.g., the specific enhanced nanofiber surface area to be constructed.

The present invention can be used with structures that may fall outside of the size range of typical nanostructures. For example, Haraguchi et al. (U.S. Pat. No. 5,332,910) describes nanowhiskers which are optionally used herein. Semi-conductor whiskers are also described by Haraguchi et al. (1994) "Polarization Dependence of Light Emitted from GaAs p-n junctions in quantum wire crystals" J. Appl. Phys. 75(8): 4220-4225; Hiruma et al. (1993) "GaAs Free Standing Quantum Sized Wires," J. Appl. Phys. 74(5):3162-3171; Haraguchi et al. (1996) "Self Organized Fabrication of Planar GaAs Nanowhisker Arrays"; and Yazawa (1993) "Semiconductor Nanowhiskers" Adv. Mater. 5(78):577-579. Such nanowhiskers are optionally nanofibers of the invention. While the above references (and other references herein) are optionally used for construction and determination of parameters of nanofibers of the invention, those of skill in the art will be familiar with other methods of nanofiber construction/design, etc. which can also be amenable to the methods and devices herein.

Some embodiments herein comprise repetitive cycling of nanowire synthesis and gold fill deposition to make "nanotrees" as well as the co-evaporation of material that will not form a silicon eutectic, thus, disrupting nucleation and causing smaller wire formation Such methods are utilized in the creation of ultra-high capacity surface based structures through nanofiber growth technology for, e.g., adhesion promotion between surfaces, non-fouling surfaces, etc.). Use of single-step metal film type process in creation of nanofibers limits the ability to control the starting metal film thickness, surface roughness, etc., and, thus, the ability of control nucleation from the surface. The present methods address these issues In some embodiments of nanofiber enhanced surfaces it can be desirable to produce multibranched nanofibers. Such multibranched nanofibers could allow an even greater increase in surface area than would occur with non-branched nanofiber surfaces. To produce multibranched nanofibers gold film is optionally deposited onto a nanofiber surface (i.e., one that has already grown nanofibers). When placed in a furnace, fibers perpendicular to the original growth direction can result, thus, generating branches on the original nanofibers. Colloidal metal particles can optionally be used instead of gold film to give greater control of the nucleation and branch formation. The cycle of branching optionally could be repeated multiple times, e.g., with different film thicknesses, different colloid sizes, or different synthesis times, to generate additional branches having varied dimensions. Eventually, the branches between adjacent nanofibers could optionally touch and generate an interconnected network. Sintering is optionally used to improve the binding of the fine branches.

In yet other embodiments, it is desirable to form finer nanofibers (e.g., nanowires). To accomplish this, some embodiments herein optionally use a non-alloy forming material during gold or other alloy forming metal evaporation. Such material, when introduced in a small percentage can optionally disrupt the metal film to allow it to form smaller droplets during wire growth and, thus, correspondingly finer wires.

Such approaches can allow improved control of nanofiber formation and allow generation of finer and more numerous nanofibers from a slightly thicker initial metal film layer. In applications such as nanoarrays, etc., the improved control can optionally improve the signal ratio from the nanofibers to the planar surface or just add a greater degree of control. Materials contemplated for use in finer nanofiber construction include, e.g., Ti, $Al_2O_3$ and $SiO_2$.

In yet other embodiments, post processing steps such as vapor deposition of glass can allow for greater anchoring or mechanical adhesion and interconnection between nanofibers, thus, improving mechanical robustness in applications requiring additional strength as well as increasing the overall surface to volume of the nanostructure surface.

E) Interaction of Biomaterials and Nanofiber Enhanced Surface Area Substrates

In typical embodiments, the nanofiber enhanced surface area substrates of the invention are used in various medical product applications. For example, coatings on medical products for drug release, lubricity, cell adhesion, low bio-adsorption, electrical contact, etc. See above. For example, the application of surface texture (e.g., as with the present invention) to the surfaces of polymer implants has been shown to result in significant increases in cellular attachment. See, e.g., Zhang et al. "Nanostructured Hydroxyapatite Coatings for Improved Adhesion and Corrosion Resistance for Medical Implants" Symposium V: Nanophase and Nanocomposite Materials IV, Kormareni et al. (eds.) 2001, MRS Proceedings, vol. 703. Other medical applications of the current embodiments include, e.g., slow-release drug delivery. For example, drugs can be incorporated into various pharmaceutically acceptable carriers which allow slow release over time in physiological environments (e.g., within a patient). Drugs, etc. incorporated into such carriers (e.g., polymer layers, etc.) are shielded, at least partially, from direct exposure to body fluids due to incorporation into the carrier layer (e.g., present interstitially between the nanofibers). Drugs, etc. at the interface between the body fluids and the carrier layer (at the top of the nanofiber layer) diffuse out fairly quickly, while drugs deeper within the carrier layer diffuse out slowly (e.g., once body fluid diffuses into the carrier layer and then diffuses back out with the drug). Such carriers are well known to those of skill in the art and can be deposited or wicked onto the surface of a nanofiber substrate (i.e., amongst the nanofibers).

Fibrinogen and fibrin are importain in blood clotting, fibrinolysis, cellular and matrix interactions, inflammation, wound healing, and neoplasia. These events are regulated to a large extent by fibrin formation and by complementary interactions between specific binding sites on fibrin(ogen) and extrinsic molecules including proenzymes, clotting factors, enzyme inhibitors, and cell receptors. Fibrinogen is comprised of two sets of three polypeptide chains termed Aα, Bβ, and γ, that are joined by disulfide bridging within the N-terminal E domain. The molecules are elongated 45-nm structures consisting of two outer D domains, each connected to a central E domain by a coiled-coil segment. These domains contain constitutive binding sites that participate in fibrinogen conversion to fibrin, fibrin assembly, crosslinking, and platelet interactions (e.g., thrombin substrate, Da, Db, γXL, D:D, αC, γA chain platelet receptor) as well as sites that are available after fibrinopeptide cleavage (e.g., E domain low affinity non-substrate thrombin binding site); or that become exposed as a consequence of the polymerization process (e.g., tPA-dependent plasminogen activation). A constitutive plasma factor XIII binding site and a high affinity non-substrate thrombin binding site are located on variant γ' chains that comprise a minor proportion of the γchain population. Initiation of fibrin assembly by thrombin-mediated cleavage of fibrinopeptide A from Aα chains exposes two $E_A$ polymerization sites, and subsequent fibrinopeptide B cleavage exposes two $E_B$ polymerization sites that can also interact with platelets, fibroblasts, and endothelial cells. Fibrin generation leads to end-to-middle intermolecular Da to $E_A$ associations, resulting in linear double-stranded fibrils and equilaterally branched trimolecular fibril junctions. Side-to-side fibril convergence results in bilateral network branches and multistranded thick fiber cables. Concomitantly, factor XIII or thrombin-activated factor XIIIa introduce intermolecular covalent ε-(γglutamyl)lysine bonds into these polymers, first creating γdimers between properly aligned C-terminal γXL sites, which are positioned transversely between the two strands of each fibrin fibril. Later, crosslinks form mainly between complementary sites on γchains (forming γ-polymers), and even more slowly among γdimers to create higher order crosslinked γtrimers and tetramers, to complete the mature network structure, see for example Mosesson et al, The Structure and Biological Features of Fibrinogen ad Fibrin, *Annals of the New York Academy of Sciences* 936:11-30 (2001) the contents of which are incorporated herein by reference in its entirety. In a preferred embodiment, nanowires are coated with a first coating of fibrinogen, and further coated with a second coating comprising a biocompatible polymer on the fibrinogen. Preferably the second coating encapsulates the fibrinogen.

Biofilm formation and infection on indwelling catheters, orthopedic implants, pacemakers and other medical devices represents a persistent patient health danger. Therefore, some embodiments herein comprise novel surfaces which minimize bacterial colonization, as well as the colonization of viruses, viral spores, etc., due to their advantageous morphology. In contrast, yet other embodiments herein utilize the unique surface morphology of nanofiber enhanced surface area substrates to foster cell growth under desired conditions or in desired locations. The high surface area/non-tortuous aspect of the current invention allows greater attachment area and accessibility (in certain embodiments) for nutrients/fluids, etc. and initial attachment benefits over porous surfaces where growth, etc. is limited by space (both in terms of surface area and space within the pores for the cells to grow out).

The substrates of the invention, because of their high surface areas and ready accessibility (e.g., non-tortuous paths), are extremely useful as bioscaffolds, e.g., in cell culture, implantation, and controlled drug or chemical release applications. In particular, the high surface area of the materials of the invention provide very large areas for attachment of desirable biological cells in, e.g., cell culture or for attachment to implants. Further, because nutrients can readily access these cells, the invention provides a better scaffold or matrix for these applications. This latter issue is a particular concern for implanted materials, which typically employ porous or roughened surfaces in order to provide tissue attachment. In particular, such small, inaccessible pores, while providing for initial attachment, do not readily permit continued maintenance of the attached cells, which subsequently deteriorate and die, reducing the effectiveness of the attachment. Another advantage of the materials of the invention is that they are inherently non-biofouling, e.g., they are resistant to the formation of biofilms from, e.g., bacterial species that typically cause infection for implants, etc.

Without being bound to a particular theory or method of action, the unique morphology of a nanofiber surface can reduce the colonization rate of bacterial species such as, e.g., *Staphylococcus epidermidis* (hereinafter *S. epidermidis*), as well as viruses, viral spores, etc., by about ten fold. For example, embodiments such as those comprising silicon nanowires grown from the surface of a planar silicon oxide substrate by chemical vapor deposition process, and which comprise diameters of approximately 60 nanometers and lengths of about 50-100 microns show reduced bacterial colonization. See, below. It will be appreciated that while specific bacterial species are illustrated in examples herein, that the utility of the embodiments, does not necessarily rest upon use against such species. In other words, other bacterial species are also optionally inhibited in colonization of the nanofiber surfaces herein. Additionally, while examples herein utilize silicon oxide nanowires on similar substrates, it will be appreciated other embodiments are optionally equally utilized (e.g., other configurations of nanofibers; nanofibers on non-silicon substrates such as plastic, etc; patterns of nanofibers on substrates, etc.).

It will be noticed that substrates herein that are covered with high densities of nanofibers (e.g., silicon nanowires) resist bacterial colonization and mammalian cell growth. For example, approximately 10× less (or even less) bacterial growth occurs on a nanowire covered substrate as compared to an identical planar surface. In various embodiments herein, the physical and chemical properties of the nanofiber enhanced surface area substrates are varied in order to optimize and characterize their resistance to bacterial colonization.

In contrast to prevention of bacterial colonization, other embodiments herein comprise substrates that induce the attachment of mammalian cells to the nanofiber surface by functionalization with extra-cellular binding proteins, etc. or other moieties, thus, achieving a novel surface with highly efficient tissue integration properties.

In some embodiments herein where NFS substrates are to be used in settings requiring, e.g., sterility, etc., the nanofibers are optionally coated with, or composed of, titanium dioxide. Such titanium dioxide confers self-sterilizing or oxidative properties to such nanofibers. Nanofibers which comprise titanium dioxide, thus, allow rapid sterilization and oxidation compared to conventional planar $TiO_2$ surfaces while maintaining rapid diffusion to the surface.

In embodiments herein which involve nanowires comprising titanium oxides (e.g., coated nanowires, etc.), such can optionally be synthesized by different methods. For example, in some embodiments herein the nanowires can be designed and implemented through an approach which involves analytical monitoring of $(SiO_4)_x(TiO_4)_y$ nanowires by coating and a molecular precursor approach. The layer thickness and porosity are optionally controlled through concentration of reagent, dip speed, and or choice of precursor for dip coating such as tetraethoxytitanate or tetrabutoxytitanate, gelation in air, air drying and calcinations. Molecular precursors such as $M[(OSi(OtBu)3)4]$, where M=Ti, Zr (or other metals), or other metal oxides, can be decomposed to release 12 equivalents of isobutylene and 6 equivalents of water to form mesoporous materials or nanowires. These precursors can also be used in conjunction with CVD or detergents in nanocrystal syntheses (wet chemistry) to produce dimetallic nanocrystals of desired size distribution. Material can be made via wet chemistry standard inorganic chemistry techniques and oxidative properties determined by simple kinetics monitoring of epoxidation reactions (GC or GCMS) using alkene substrates. Porosity can be monitored by standard BET porosity analysis. Copolymer polyether templates can also be used to control porosity as part of the wet chemistry process.

Titanium oxide materials are well known oxidation catalysts. One of the keys to titanium oxide materials is control of porosity and homogeneity of particle size or shape. Increased surface area typically affords better catalytic turnover rates for the material in oxidation processes. This has been difficult as the kinetics of oxide formation (material morphology) can be difficult to control in solution.

As described, recent interest in $TiO_2$ for oxidative catalytic surfaces (self-cleaning surfaces) shows promise for marketing "green chemistry" cleaning materials. However, the self-cleaning efficiency of the material is dependent upon, e.g., the surface area and porosity. Nanowires have a much higher surface areas than bulk materials (e.g., ones with a nanofiber enhanced surface) that are currently used for self-cleaning materials. Thus, the combination of silicon nanowire technology coated with $TiO_2$ or $TiO_2$ nanowires or molecular precursors to form wires can optionally provide access to previously unknown materials that are useful in self-cleaning, sterilizing, orthopedic/dental implants and/or non-biofouling surfaces.

In some embodiments, such sterilizing activity arises in conjunction with exposure to UV light or other similar excitation. Such factors are optionally important in applications such as, e.g., sterile surfaces in medical settings or food processing settings. The increased surface area due to the NFS of the invention (e.g., increasing area 100-1000 times or the like), therefore, could vastly increase the disinfection rate/ability of such surfaces.

i) Current Means of Preventing Bacterial Contamination of Medical Devices

A variety of methods have been used to combat surface colonization of biomedical implants by bacteria and other microorganisms as well as the resulting biofilm formed. Previous methods have included varying the fundamental biomaterial used in the devices, applying hydrophilic, hydrophobic or bioactive coatings or creating porous or gel surfaces on the devices that contain bioactive agents. The task of generating universal biomaterial surfaces is complicated by species' specificity to particular materials. For example S. epidermidis has been reported to bind more readily to hydrophobic than to hydrophilic surfaces. Staphylococcus aureus (hereinafter S. aureus) has a greater affinity for metals than for polymers, while S. epidermidis forms a film more rapidly on polymers than metals.

Antimicrobial agents, such as antibiotics and polyclonal antibodies integrated into porous biomaterials have been shown to actively prevent microbial adhesion at the implant site. However, the effectiveness of such local-release therapies is often compromised by the increasing resistance of bacteria to antibiotic therapy and the specificity associated with antibodies. Recent in vitro studies have also explored the use of biomaterials that release small molecules such as nitrous oxide in order to non-specifically eliminate bacteria at an implant surface. Nitrous oxide release must, however, be localized to limit toxicity.

ii) Prevention of Biofilm Formation by Nanofiber Enhanced Area Surfaces

Results of the inventors' research and experimentation have shown that silicon nanowire surfaces aggressively resist colonization by the bacteria S. epidermidis as well as the growth of three cell lines: CHO, MDCK and NIH 3T3 cell lines. This was found to be the case when the bacteria or cells were cultured in contact with a native hydrophilic nanowire surface or with a fluorinated hydrophobic nanowire surface. Since control surfaces without the nanowire surface morphology, including silicon oxide flat control surfaces and polystyrene flat control surfaces$_1$ supported profuse growth of S. epidermidis and the three cell lines, it is inferred that the nanowire morphology renders the surface cytophobic. Of course, again, it will be realized that the utility of the current invention is not limited by specific theories or modes of action. However, surface morphology is thought to be basis for the antimicrobial activity. The nanofibers on such substrates are spaced tightly enough to prohibit the bacteria from physically penetrating to the solid surface below. The amount of presentable surface area available for attachment is typically less then 1.0% of the underlying flat surface. In typical embodiments, the nanofibers are approximately 40 nm in diameter and rise to a height about 20 μm above the solid surface. Thus, unlike a typical membrane surface that would be found on a medical device, the nanowire surfaces herein are discontinuous and spiked and have no regular structure to aid in cell attachment. In fact, the current surfaces are almost the exact opposite of a conventional membrane; rather than a solid surface with holes, they are open spiked surfaces. It is thought that this unique morphology discourages normal biofilm attachment irrespective of the hydrophobic or hydrophilic nature of the nanofibers involved.

As detailed throughout, the nanofiber growth process can be conducted on a wide variety of substrates that can have planar or complex geometries. Thus, various substrates of the invention can be completely covered, patterned or have nanofibers in specific locations. For example, one arrangement for capturing nanofibers involves forming surfaces that comprise regions that selectively attract nanofibers such as hydrophobic and/or hydrophilic regions. For example, —NH2 can be presented in a particular pattern at a surface and that pattern will attract nanofibers having surface functionality attractive to amines. Surfaces can be patterned using known techniques such as electron-beam patterning, soft-lithography, or the like. See also, International Patent Publication No. WO 96/29629, published Jul. 26, 1996, and U.S. Pat. No. 5,512,131, issued Apr. 30, 1996. Patterned surfaces can in certain instances enhance the interaction of a device with the body into which it is inserted. For instance, different rows or patches or stripes of hydrophobic and/or hydrophilic regions of nanofibers may be useful to enhance cell integration in certain applications such as orthopedic implants, tissue engineering and the like. However, for ease of focus herein, silicon nanofibers on silicon oxide or metallic substrates are discussed in most detail. Again, however, nanofibers from a wide variety of materials are also contemplated as is growing such on plastic, metal and ceramic substrates. The versatility of the nanofiber production process lends itself to the eventual scale-up and commercialization of a wide variety of products with nanofiber surfaces for the biomedical field.

It is thought that, although absolute surface area is increased on substrates growing nanofibers, the low solid surface volume, lack of continuity and nanoscale aspect of the fibers discourages cellular attachment. The nanowire surfaces used in these illustrations herein was produced for an electronics application and was not optimized for this use, yet, as will be noted, such surfaces still reduced biofilm accumulation. The silicon wires utilized were ~40 nm in diameter and 50 to 100 um in length and were grown on a four inch silicon substrate. The nanowire preparation method is described below. In the current example, the nanowire pieces used in this experiment were about 0.25 $cm^2$. Immediately before introduction into the culture media they were soaked in 100% ethanol and blown dry with a stream of nitrogen. Silicon wafer controls (i.e., without nanowires) were also soaked in ethanol and blown dry. S. epidermidis was grown in LB broth for 6 hours at 37° C. with gentle shaking in 35 mm Petri dishes. Wafer sections were then placed in the culture and left for 24 hours at 37° C. in the original media. The wafer slices were removed after 24 hours incubation, washed briefly in fresh media, rapidly immersed in water and then heat fixed for 30 seconds prior to staining in a 0.2% crystal violet solution. The wafer segments were rinsed thoroughly in water. Any microbes attached to the wafers were visualized by conventional brightfield microscopy. Images were captured with a digital camera. The results showed approximately a ten fold decrease in bacteria on the nanowire substrate as compared to the silicon wafer control. Quantitation was performed on the microscope by focusing through the nanowires since the thickness of the nanowire layer was greater than the depth of field of the microscope.

To illustrate the nanofiber surfaces' repulsion of mammalian cells, CHO cells were maintained in culture in complete media (Hams F12 media supplemented with 10% fetal bovine serum) at 37° C. in a 5% $CO_2$ atmosphere. Wafer segments were placed in 35 mm cell culture treated Petri dishes. CHO cells were seeded into the dishes at a density of $10^6$ cell/ml in complete media after trypsinization from confluent culture. The cells were allowed to adhere overnight and were then observed microscopically every 24 hours. The surface of the 35 mm Petri dish was confluent at 48 hours when the first observation was made. No cell growth was observed directly on the nanowire surface. Where the nanowires had been removed by scratching the surface with a knife the cells adhered and grew. Silicon wafer controls became confluent with cells. In these experiments complete retardation of mammalian cellular growth and approximately a 10× reduction in bacterial growth was observed. The control surfaces were chemically identical to the nanowires so it is thought that reduction in cell and bacterial growth is due to the unique surface morphology of the nanofiber enhanced surface area substrates.

S. epidermidis was used in the illustrations herein because it is a representative bacteria involved in infections of medical devices. Additionally, S. epidermidis has been widely used in the evaluation of biomaterials and has been identified as a dominant species in biomaterial centered infections. Other bacteria implicated in biomaterial related infections such as S. aureus, Pseudomonas aeruginosa and B-hemolytic streptococci are also contemplated as being prohibited through use of current embodiments. In addition to CHO cells illustrated herein, other common tissue culture lines such as, e.g., MDCK, L-929 and HL60 cells are also contemplated as being prohibited through use of current embodiments. Such cell lines represent a wide diversity of cell types. The CHO and MDCK cells are representative of epithelial cells, L-929 cells participate in the formation of connective tissue and the HL60 line represents immune surveillance cells. Thus, the nanofiber enhanced surface areas herein are contemplated against these cell types and other common in vivo cell types. The nanofibers used in the in vitro illustration herein were made of silicon, and, as detailed throughout, several methods have been reported in the literature for the synthesis of silicon nanowires. For example, laser ablating metal-containing silicon targets, high temperature vaporizing of $Si/SiO_2$ mixture, and vapor-liquid-solid (VLS) growth using gold as the catalyst. See, above. While any method of construction is optionally used, the approach to nanowire synthesis is typically VLS growth since this method has been widely used for semiconductor nanowire growth. Description of such method is provided elsewhere herein.

As mentioned previously, it is thought that the primary means of biofilm prevention by nanofiber surfaces herein is due to the unique morphology of the substrate, however, it is also possible that such substrates comprise inherent cytophobicity activity.

The effect of surface hydrophilicity or hydrophobicity on growth is also optionally modified on the nanofiber substrates herein to specifically tailor biofilm prevention in different situations. Such functionalization goes along with variability in wire length, diameter and density on the substrate. The silicon oxide surface layer of the typical nanofiber substrates is quite hydrophilic in its native state. Water readily wets the surface and spreads out evenly. This is partially due to the wicking properties of the surface. Functionalization of the surface is facilitated by the layer of native oxide that forms on the surface of the wires. This layer of $SiO_2$ can be modified using standard silane chemistry to present functional groups on the outside of the wire. For example the surface can be treated with gaseous hexamethyldisilane (HMDS) to make it extremely hydrophobic. See, above. In addition, it is possible to use multi-component nanofiber surfaces to tailor a medical device for a particular application. For example, a hydrophobic (or hydrophilic) nanofiber surface which resists cellular attachment (and thus biofilm formation) as described above can also be specifically tailored to allow one or more specific types of cells such as endothelial cells, osteoblasts, etc. to grow on some (or all) portions of the surface (e.g., where cellular integration and proliferation is needed), e.g., by modifying the hydrophobic (or hydrophilic) nanofiber surface with functional groups (e.g., fibronectin, collagen, RGD containing peptides, extracellular matrix proteins, chemoattracts, and other cell binding motifs)—which promote cellular attachment and integration. The hydrophobic layer may diminish over time as the desired cells integrate. Thus, medical devices such as catheters, implants and the like can be engineered to resist biofilm formation over portions of or their entire surface by rendering the nanofiber surface hydrophobic as described above and in co-pending U.S. Ser. No. 10/833, 944, filed Apr. 27, 2004, the entire contents of which are incorporated by reference herein, and then the surface coverage of one or more functional groups on the hydrophobic surface can be precisely controlled to encourage cellular attachment in specific areas where tissue integration is most desirable (e.g., where grafting or bonding is to occur). Examples of multicomponent films are demonstrated and described, for example, in T. M. Heme et al., *Characterization of DNA Probes Immobilized on Gold Surfaces*, J. Am. Chem. Soc. 1997, 119, 8916-8920 (e.g., FIG. 4), the entire contents of which are incorporated by reference herein."

iii) Attachment of Extra-Cellular Proteins onto Nanofiber Surfaces

As shown herein, nanofiber surfaces do not readily support the growth of mammalian cells or bacteria. Yet, in other instances, the growth of mammalian cell lines on surfaces is advantageous. Thus, embodiments of the current invention, by attaching extra-cellular proteins or other moieties to nanofibers encourages such cell growth. The deposition of the proteins on the nanofibers can be through simple nonspecific adsorption. Other embodiments contemplate covalent attachment of cells/proteins to a nanofiber surface. Proteins with known extra-cellular binding functions such as Collagen, Fibronectin, Vitronectin and Laminin are contemplated in use. In embodiments where grafting and/or bonding of nanofiber substrates and, e.g., biological material such as bone or medical devices such as metal bone pins, etc. is to occur, different embodiments can have different patterns of nanofibers upon the substrate. Thus, for example, nanofibers can optionally only exist on an area of a medical implant where grafting or bonding is to occur. Further, a medical device may be covered by two or more different nanostructured surfaces to impart different properties to different portions of the device as described above. For example, one portion of a device can include nanofibers (e.g., hydrophilic wires) which promote adhesion to tissue surfaces (such as where grafting or bonding is to occur), e.g., through increased interactivity with endothelial cells, osteoblasts, etc., while another portion of the device may be coated with nanofibers that are tailored (e.g., through hydrophobic functionalization) to resist biofouling. Again, standard protein attachment methods can be used to make the covalent linkage to the nanofibers.

Additionally various sol-gel coatings can be deposited upon nanofiber surfaces herein to encourage bio-compatibility and/or bio-integration applications. Previous work on devices concerned with bone integration has used porous materials on titanium implants to encourage bone growth. In some embodiments herein, the current invention utilizes addition of similar materials in conjunction with the nanofiber surfaces herein. For example, hydroxyapatite, a common calcium based mineral, can optionally be deposited on nanofiber surfaces to facilitate bone integration into/with the nanofiber surface. Common sol-gel techniques can optionally be used to produce the hydroxyapatite deposition. Such hydroxyapatite coated nanofiber surfaces optionally could have the benefit of both promoting bone integration and displaying anti-biofouling properties, thus, resulting in a greater likelihood that proper bone growth/healing will occur.

In an alternative embodiment, the nanowires, by virtue of being crystalline in nature, can induce or hasten the crystallization of hydroxyapatite directly in the vicinity of the nanowires. Such results are not surprising in light of the fact that bioactive glass has been utilized for many years as a component of orthopedic materials and the osseointegration has been shown to be superior. With the current invention, high surface area bioactive glass can essentially be grown on the surface of an orthopedic implant, creating a platform on the implant for both control of surface topography as well as altering the biochemical nature of the surface through chemical attachment, adsorption, and other techniques detailed in this invention.

Those of skill in the art will readily appreciate that the current invention also includes use of deposition of ceramic-type materials and the like through sol-gel techniques to produce a wide range of, e.g., compatibility applications (i.e., in addition to those involving hydroxyapatite and bone growth).

F) Kits/Systems

In some embodiments, the invention provides kits for practice of the methods described herein and which optionally comprise the substrates of the invention. In various embodiments, such kits comprise one or more nanofiber enhanced surface area substrate, e.g., one or more catheter, heat exchanger, superhydrophobic surface or, one or more other device comprising a nanofiber enhanced surface area substrate, etc.

The kit can also comprise any necessary reagents, devices, apparatus, and materials additionally used to fabricate and/or use a nanofiber enhanced surface area substrate, or any device comprising such.

In addition, the kits can optionally include instructional materials containing directions (i.e., protocols) for the synthesis of a nanofiber enhanced surface area substrate and/or for adding moieties to such nanofibers and/or use of such nanofiber structures. Preferred instructional materials give protocols for utilizing the kit contents.

In certain embodiments, the instructional materials teach the use of the nanofiber substrates of the invention in the construction of one or more devices (such as, e.g., medical devices, etc.). The instructional materials optionally include written instructions (e.g., on paper, on electronic media such as a computer readable diskette, C D or DVD, or access to an internet website giving such instructions) for construction and/or utilization of the nanofiber enhanced surfaces of the invention.

The following non-limiting Example presents data from a study conducted at Boston University that illustrates how the use of nanofiber (e.g., nanowire) surfaces as compared to control (reference) surfaces (e.g., quartz) for bone biotemplating applications helps in faster cell differentiation which can be expected to result in faster bone in-growth.

Example I i) Osteoblast Culture

Human fetal osteoblasts, designated hFOB 1.19 (American Type Culture Collection (ATCC), Manassas, Va.), were used for cell adhesion studies. This cell line was obtained from a spontaneous miscarriage and transfected with a temperature-sensitive mutant gene of SV40 large T antigen. The cells were programmed to proliferate at 34° C. and differentiate only when the temperature is raised to 39° C. Cells with passage 10 were used in all experiments. The medium used for growing osteoblasts consisted of 1:1 ratio of DMEM:F12 (Invitrogen Corp.) with 10% fetal bovine serum (Sigma-Aldrich) and 0.3 mg/mL of G418 sulfate powder (ATCC). The medium was changed every 2-3 days, and the subculture was done at a ratio of 1:4.

ii) Osteoblast Seeding

Different nanowire surfaces along with control (reference) surfaces (e.g., quartz) were placed in wells of 12-well plates and were placed under ultraviolet lights in a biological hood for 24 hours. They were then soaked in 70% ethanol for 30 minutes for sterilization with final rinsing with PBS and cell culture media. Osteoblasts were seeded at a density of about 100,000 cells/well.

iii) Osteoblast Adhesion and Proliferation

Osteoblast adhesion and proliferation was investigated 1 and 4 days respectively after seeding them on the nanowire and quartz (reference) surfaces. Cell adhesion and proliferation was characterized by trypsinizing the adhered cells on the various surfaces and counting them using a hemacytometer.

Figure 7:
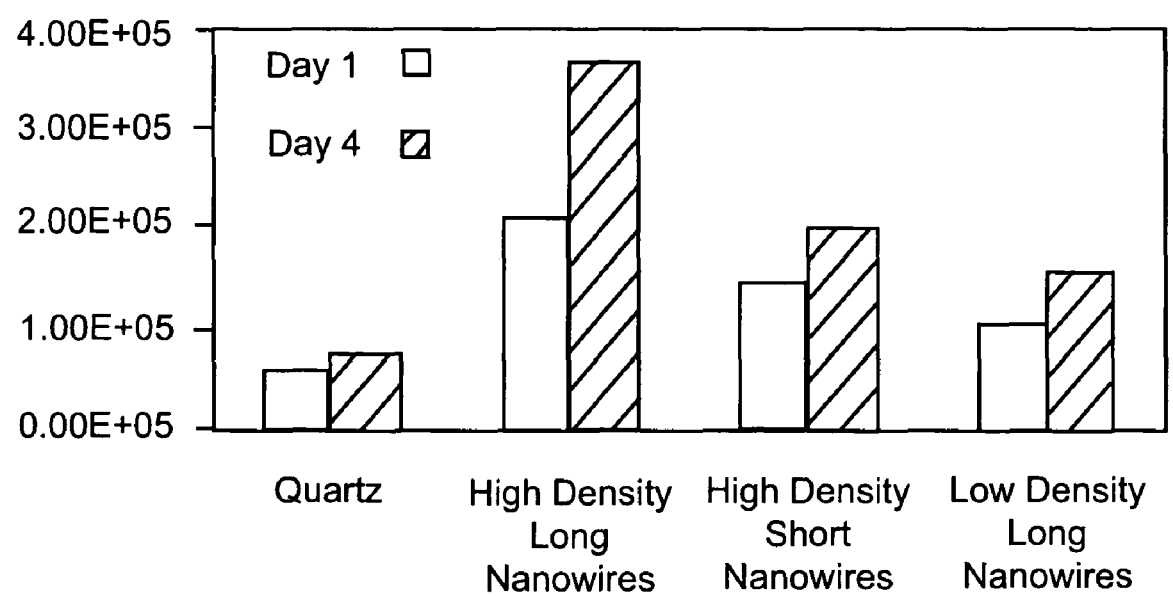
FIG. 7 illustrates osteoblast adhesion and proliferation on various nanowire surfaces and on a control (reference) quartz surface.

FIG. 7 shows the cell count on various surfaces obtained by a hemacytometer for cell adhesion after 1 day and proliferation after 4 days of seeding. To create the nanowire surfaces, commercially available gold colloids were deposited on the substrate surfaces and the substrates were placed in a CVD furnace and silane gas was flowed in at 480° C. for 10 minutes (short wires) or 30 minutes (long wires). This process produced a dense mat of silicon nanowires (with native oxide shells) at locations where the gold catalysis material was deposited yielding nanowires with dimensions of about 40 nm in diameter and between approximately 1 to 30 μm in length. The high density long nanowire surfaces shown in FIG. 7 comprised nanowires grown for 30 minutes and having a length between about 20 to 30 microns and a density of about 25 wires/micron$^2$; the high density short nanowire surfaces shown in FIG. 7 comprised nanowires grown for 10 minutes and having a length between about 7 to 12 microns and a density of about 25 wires/micron$^2$; the low density long nanowire surfaces shown in FIG. 7 comprised nanowires grown for 30 minutes having a length between about 20 to 30 microns and a density of about 5 to 10 wires/micron$^2$. This data demonstrates that nanowire surfaces supported the highest osteoblast adhesion compared to quartz surfaces. However, surfaces with high density long nanowires showed highest adhesion and proliferation followed by high density short nanowires and low density long nanowires. Without being bound to any particular theory, it is believed that this is because high density long nanowires provide high surface area at a nanolevel which promotes osteoblast adhesion and eventually proliferation.

Figures 8A, 8B:
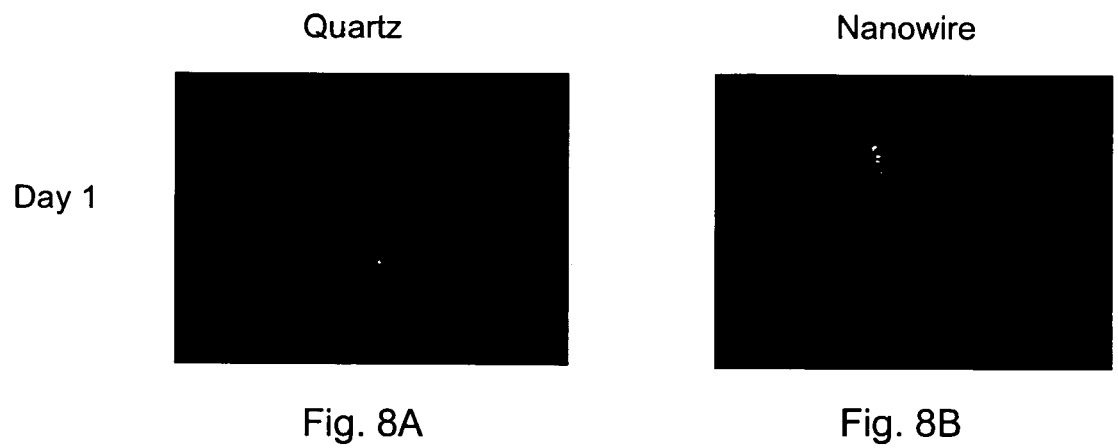
FIGS. 8A-F illustrate fluorescence microscope images of adhered and proliferated cells on various nanowire surfaces after 1 day (FIG. 8B) and 4 days (FIGS. 8D and F) and on quartz surfaces after 1 day (FIG. 8A) and 4 days (FIGS. 8C and E)
Figures 8C, 8D:
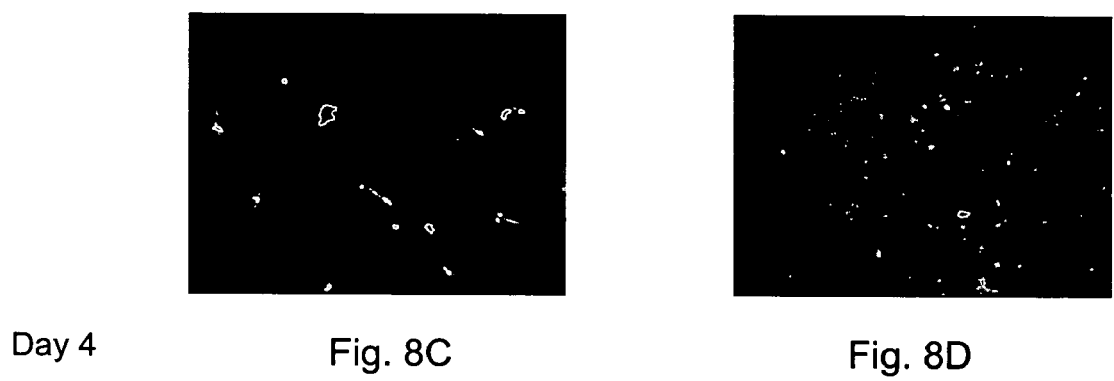
Figures 8E, 8F:

Because high density long nanowires provide the highest osteoblast adhesion and proliferation, the remainder of this Example describes the use of these nanowire surfaces for bone biotemplating applications. Further, osteoblast adhesion and proliferation on these nanowires was also investigated using fluorescence microscopy. The adhered and proliferated cells were stained using CMFDA (5-chloromethylfluorescein diacetate) and HOESCHT. Both CMFDA and HEOESCHT will stain live cells. CMFDA will stain the cytoplasm green and the HOESCHT will stain the nucleus blue. FIGS. 8A-F show fluorescence microscope images of adhered and proliferated cells on various nanowire surfaces after 1 day (FIG. 8B) and 4 days (FIGS. 8D and F) and on quartz surfaces after 1 day (FIG. 8A) and 4 days (FIGS. 8C and E). Nanowire surfaces show higher osteoblast adhesion compared to quartz surfaces. Further, no nucleus staining was seen at Day 1 on nanowire and quartz surfaces.

iv) Osteoblast Differentiation

Osteoblasts were seeded on sterilized nanowire and control surfaces and were allowed to adhere and proliferate for 4 days at 34° C. The temperature was then raised to 39° C. to stimulate the cells to differentiate and begin producing matrix. In order to investigate normal osteoblast behavior, total protein content was determined after up to 4 weeks of incubation. In order to release the intracellular protein, the adhered cells on the surfaces were lysed using 2% Triton-X detergent solution. The resulting lysate solution was then used for analysis. The total protein content was determined by a BCA (bicinchoninic acid) assay kit (Pierce Biotechnology, Inc.) and the absorbance of the solution was measured using a spectrophotometer at a wavelength of 562 nm. The absorbance was converted to protein content using an albumin standard curve. The lysate was also used to measure the concentration of alkaline phosphatase using calorimetric assay (Teco Diagnostics) at 590 nm.

Figure 9:
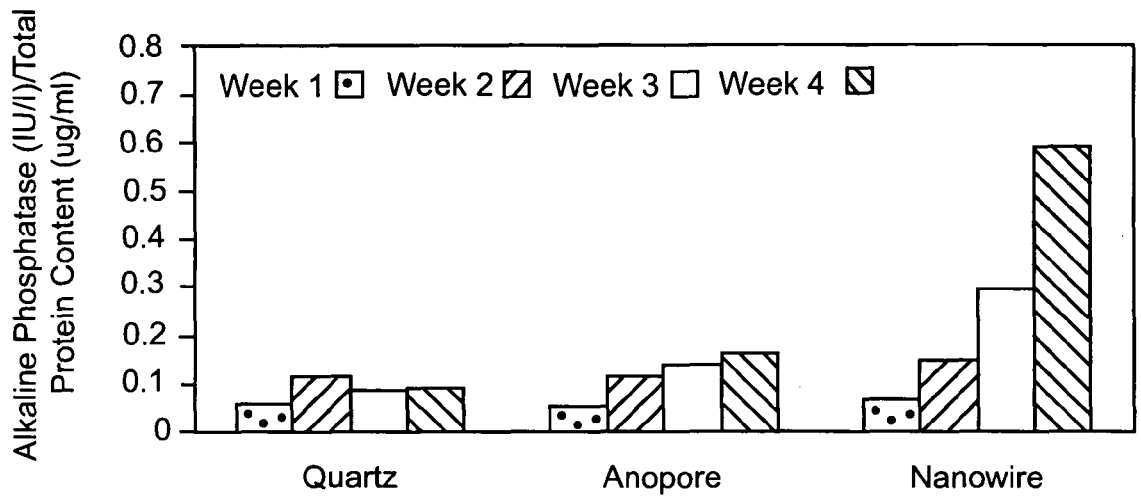
FIG. 9 shows the alkaline phosphatase activity for osteoblasts adhered on quartz, anapore and nanowire surfaces for a 4 week period.

FIG. 9 shows the alkaline phosphatase activity for osteoblasts for a 4 week period. The ALP activity was normalized with corresponding total protein content to take into account variations in number of cells present on the surface. It should be noted that the adhered cells were not proliferating during this period since they were incubated at 39° C. Therefore, the increase in ALP activity can be attributed to healthy functionality of the cells. For week 1, there is no significant difference in ALP activity for cells adhered to all the surfaces. However, for longer time periods, cells on nanowire surfaces show higher ALP activity suggesting improved performance ($p<0.01$). They also show more activity compared to commercially available ANOPORE™ membranes suggesting that nanowire surfaces are more favorable templates for osteoblast culture.

Figure 10:
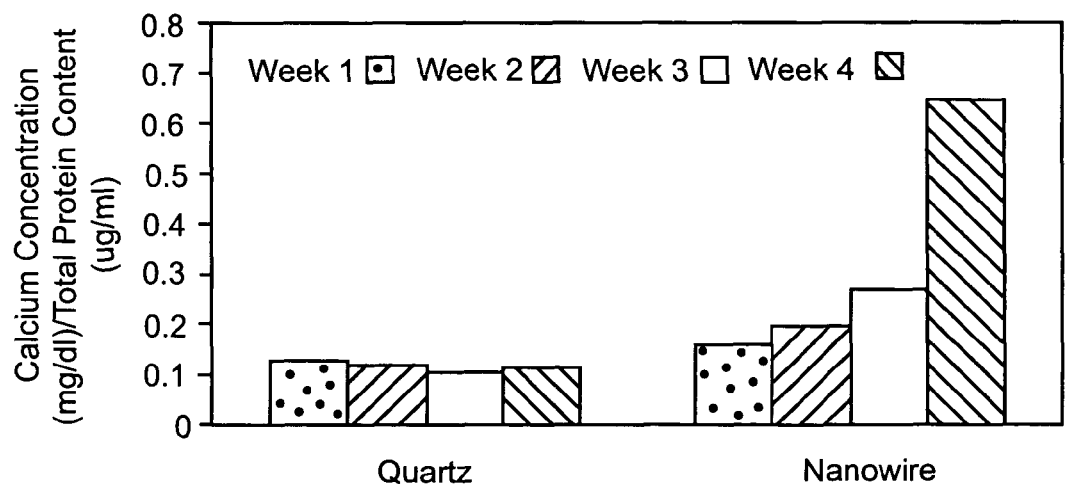
FIG. 10 shows calcium concentration as measured by colorimetric assay for nanowire and quartz (reference) surfaces.
Figure 11A:
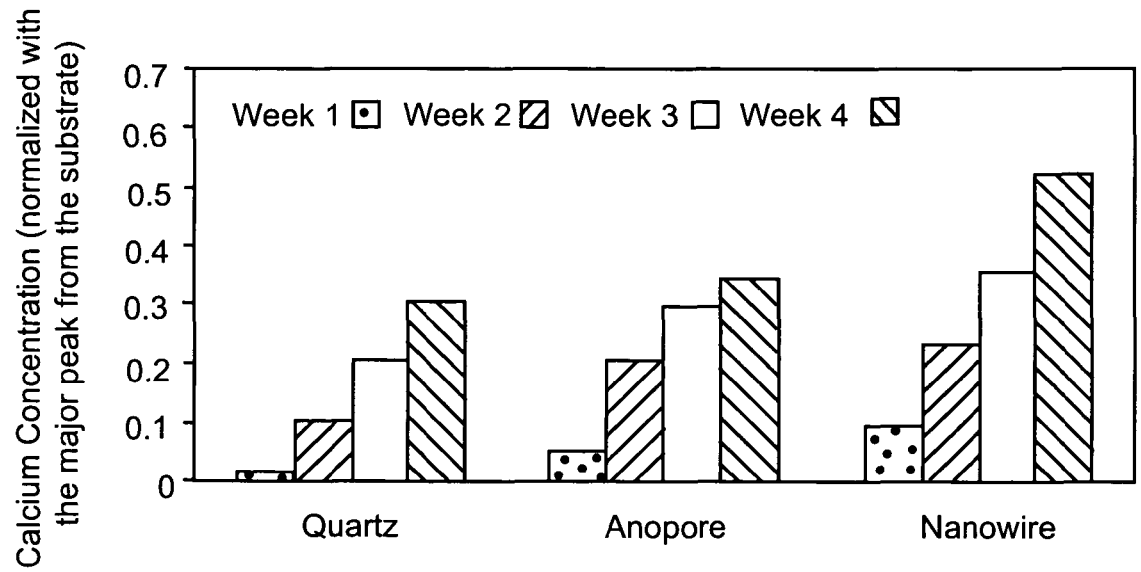
FIGS. 11A-B show calcium concentration (FIG. 11A) and phosphorous concentration (FIG. 11B) on nanowire and reference surfaces measured using XPS.
Figure 11B:
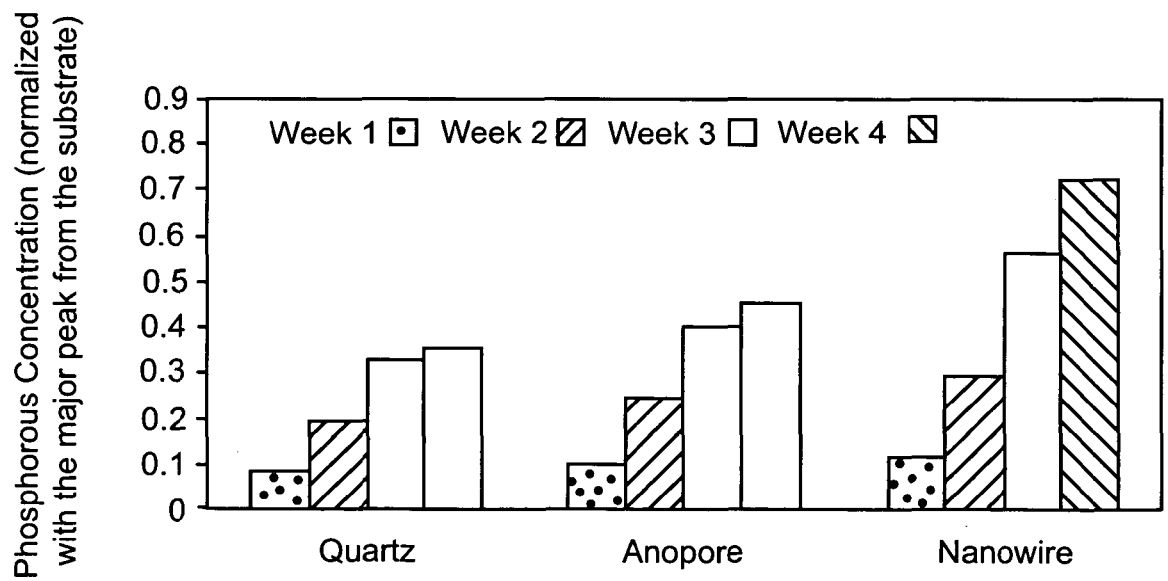

The extracellular matrix deposited by osteoblasts can be determined by measuring calcium deposited by osteoblasts on these surfaces. The deposited calcium can be stripped by dissolving it in HCl and measuring the concentration using colorimetric assay (Teco Diagnostics) at 570 nm. Similar results to that of alkaline phosphatase activity are observed for matrix composition (FIG. 10). For week 1, there is no significant difference in calcium concentration. However, for longer time periods, cells on nanowire surfaces deposited more matrix (as suggested by calcium concentration) suggesting improved performance ($p<0.01$). By week 4, the calcium concentration on nanowire surfaces increased by 3-fold. Calcium assay was not used on ANOPORE membranes since they react with acid. Thus, as a secondary characterization, X-ray photoelectron spectroscopy was used. XPS was used to detect presence of calcium and phosphorous on the surfaces after cell lysis. XPS is a sensitive surface characterization technique which measures the surface elemental concentrations. FIG. 11 shows the calcium and phosphorous concentrations obtained from XPS. Ca/Si(or Al) and P/Si(or Al) ratios are highest for all four weeks for nanowire surfaces compared to other surfaces suggesting more extracellular matrix was deposited by osteoblasts on these surfaces ($p<0.01$). Further, the amount of deposited matrix on surfaces increases with time as suggested by higher Ca/Si(or Al) and P/Si (or Al) ratios.

Figure 12A:
FIGS. 12A-H show SEM images of osteoblasts adhered on quartz (reference) surfaces after 1 week (FIGS. 12A-B), 2 weeks (FIGS. 12C-D), 3 weeks (FIGS. 12E-F) and 4 weeks (FIGS. 12G-H)
Figure 12B:
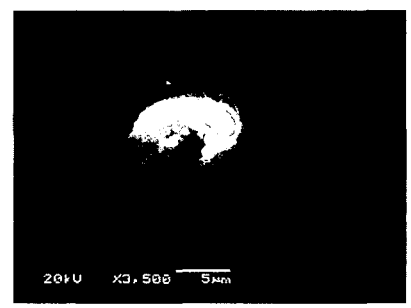
Figure 12C:
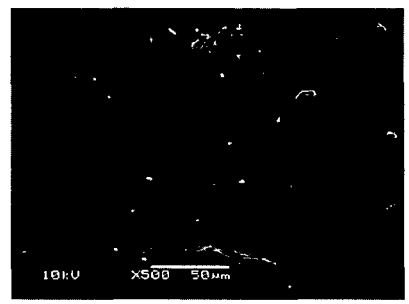
Figure 12D:
Figure 12E:
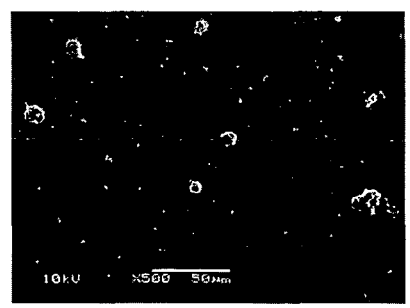
Figure 12F:
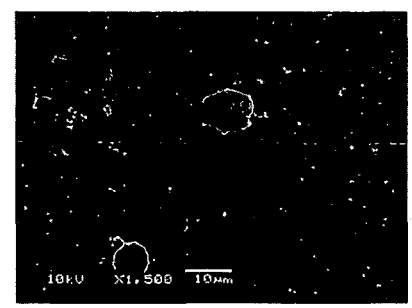
Figure 12G:
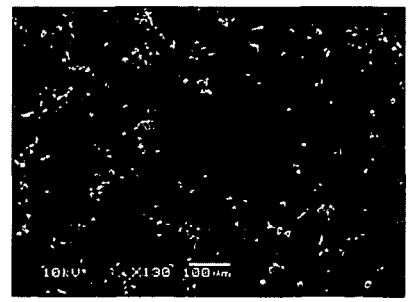
Figure 12H:
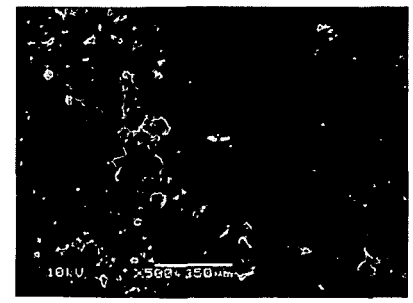

Osteoblast morphology after differentiation was investigated using scanning electron microscopy. SEM was performed on surfaces with osteoblasts after each week for a period of 4 weeks. FIGS. 12A-H show SEM images of osteoblasts adhered on quartz (reference) surfaces after 1 week (FIGS. 12A-B), 2 weeks (FIGS. 12C-D), 3 weeks (FIGS. 12E-F) and 4 weeks (FIGS. 12G-H). FIGS. 12I-P show SEM images of osteoblasts adhered on nanowire surfaces after 1 week (FIGS. 12I-J), 2 weeks (FIGS. 12K-L), 3 weeks (FIGS. 12M-N) and 4 weeks (FIGS. 12O-P). Osteoblasts show improved performance on nanowire surfaces as shown by SEM images. Osteoblasts show early signs of differentiation on nanowire surfaces compared to quartz surfaces. By the end of week 1, osteoblasts start communicating with each other which is not observed on quartz surfaces. By the end of week 2, cells extend their processes towards each other which are the first signs of cell communication and signaling. This kind of behavior is absent on quartz surfaces. By the end of week 3, osteoblasts start clustering on nanowire surfaces and start filling the surfaces with matrix around them. By the end of week 4, many clusters of osteoblasts are seen on nanowire surfaces compared to quartz surfaces. This suggests that osteoblasts perform better on nanowire surfaces and the nanoarchitecture helps in faster differentiation which is expected to result in faster bone in-growth.

The following non-limiting Example presents data from a Purdue University study that illustrates how the use of nanofiber (e.g., nanowire) surfaces as compared to current orthopedic implant materials leads to increased select osteoblast adhesion in a competitive cell adhesive environment. Various cells important for orthopedic applications were allowed to interact with: current implant materials (i.e., commercially pure titanium (Ti), Ti$_6$Al$_4$V, and CoCrMo), current implant materials with a bioactive hydroxyapatite (HA) coating (i.e., Ti coated with HA and Ti$_6$Al$_4$V coated with HA), HA used not as a coating but in bulk, and nanowire surfaces. Cells that were allowed to interact with the materials simultaneously to simulate in vivo conditions were: osteoblasts (bone-forming cells), fibroblasts (fibrous, not hard, tissue forming cells), endothelial cells, and smooth muscle cells. Fibroblasts, endothelial cells, and smooth muscle cells are considered competitive cells to osteoblasts. Data has been shown that when the functions of these cells are greater than those of osteoblasts, orthopedic implant failure occurs.

Figure 13A:
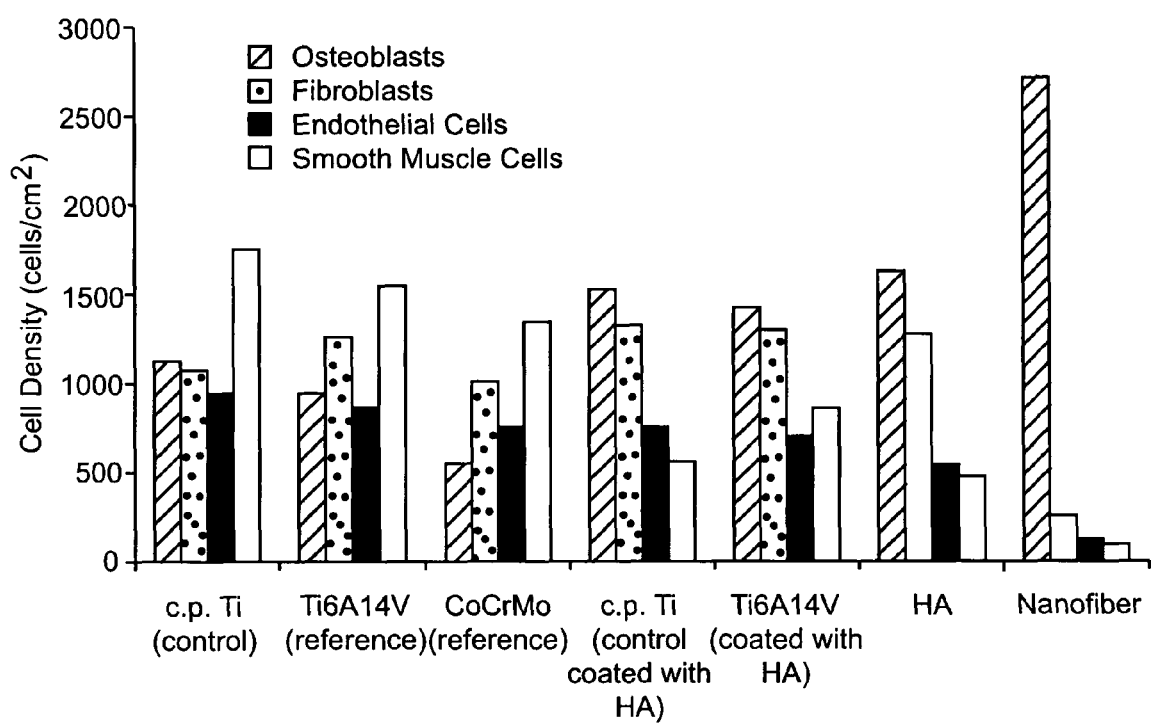
FIGS. 13A-B show the results of a competitive cell adhesion assay after 1 day (FIG. 13A) and 3 days (FIG. 13B) showing significantly more competitive adhesion and proliferation of osteoblasts (bone forming cells) on nanowire surfaces of the present invention compared to current materials used in orthopedic implant applications.
Figure 13B:
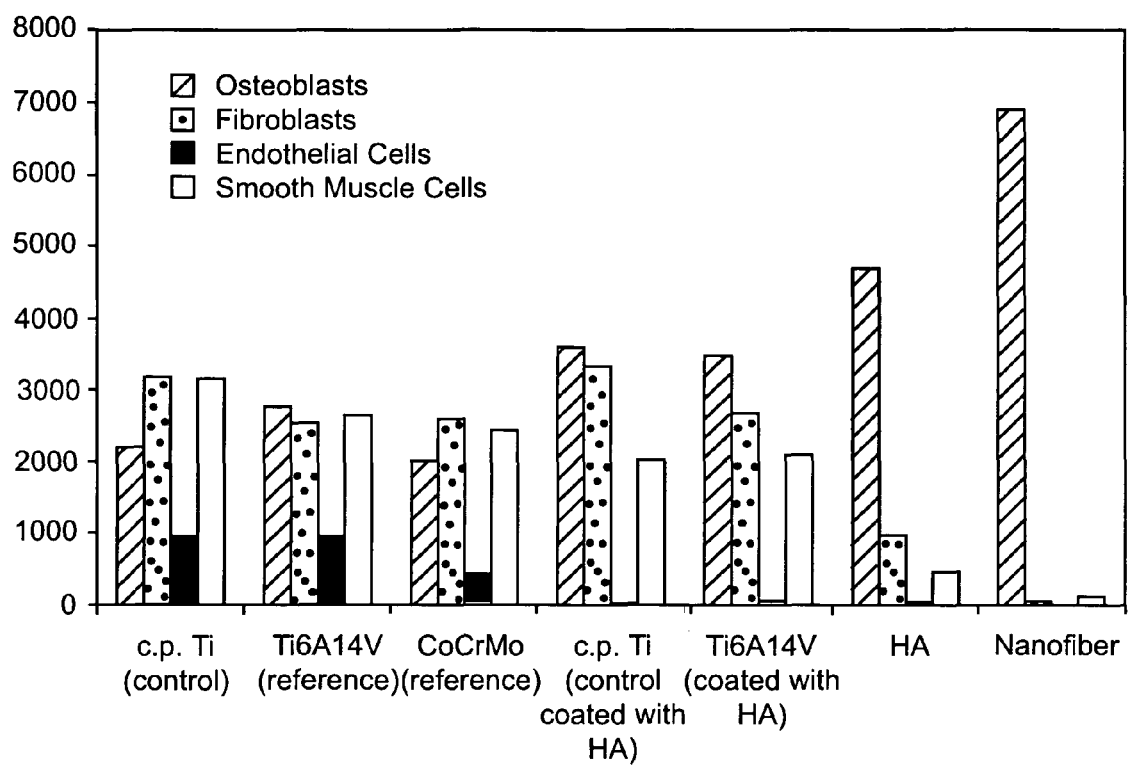

Example II i) Materials and Methods:

Each cell type was obtained from rats and was used as primary cells (used directly after isolation). Cells were seeded simultaneously at 3,500 cell/cm$^2$ onto the materials and were cultured under standard conditions for 4 hours. The nanowire surfaces used in this study were prepared by growing nanowires from 40 nm gold colloids deposited onto poly-1-lysine coated titanium coupons (1 cm$^2$) (Alfa Aesar, Ward Hill, Mass.) for 30 minutes at 480° C. The final grown nanowires were approximately 5-20 um long and 40 nm in diameter. Each cell type was fluorescently stained prior to seeding to assist in distinguishing each cell type after the adhesion experiment. After 4 hours, cells were then fixed and counted. Each experiment was done in triplicate and repeated at three separate times for statistical significance.

ii) Results and Discussion:

The results of this competitive adhesion assay showed significantly more competitive adhesion after 1 day (FIG. 13A) and proliferation after 3 days (FIG. 13B) of osteoblasts (bone forming cells) on the nanowire surfaces compared to current materials used in orthopedic implant applications. The results were even greater than the currently defined bioactive HA coatings. Equally as important, the simultaneous adhesion of competitive cells was the lowest on the nanowire surfaces compared to currently used orthopedic implant materials. These results suggest that competitive adhesion and proliferation of osteoblasts over competitive cells would be enhanced on the nanowire surfaces compared to even the best clinical materials used in orthopedics today (such as HA). Thus, it is fully expected that competitive long-term functions of osteoblasts will also be higher on the nanowire surfaces compared to those currently used as bone implants.

Example III

Synthesis of Nanowires on Nitinol Substrate

Following removal of organic residue from the Nitinol substrate surface (e.g., the surface is plasma cleaned with oxygen to remove any organics on the surface), the substrate is then placed in a CVD furnace in which it undergoes an approximate 30 minute run at approximately 480° C. to give a 6 to 10 nanometer conformal layer of microcrystalline silicon. The silicon coated material is then coated with an organic, chemical solution such as polylysine to ensure that the silicon surface is positively charged so that the gold colloid will adhere to the silicon coated surface. After the polylysine has been coated to the silicon coated surface, a liquid solution of gold colloid is deposited on the substrate for use as a catalyst within the subsequent chemical vapor deposition step. Selection of the colloid diameter is chosen based on the desired wire diameter size. The negatively charged gold colloid adheres to the positively charged surface. After gold colloid deposition, the material is then plasma cleaned to remove organics such as polylysine. Finally, the material is run thru the CVD furnace using CVD to create silicon nanowire structures from gold. During this process anisotropic crystal growth was promoted by the presence of liquid alloy/solid interface. The decomposition of silane (SiH$_4$) and gold form a liquid alloy, when the temperature is higher than the eutectic point. This "liquid" surface then becomes the preferred deposition site for incoming silicon vapor. After the liquid alloy becomes supersaturated with silicon, nanowire growth occurs by precipitation at the solid-liquid interface.

Example IV

Synthesis of Nanowires on Substrates of Silicon, Alumina and Titanium

Nanostructured surfaces comprising nanowires on substrates of silicon, alumina and titanium was performed. The process was as in Example III, but the substrate was silicon, alumina or titanium.

Example V

Synthesis of Nanowires on Substrates or Alloys Containing Ni

The synthesis proceeds according to the process in Example III, except the synthesis may be performed on alloys containing Ni. Chemical treatment, including acid etching of the Nitinol to reduce the surface-content of Ni may be used. Surface analytical techniques such as XPS (ESCA) and EDAX can be employed to correlate the Ni content of the substrate surface with wire growth.

Example VI

Synthesis of Nanostructured Surfaces with Hemocompatible Coating of TiO$_2$

Nanowires were prepared as in Example III. Deposition of TiO$_2$ using atomic layer deposition (ALD) was performed. This results in core-shell wire architectures that improve biostability and hemocompatibility while retaining the gecko adhesive property of the coating. ALD is a preferred technology for depositing thin conformal layers of material on the surface of nanowires at low temperature.

Example VII

Synthesis of a Hollow Nanotube for Drug Delivery

Silicon nanowires are synthesized using the VLS technique. Oriented or unoriented nanowires may be synthesized depending on conditions. The outer shell of the wires may be converted to silicon oxide by high temperature thermal processing. Alternatively, silicon oxide may be deposited on the wires at low temperatures using PECVD. The core silicon can then be etched away in the gas phase using, for example XeF$_2$. Tubes of different compositions may be made using this process as a mold.

Example VIII

Synthesis of a High Surface Area Contact Electrical Contact

A hollow nanotube is created as in Example VII. The silicon oxide nanotube may be used as a template for coating with a metal such as Ti by atomic layer deposition (ALD) then etched away, using for example XeF$_2$ or other suitable etchant, thus forming high surface area electrical contacts suitable for use in applications such as pacemaker leads.

Example IX

Coefficient of Friction of Adherent Nanofiber Substrates

A Micro Scratch Tester (Micro Photonics, Torrance, Calif.) was used to determine the difference in coefficient of friction between a nanofiber surface of the invention and a similar surface without nanofibers. A glass surface (i.e., a borosilicate glass microscope slide) that was chemically similar to silicon dioxide nanowires (i.e., one possible type/construction of nanofibers of the invention) was tested against a nanofiber surface similar to those used in previous example, supra. The nanofiber surface had a coefficient of friction of 2.0 while the glass slide (without nanofibers) had a coefficient of friction of 0.08.

Example X

Friction Forces/Gripping of Adherent Nanofiber Substrates

A 5-inch piece of fresh pig aorta obtained commercially was clamped at each end while immersed in a tank of whole milk. A pair of typical medical clamps (Novare® Medical, Cupertino, Calif.) was clamped on to the center of the aorta. These clamps, as is typical with many medical clamps, use silicon rubber disposable inserts in the "jaws" of the clamp. Such devices are currently considered to be state of the art for traction/holding of tissues in medical settings. The "clamp force" of the Novare® clamp (i.e., the pressure exerted upon the vessel) was determined by the jaw position of the clamps. In other words, the jaw position (how tightly the jaws were clamped together) determined the clamping force upon the aorta. The handle of the clamps was attached to a load cell that was programmed to pull the clamps at a set rate normal to the aorta. The maximum force reached before the clamps slipped off of the aorta was thus measured.

The test was repeated with the Novare® clamps three times. The average force applied to cause slippage of the clamps off of the aorta was 4 lbs. The clamp inserts were then changed from the traditional silicon rubber to a nanofiber surface of the invention. The adherent nanofiber surface comprised silicon nanowires grown on a silicon wafer. The nanofibers in such example were of 40 nm average diameter and 30 microns average length and were present at about 5 nanofibers per square micron of substrate. The clamp surface area of the nanofiber surface was the same as the surface measured for the rubber inserts. Additionally, the jaw position of the clamps was equivalent in each testing. The average force required to slip the nanowire surface off of the aorta was 7 lbs. No major differences were observed in regard to tissue damage on the aorta from the clamping action. Additionally, both hydrophilic and hydrophobic nanofiber surfaces produced similar adherent action upon the vessel. As another control, the silicon nanowire surfaces were reversed in the clamps so that the back of the wafer (i.e., without nanofibers) was exposed to the aorta. In such example, a force of only 2 lbs was required to slip the clamp off of the vessel.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A wound dressing comprising:
a plurality of nanostructures; and
a bandage that includes a fibrous web, wherein at least a portion of the plurality of nanostructures are incorporated within or associated with the fibrous web;
wherein at least a portion of the plurality of nanostructures include at least one coating material, wherein the nanostructures including the coating material are wholly or partially coated with the at least one coating material, and
wherein a surface of the bandage is capable of adhering to a biological tissue surface due at least to van der Waals forces between at least a portion of the plurality of nanostructures and the biological tissue surface.

2. The wound dressing of claim 1, wherein the nanostructures comprise nanowires, nanofibers, nanoparticles, nanodots, nanotetrapods, or nanotubes.

3. The wound dressing of claim 1, wherein the nanostructures comprise silicon oxide.

4. The wound dressing of claim 1, wherein the at least one coating material comprises a biocompatible polymer.

5. The wound dressing of claim 1, wherein the nanostructures include silicon nanowires coated with an oxide layer.

6. The wound dressing of claim 1, wherein at least a portion of the nanostructures comprise a material independently selected from the group consisting of silicon, glass, quartz, metals and metal alloys, inorganic polymers and copolymers, thermoset plastics, organic polymers including proteins, semiconductors, ceramics, TiO, ZnO, ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InN, InP, InAs, InSb, PbS, PbSe, PbTe, AlS, AlP, AlSb, Ge, SiGe, SiO, SiO$_2$, silicon carbide and silicon nitride.

7. The wound dressing of claim 1, wherein the at least one coating material includes a first coating material and a second coating material, wherein a first portion of the plurality of nanostructures is coated with the first coating material and a second portion of the plurality of nanostructures is coated with the second coating material.

8. The wound dressing of claim 1, wherein the at least one coating material includes fibrin.

9. The wound dressing of claim 1, wherein the at least one coating material includes fibrinogen.

10. The wound dressing of claim 1, wherein the at least one coating material includes an antibacterial coating material.

11. The wound dressing of claim 10, wherein the antibacterial coating material comprises silver, zinc, or titanium oxide.

12. The wound dressing of claim 1, wherein the at least one coating material includes a coating material which promotes wound healing.

13. The wound dressing of claim 1, wherein the at least one coating material includes a coating material which promotes cell growth.

14. The wound dressing of claim 1, wherein the at least one coating material includes at least one growth factor.

15. The wound dressing of claim 1, wherein the at least one coating material includes a hydrophobic coating material.

16. The wound dressing of claim 1, wherein the at least one coating material includes a flowable material.

17. The wound dressing of claim 1, wherein the at least one coating material includes an adhesive.

18. The wound dressing of claim 1, wherein at least a portion of the plurality of nanostructures have adhesive properties.

19. The wound dressing of claim 1, wherein the wound dressing is flexible.

20. The wound dressing of claim 1, wherein the wound dressing is air-penetrable.

21. The wound dressing of claim 1, wherein the wound dressing is water-repellent.

22. The wound dressing of claim 1, wherein the fibrous web is porous.

23. The wound dressing of claim 1, wherein the wound dressing adheres to both dry surfaces and wet surfaces.

24. The wound dressing of claim 1, wherein the wound dressing does not chemically bond to the biological tissue surface.

25. The wound dressing of claim 1, wherein the at least one coating material includes a coating material which prevents adhesion to a biological tissue surface.

26. The wound dressing of claim 1, wherein a surface of the bandage is capable of adhering to a biological tissue surface due to at least friction forces between at least a portion of the plurality of nanostructures and the biological tissue surface.

27. The wound dressing of claim 1, wherein at least a portion of the plurality of nanostructures are curved or curled.

28. The wound dressing of claim 1, wherein at least a portion of the plurality of nanostructures are bent, curved, curled, coiled.

29. The wound dressing of claim 1, wherein at least a portion of the plurality of nanostructures have an average length of from about 1 nm to at least about 500 microns.

30. The wound dressing of claim 1, wherein at least a portion of the plurality of nanostructures have an average length of from about 5 nm to at least about 1 micron.

31. The wound dressing of claim 1, wherein at least a portion of the plurality of nanostructures have an average length of from about 10 microns to at least about 125 microns.

32. The wound dressing of claim 1, wherein at least a portion of the plurality of nanostructures have an average length of from about 50 microns to at least about 100 microns.

33. The wound dressing of claim 1, wherein at least a portion of the plurality of nanostructures have an average diameter of from about 5 nm to at least about 1 micron.

34. The wound dressing of claim 1, wherein at least a portion of the plurality of nanostructures have an average diameter of from about 5 nm to at least about 500 microns.

35. The wound dressing of claim 1, wherein at least a portion of the plurality of nanostructures have an average diameter of from about 20 nm to at least about 250 nm.

36. The wound dressing of claim 1, wherein at least a portion of the plurality of nanostructures have an average diameter of from about 20 nm to at least about 200 nm.

37. The wound dressing of claim 1, wherein at least a portion of the plurality of nanostructures have an average diameter of from about 40 nm to at least about 200 nm.

38. The wound dressing of claim 1, wherein at least a portion of the plurality of nanostructures have an average diameter of from about 50 nm to at least about 150 nm.

39. The wound dressing of claim 1, wherein at least a portion of the plurality of nanostructures have an average diameter of from about 75 nm to at least about 100 nm.

40. The wound dressing of claim 1, wherein at least a portion of the plurality of nanostructures have an aspect ratio aspect ratio greater than one.

41. The wound dressing of claim 1, wherein at least a portion of the plurality of nanostructures have an aspect ratio of 2 or greater.

42. The wound dressing of claim 1, wherein at least a portion of the plurality of nanostructures have an aspect ratio greater than about 10.

43. The wound dressing of claim 1, wherein at least a portion of the plurality of nanostructures have an aspect ratio greater than about 20.

44. The wound dressing of claim 1, wherein at least a portion of the plurality of nanostructures have an aspect ratio greater than about 100.

45. The wound dressing of claim 1, wherein at least a portion of the plurality of nanostructures have an aspect ratio greater than about 200.

46. The wound dressing of claim 1, wherein at least a portion of the plurality of nanostructures comprise nanowires which have an aspect ratio greater than about 500.

47. The wound dressing of claim 1, wherein at least a portion of the plurality of nanostructures comprise nanowires which have a substantially uniform diameter along the length of the nanowire.

48. The wound dressing of claim 1, wherein at least a portion of the plurality of nanostructures comprise nanowires which have a non-uniform diameter along the length of the nanowire.

49. The wound dressing of claim 1, wherein a first portion of the plurality of nanostructures have a different size and/or shape than a second portion of the plurality of nanostructures.

50. The wound dressing of claim 1, wherein at least a portion of the plurality of nanostructures protrude at least 10 nm above a first surface of the wound dressing.

51. The wound dressing of claim 1, wherein at least a portion of the plurality of nanostructures protrude at least 100 nm above a first surface of the would dressing.

52. The wound dressing of claim 1, wherein the van der Waals forces comprise from about 0.1 N/cm$^2$ to about 100 N/cm$^2$.

53. The wound dressing of claim 1, wherein the van der Waals forces comprise from about 1.0 N/cm$^2$ to about 25 N/cm$^2$.

54. The wound dressing of claim 1, wherein the van der Waals forces comprise from about 2.0 N/cm$^2$ to about 10 N/cm$^2$.

55. The wound dressing of claim 1, wherein the density of contact points per unit area between one or more surfaces of the wound dressing and the biological tissue comprises from about 1 contact point per micron$^2$ of biological tissue surface to about 2000 contact points per micron$^2$ of biological tissue surface.

56. The wound dressing of claim 1, wherein the density of contact points per unit area between one or more surfaces of the wound dressing and the biological tissue comprises from about 50 contact points per micron$^2$ of biological tissue surface to about 250 contact points per micron$^2$ of biological tissue surface.

57. The wound dressing of claim 1, wherein at least a portion of the plurality of nanostructures comprises an average density on one or more surfaces of the wound dressing from about 0.1 nanostructures per square micron to at least about 2,500 nanostructures per square micron.

58. The wound dressing of claim 1, wherein the plurality of nanostructures comprises an average density on one or more surfaces of the wound dressing from about 1 nanostructure per square micron to at least about 500 nanostructures per square micron.

59. The wound dressing of claim 1, wherein at least a portion of the plurality of nanostructures comprises an average density on one or more surfaces of the wound dressing from about 10 nanostructures per square micron to at least about 250 nanostructures per square micron.

60. The wound dressing of claim 1, wherein at least a portion of the plurality of nanostructures comprises an average density on one or more surfaces of the wound dressing from about 50 nanostructures per square micron to at least about 100 nanostructures per square micron.

61. The wound dressing of claim 1, wherein the fibrous web includes a woven or non-woven fibrous mat.

62. The wound dressing of claim 4, wherein the biocompatible polymer is chosen from the group consisting of polyglycolic acid, poly-L-lactic acid, poly-DL-lactic acid, poly-D-lactic acid, poly(lactic acid-glycolic acid) copolymer, poly-epsilon-caprolactone, poly(glycolic acid-caprolactone) copolymer, polyamino acid, polyanhydride, polyorthoester, polycaprolactone, poly(lactide-co-glycolide), poly(hydroxybutyrate), poly(hydroxybutyrate-co-valerate), polydioxanone, poly(glycolic acid-co-trimethylene carbonate), polyphosphoester, polyphosphoester urethane, cyanoacrylates, poly(trimethylene carbonate), poly(iminocarbonate), polyalkylene oxalates, polyphosphazenes, hyaluronic acid, cellulose, starch, collagen, and copolymers and mixtures thereof.

* * * * *

UNITED STATES PATENT AND TRADEMARK OFFICE
CERTIFICATE OF CORRECTION

| | |
|---|---|
| PATENT NO. | : 7,972,616 B2 |
| APPLICATION NO. | : 11/330722 |
| DATED | : July 5, 2011 |
| INVENTOR(S) | : Robert S. Dubrow et al. |

It is certified that error appears in the above-identified patent and that said Letters Patent is hereby corrected as shown below:

IN THE CLAIMS:

In claim 40, column 88, line 3, please delete "aspect ratio".

In claim 51, column 88, line 39, please delete "would" and insert --wound--.

Signed and Sealed this
Sixteenth Day of August, 2011

David J. Kappos
*Director of the United States Patent and Trademark Office*